US007875707B2

(12) United States Patent
Meutermans et al.

(10) Patent No.: US 7,875,707 B2
(45) Date of Patent: *Jan. 25, 2011

(54) DISACCHARIDES FOR DRUG DISCOVERY

(75) Inventors: Wim Meutermans, Toowong (AU); Michael West, Hemmant (AU); George Adamson, Hampshire (GB); Giang Thanh Le, Mt. Gravatt (AU); Nicholas B. Drinnan, Highgate Hill (AU); Giovanni Abbenante, Sampsonvale (AU); Bernd Becker, New Farm (AU); Matthias Grathwohl, Constance (DE); Premraj Rajaratnam, Eight Mile Plains (AU); Gerald Tometzki, Manly West (AU)

(73) Assignee: Alchemia Limited, Eight Mile Plains (AU)

( * ) Notice: Subject to any disclaimer, the term of this patent is extended or adjusted under 35 U.S.C. 154(b) by 1096 days.

This patent is subject to a terminal disclaimer.

(21) Appl. No.: 10/513,286

(22) PCT Filed: Apr. 24, 2003

(86) PCT No.: PCT/AU03/00494

§ 371 (c)(1), (2), (4) Date: Sep. 27, 2005

(87) PCT Pub. No.: WO03/093286

PCT Pub. Date: Nov. 13, 2003

(65) Prior Publication Data

US 2006/0121530 A1 Jun. 8, 2006

(30) Foreign Application Priority Data

May 3, 2002 (AU) ..................................... PS2138

(51) Int. Cl.
C07H 1/00 (2006.01)
C07H 15/00 (2006.01)
C07H 17/00 (2006.01)
C07H 5/04 (2006.01)
C07H 5/06 (2006.01)
C07G 3/00 (2006.01)
C07G 11/00 (2006.01)
C08B 37/00 (2006.01)
C13K 5/00 (2006.01)
C13K 7/00 (2006.01)

(52) U.S. Cl. ....................... 536/1.11; 536/4.1; 536/18.7; 536/123.13

(58) Field of Classification Search ................. 536/1.11, 536/4.1, 18.7, 123.13
See application file for complete search history.

(56) References Cited

U.S. PATENT DOCUMENTS 5,414,073 A 5/1995 Okuyama et al.

2006/0142217 A1 6/2006 Meutermans et al.

FOREIGN PATENT DOCUMENTS

| WO | WO 97/34623 | 9/1997 |
|---|---|---|
| WO | WO 98/30570 | 7/1998 |
| WO | WO 98/38197 | 9/1998 |
| WO | WO 98/53813 | 12/1998 |
| WO | WO 99/26956 | 6/1999 |
| WO | WO 00/64915 | 11/2000 |
| WO | WO 01/51499 | 7/2001 |
| WO | WO 02/32963 | 4/2002 |

OTHER PUBLICATIONS

Chemical Abstracts Database, CAS Registry No. 135877-15-5, entered on Aug. 30, 1991.*
Maeda, H., Ishida, H., Kiso, M., Hasegawa, A. (1995) Synthetic Studies on Sialoglycoconjugates 71: Synthesis of Sulfo- and Sialyl-Lewis X Epitope Analogs Containing the 1-Deoxy-N-Acetylglucosamine in Place of N-Acetylglucosamine Residue. Journal of Carbohydrate Chemistry, vol. 14, No. 3, p. 369-385.*
Flitsch, S.L. (2005) Glycosylation with a Twist. Nature, vol. 437, p. 201-202.*
Seeberger, P.H., Haase, W.-C. (2000) Solid-Phase Oligosaccharide Synthesis and Combinatorial Carbohydrate Libraries. chemical Reviews, vol. 100, No. 12, p. 4349-4394.*
Greene, T.W. and Wuts, P.G.M. (1991) Protective Groups in Organic Synthesis, published by John Wiley & Sons, Inc., p. 1-4, 10-15, 47-55, 60-61 and 411-416.*
Gruner et al, "Carbohydrate-Based Mimetics in Drug Design: Sugar Amino Acids and Carbohydrate Scaffolds", Chem. Rev. 102:491-514 (2002).
Nishio et al, "Synthesis And Antifungal Activities Of Pradimicin A Derivatives Modification Of The Alanine Moiety", The Journal of Antibiotics 46(3):494-499 (1993).
Sawada et al, "Pradimicin Q, A New Pradimicin Aglycone, With α-Glucosidase Inhibitory Activity", The Journal of Antibiotics 46(3):507-510 (1993).
Oki et al, "Pradimicins A, B And C: New Antifungal Antibiotics II. In Vitro and In Vivo Biological Activities", The Journal of Antibiotics XLIII(7):763-770 (1990).
Merck Manual Home Edition, subject "Antibiotics". Retrieved on [Oct. 14, 2008]. Retrieved online from [http://www.merck.com/mmhe/print/sec17/ch192/ch192a.html].
Kim et al., "A General Strategy for Stereoselective Glycosylations," J. Am.Chem. Soc. 2005, 127, 12090-12097.

* cited by examiner

*Primary Examiner*—Shaojia Anna Jiang
*Assistant Examiner*—Scarlett Goon
(74) *Attorney, Agent, or Firm*—Nixon & Vanderhye P.C.

(57) ABSTRACT

Methods are described for the preparation of combinatorial libraries of potentially biologically active disaccharide compounds. These compounds are variously functionalized, with a view to varying lipid solubility size, function an other properties, with the particular aim of discovering novel drug or drug-like compounds, or compounds with useful properties. The invention provides intermediates, processes and synthetic strategies for the solution or solid phase synthesis of disaccharides, variously functionalized about the sugar ring, including the addition of aromaticity and charge, and the placement of pharmaceutically useful groups and isosteres.

7 Claims, No Drawings

DISACCHARIDES FOR DRUG DISCOVERY

This application is the US national phase of international application PCT/AU2003/000494 filed on 24 Apr. 2003, which designated the U.S. and claims priority to AU Application No. PS 2138, filed 3 May 2002. The entire contents of these applications are incorporated herein by reference.

FIELD OF THE INVENTION

This invention relates to methods for the preparation of combinatorial libraries of potentially biologically active disaccharide compounds. These compounds are variously functionalized, with a view to varying lipid solubility, size, function and other properties, with the particular aim of discovering novel drug or drug-like compounds, or compounds with useful properties. The invention provides intermediates, processes and synthetic strategies for the solution or solid phase synthesis of disaccharides, variously functionalised about the sugar ring, including the addition of aromaticity and charge, and the placement of pharmaceutically useful groups and isosteres.

BACKGROUND OF THE INVENTION

From a drug discovery perspective, carbohydrate pyranose and furanose rings and their derivatives are well suited as templates. Each sugar represents a three-dimensional scaffold to which a variety of substituents can be attached, usually via a scaffold hydroxyl group, although occasionally a scaffold carboxyl or amino group may be present for substitution. By varying the substituents, their relative position on the sugar scaffold, and the type of sugar to which the substituents are coupled, numerous highly diverse structures are obtainable. An important feature to note with carbohydrates, is that molecular diversity is achieved not only in the type of substituents, but also in the three dimensional presentation. The different stereoisomers of saccharides that occur naturally (examples include glucose, galactose, mannose etc,FIG. 1), offer the inherent structural advantage of providing alternative presentation of substituents.

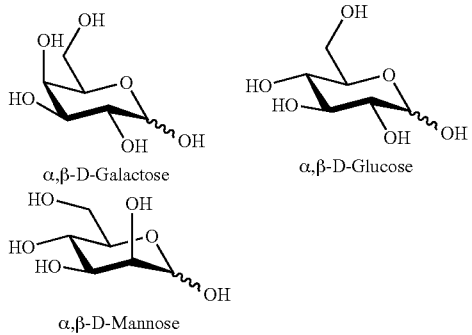

FIG. 1

Although there are a number of examples of monosaccharides being used as scaffolds for drug discovery purposes[i,ii,iii], there are only a limited number of examples of disaccharides or higher saccharides being used as templates for the presentation of pharmaceutically useful functional groups.

Derivatised disaccharides and higher saccharides, represent a new class of compounds for drug discovery that are able to address a significant and different group of receptors from those addressed by monosaccharide scaffolds. This group or receptors can be broadly described as those receptors in which the critical binding groups are distal to each other. In principle, monosaccharide scaffolds can be used to address up to five binding groups (more usually 3 binding groups would be chosen), the connection points on the scaffold are each separated by between 1 and 5 angstroms in space. Disaccharide scaffolds on the other hand can accommodate up to eight binding groups although more usually 3-4 binding groups would be chosen, the connection points for each of these groups being separated by as much as 10 angstroms in space. Obviously the appended functional groups may be separated by even greater distances in 3-dimensional space. The replacement of the glycosidic bond linking the two monosaccharide components with a spacer group can further increase the separation between binding groups of interest.

The ability to address more distally placed binding groups is an important feature for a number of biological receptor molecules including the G-protien coupled receptors, where at the extra-cellular opening to many of these receptors, the width of the binding channel is up to 14 angstroms. Additionally, disaccharide scaffolds can be used as probes of interactions which involve large surface areas for example the protein-protien interaction of the CD4-GP120 system, an important interaction in the aetiology of the human immunodeficiency virus.

Through the development of a range of selectively protected and modified monosaccharide, cyclitols and tetrahydropyran building blocks, we have developed a system that allows the chemical synthesis of highly structurally and functionally diverse derivatised disaccharide and disaccharide analogue structures, of both natural and unnatural origin. The diversity accessible is particularly augmented by the juxtaposition of both structural and functional aspects of the molecules. In order to access a wide range of diverse structures, stereo-center inversion chemistry is required, so as to achieve non-naturally occurring and hard to get sugars and sugar analogues in a facile manner. Other chemistries are also required that provide unnatural deoxy or deoxy amino derivative which impart greater structural stability to the drug-like target molecules. With a suite of reagents to effect a suitable range of chemistries on a solid support, allowing such things as; wide functional diversity, highly conserved intermediates, a limited number of common building block to be required, and with suitable chemistry to allow access to unusual carbohydrate stereo-representations and including access to deoxy and deoxy amino analogues, a methodology is then established that can create focused libraries for a known target, or alternatively diversity libraries for unknown targets for random screening.

It will be clearly understood that, although a number of prior art publications are referred to herein, this reference does not constitute an admission that any of these documents forms part of the common general knowledge in the art, in Australia or in any other country.

Many of the traditional methods of carbohydrate synthesis have proved to be unsuitable to a combinatorial approach, particularly because modern high-throughput synthetic systems require procedures to be readily automatable. The compounds and processes described herein are particularly suited to the solid and solution phase combinatorial synthesis of carbohydrate-based libraries, and are amenable to automation. The methods of the invention yield common intermediates that are suitably functionalized to provide diversity in the structure of the compounds so generated. Using the method described, it is possible to introduce varied functionality in order to modulate both the biological activity and pharmacological properties of the compounds generated.

Thus the compounds and methods disclosed herein provide the ability to produce random or focused combinatorial-type libraries for the discovery of other novel drug or drug-like compounds, or compounds with other useful properties in an industrially practical manner.

SUMMARY OF THE INVENTION

In a first aspect, the invention provides disaccharide compounds of formula I

A-d-L-e-B    formula I

In which the groups A and B are independently chosen from

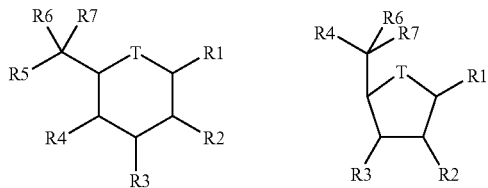

in which the ring may be of any configuration and the anomeric center where present may be of either the α or β configuration;
Independently for each ring
  T may be O or $CH_2$;
  R6 and R7 are hydrogen, or together form a carbonyl oxygen;
  R1 may be hydrogen, —N(Z)Y, C(Z)Y, OZ or SZ wherein;
When R1 is N(Z)Y
  Y is selected from hydrogen, or the following;

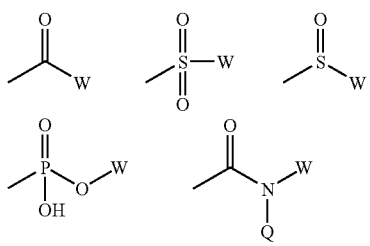

Z is selected from hydrogen or X1;
Q is selected from hydrogen or W;
The groups Z and Y may be combined to form a monocyclic or bicyclic ring structure of 4 to 10 atoms. This ring structure may be further substituted with X1 groups;

The groups W are independently selected from alkyl, alkenyl, alkynyl, heteroalkyl, aryl, heteroaryl, arylalkyl or heteroarylalkyl of 1 to 20 atoms which is optionally substituted, branched and/or linear. Typical substituents include but are not limited to OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid;

The groups X1 are independently selected from alkyl, alkenyl, alkynyl, heteroalkyl, acyl, arylacyl, heteroarylacyl, aryl, heteroaryl, arylalkyl or heteroarylalkyl of 1 to 20 atoms which is optionally substituted, branched and/or linear. Typical substituents include but are not limited to OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid;

Where R1 is C(Z)Y;
  Y, where present, is selected from hydrogen, double bond oxygen (=O) to form a carbonyl, or triple bond nitrogen to form a nitrile.
  Z may be optionally absent, or is selected from hydrogen or X2
  Wherein X2 is independently selected from alkyl, alkenyl, alkynyl, heteroalkyl, aminoalkyl, aminoaryl, aryloxy, alkoxy, heteroaryloxy, aminoaryl, aminoheteroaryl, thioalkyl, thioaryl or thioheteroaryl, acyl, arylacyl, heteroarylacyl, aryl, heteroaryl, arylalkyl or heteroarylalkyl of 1 to 20 atoms which is optionally substituted, branched and/or linear. Typical substituents include but are not limited to OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, aminoalkyl, aminoaryl, aminoheteroaryl, thioalkyl, thioaryl or thioheteroaryl, which may optionally be further substituted;

The groups Z and Y may be combined to form a monocyclic or bicyclic ring structure of 4 to 10 atoms. This ring structure may be further substituted with X1 groups;
Where R1 is OZ or SZ,
Z is selected from hydrogen or X3,
  Wherein X3 is independently selected from alkyl, alkenyl, alkynyl, heteroalkyl, acyl, arylacyl, heteroarylacyl, aryl, heteroaryl, arylalkyl or heteroarylalkyl of 1 to 20 atoms which is optionally substituted, branched and/or linear. Typical substituents include but are not limited to OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, aminoalkyl, aminoaryl, aminoheteroaryl, thioalkyl, thioaryl or thioheteroaryl, which may optionally be further substituted;

The groups R2, R3, R4 and R5 are independantly selected from the group consisting of hydrogen, $N_3$, OH, OX4, N(Z)Y, wherein N(Z)Y is as defined above or additionally Y is

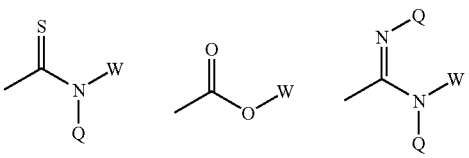

where Q and W are as defined above, and X4 is independently selected from alkyl, alkenyl, alkynyl, heteroalkyl, aminoalkyl, aminoaryl, aryloxy, alkoxy, heteroaryloxy, aminoaryl, aminoheteroaryl, thioalkyl, thioaryl or thioheteroaryl, acyl, arylacyl, heteroarylacyl, aryl, heteroaryl, arylalkyl or heteroarylalkyl of 1 to 20 atoms which is optionally substituted, branched and/or linear. Typical substituents include but are not limited to OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid;

The groups Z and Y may be combined to form a monocyclic or bicyclic ring structure of 4 to 10 atoms. This ring structure may be further substituted with X1 groups;

The groups A and B are linked together with a linking structure d-L-e, in which the groups d and e represent the connection points for A and B and replace one of the groups R1,R2, R3,R4,or R5 in each of the groups A and B and form the connection point for the linker L.

The groups d and e are independently chosen from a covalent bond or the following list:

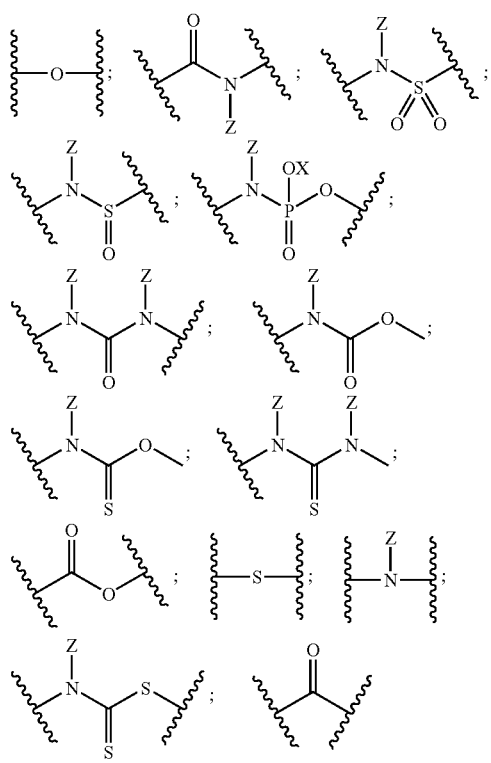

L may be absent, or is selected from alkyl, cycloalkyl, alkenyl, cycloalkenyl, alkynyl, heteroalkyl, cycloheteroalkyl, aryl, heteroaryl, arylalkyl or heteroarylalkyl of 1 to 12 atoms which is optionally substituted, branched and/or linear, saturated or unsaturated. Typical substituents include but are not limited to OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, carbonyl, substituted or unsubstituted imine, sulfate, sulfonamide, phosphate, phosphoramide, hydrazide, hydroxamate, hydroxamic acid, heteroaryloxy, aminoalkyl, aminoaryl, aminoheteroaryl, thioalkyl, thioaryl or thioheteroaryl, which may optionally be further substituted;

It is understood that the rules of molecular stoichiometry will be upheld by the default addition of hydrogens atoms as required.

A preferred embodiment of the first aspect provides for compounds of formula I in which in group A, T is oxygen, group A is a pyranose ring, The linker, d-L-e, is a glycosidic linkage formed between the anomeric position R1 of group A, and any position R1 to R5 of group B, such that the d is (—O—), L is absent, and e is a covalent bond.

Importantly, The R groups on each ring may be selected independently from each other. For example, R2 on ring A may be different from R2 on ring B.

Exemplary Structure of this Embodiment Include but are not Limited to:

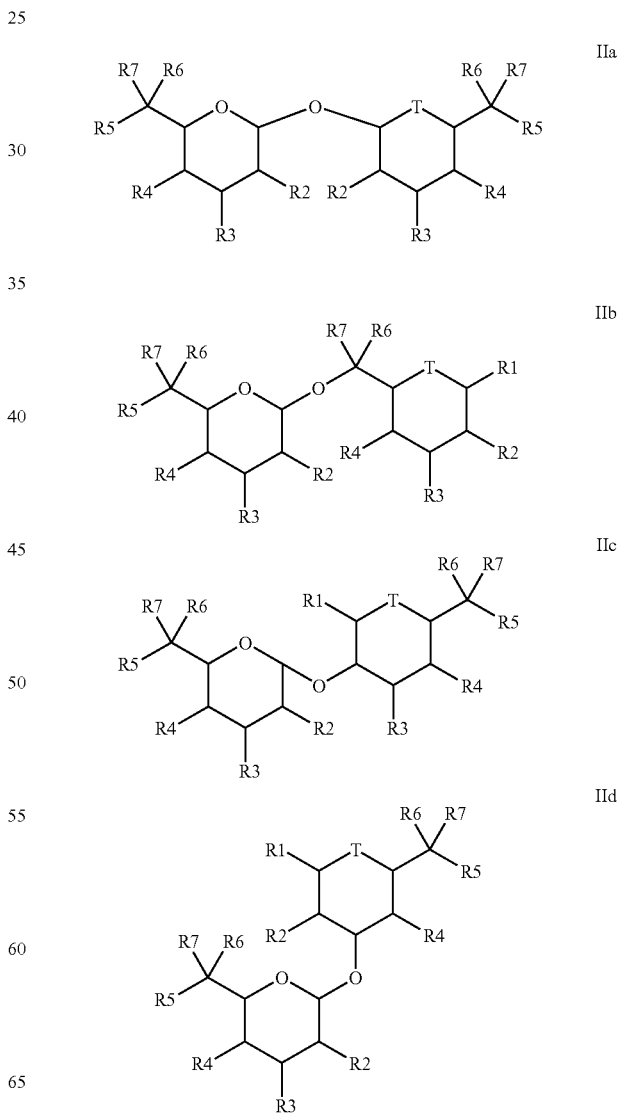

-continued

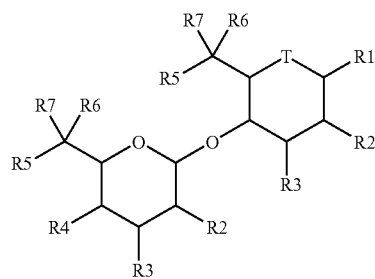
IIe

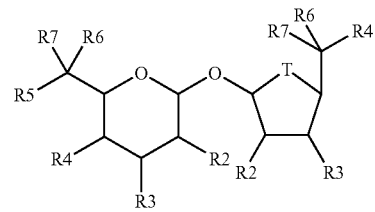
IIf

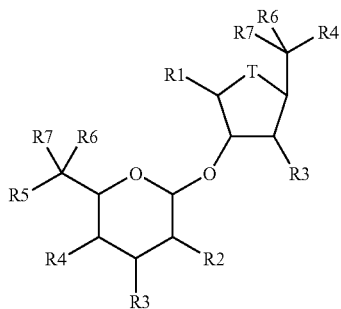
IIg

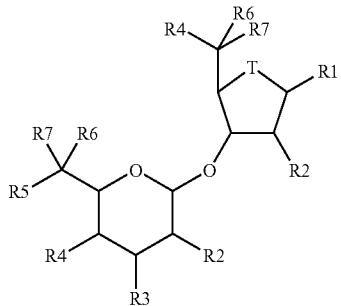
IIh

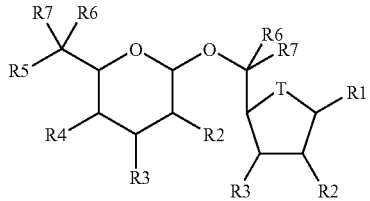
IIi

Another preferred embodiment of the first aspect provides for compounds of formula I in which In group A, T is oxygen, group A is a pyranose ring, The linker, d-L-e, forms an amide linkage in which R6 and R7 of A is a C=O, R5 is d which is a covalent bond, L is absent, and any of R1, R2, R3, R4, R5 on B is e which is

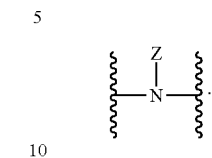

Importantly, The R groups on each ring may be selected independently from each other. For example, R2 on ring A may be different from R2 on ring B.

Exemplary Structure of this Embodiment Include but are not Limited to:

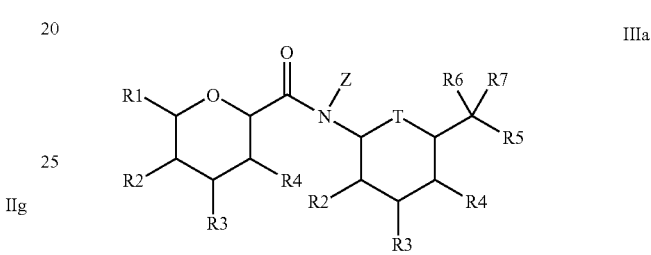
IIIa

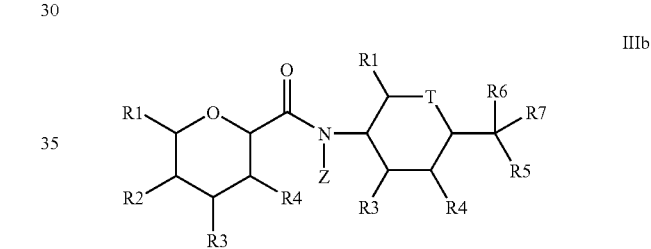
IIIb

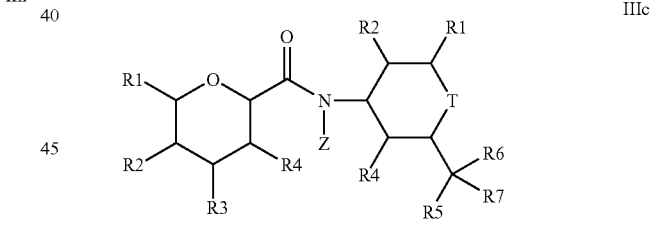
IIIc

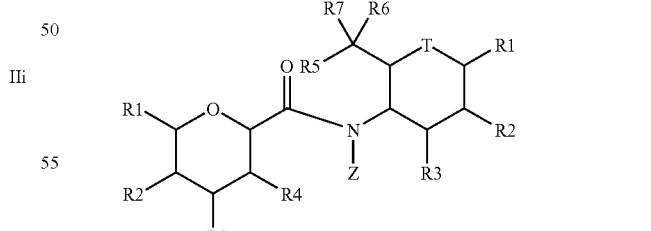
IIId

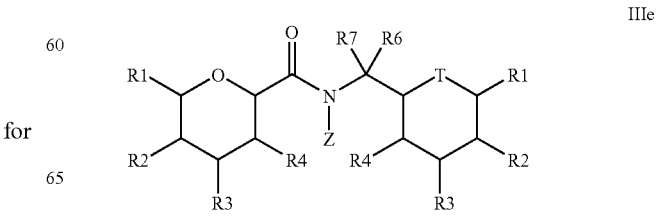
IIIe

IIIf
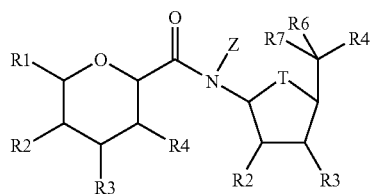

IIIg
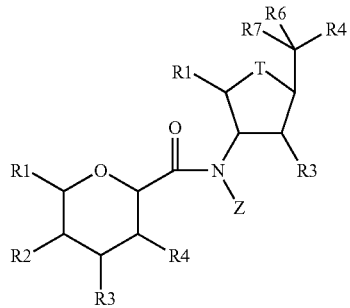

IIIh
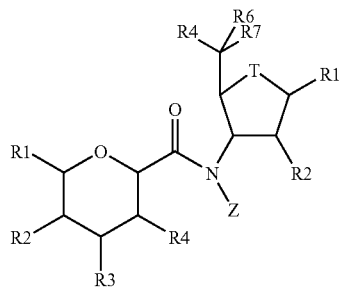

IIIi
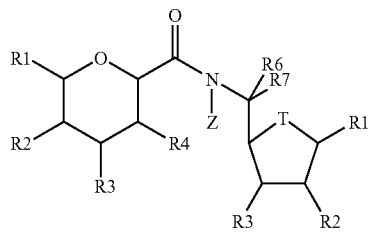

Another preferred embodiment of the first aspect provides for compounds of formula I in which
- in group A, T is oxygen,
- both groups A and B are pyranose rings,
- The linkage, d-L-e, is an ether type linkage in which any of R1 to R5 in group A and group B is d and e respectively and is

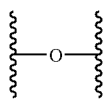

and L must be present.

Importantly, The R groups on each ring may be selected independently from each other. For example, R2 on ring A may be different from R2 on ring B.

Exemplary Structure of this Embodiment Include but are not Limited to:

IVa
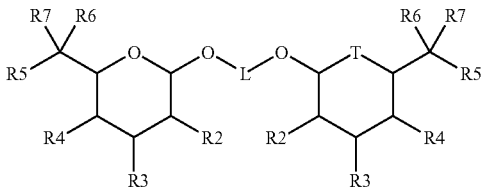

IVb
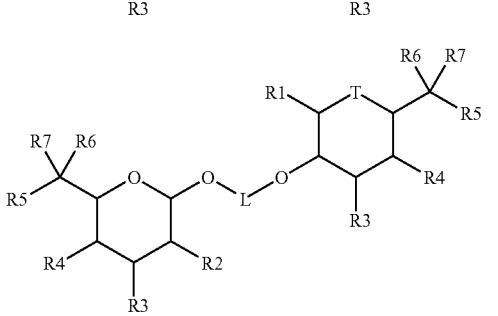

IVc
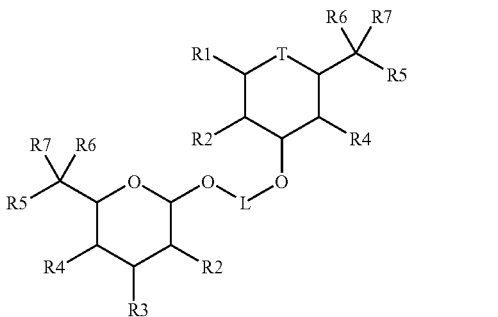

IVd
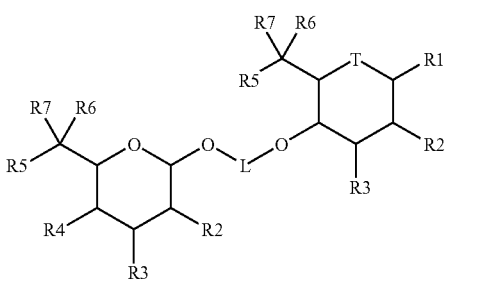

IVe
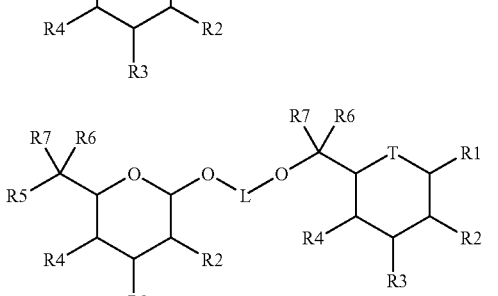

IVf
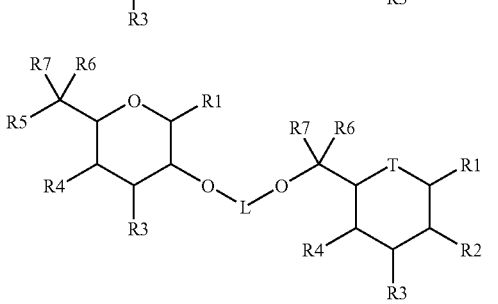

-continued
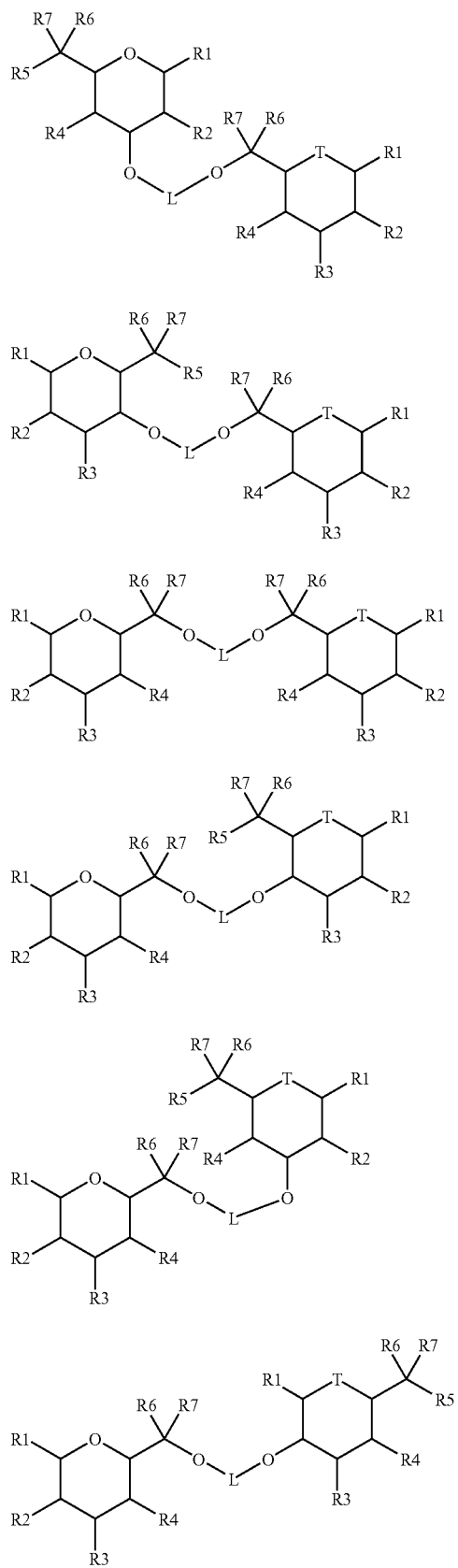
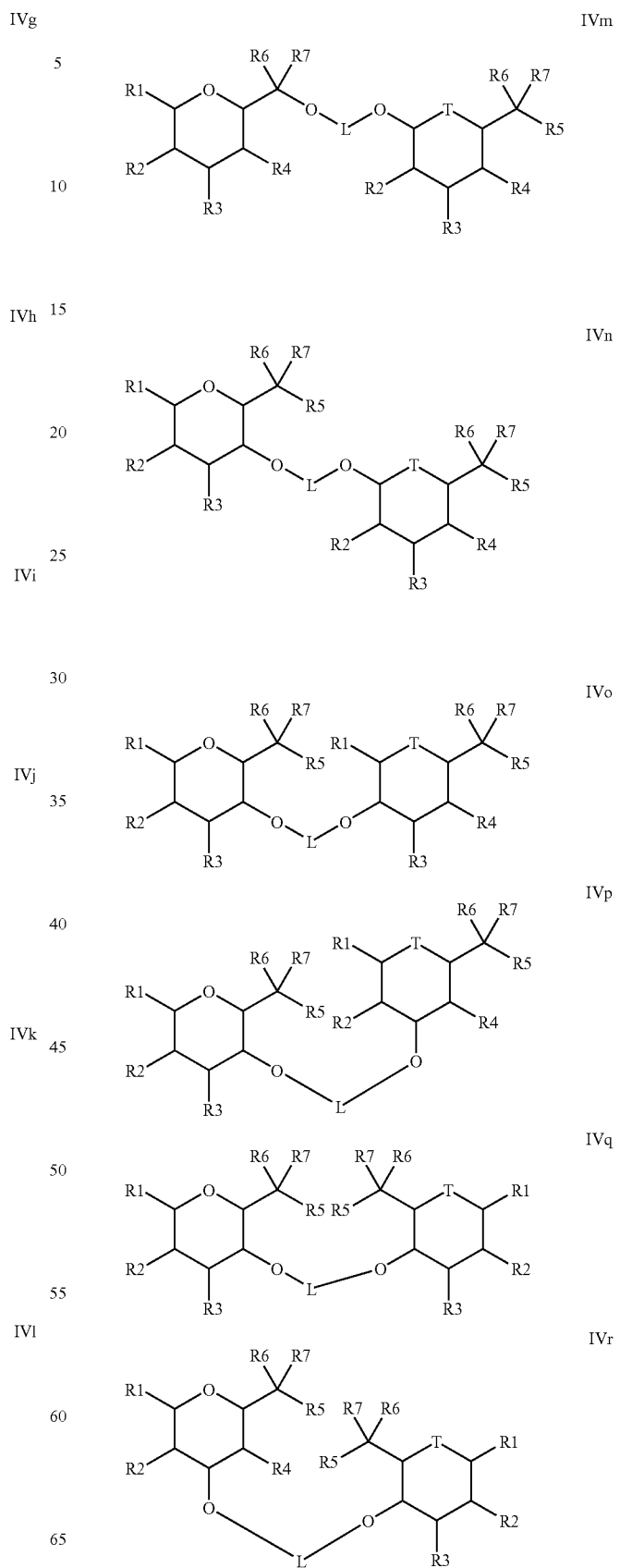

-continued

IVs 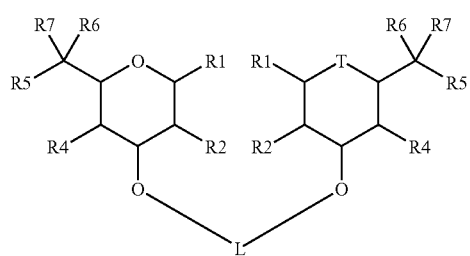

IVt 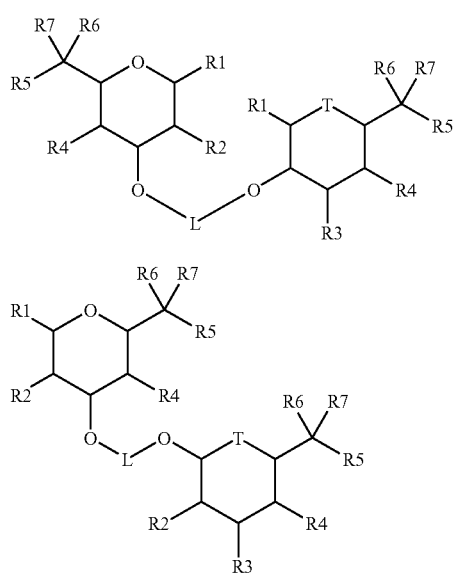

IVu

IVv

IVw 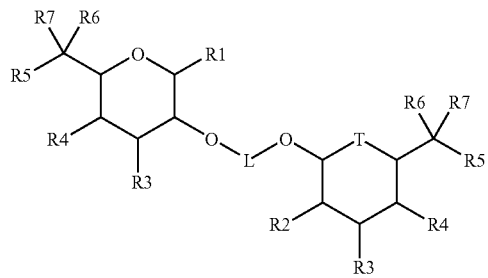

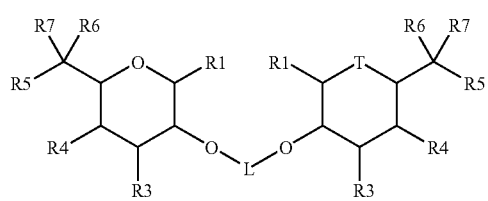

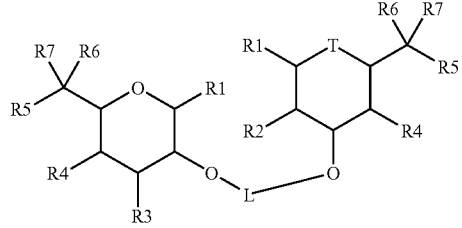

-continued

IVy 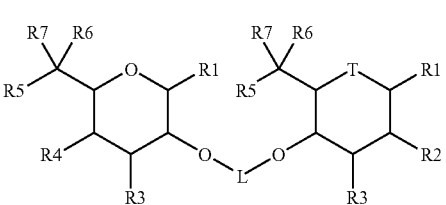

Another preferred embodiment of the first aspect provides for compounds of formula I in which In group A, T is oxygen, The linkage, d-L-e, is a linkage in which R1 in group A is d, which is chosen from: a covalent bond;

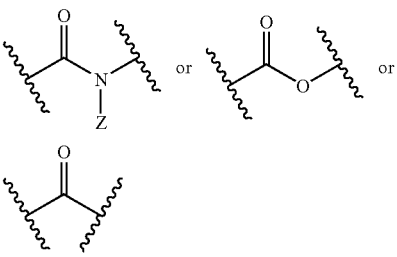

L must be present;

and e is

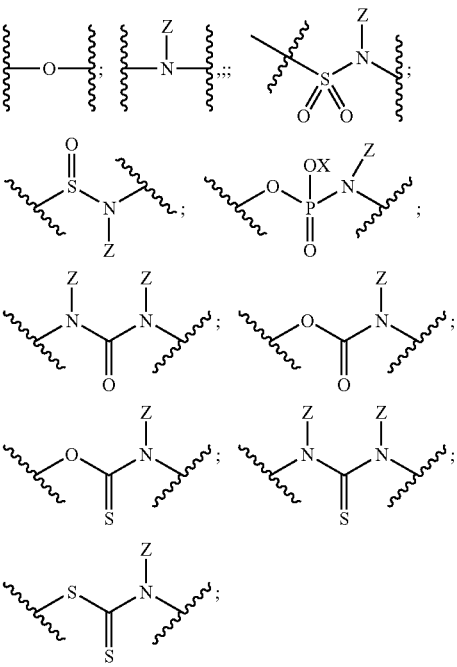

Importantly, The R groups on each ring may be selected independently from each other. For example, R2 on ring A may be different from R2 on ring B.

Exemplary Structure of this Embodiment Include but are not Limited to:

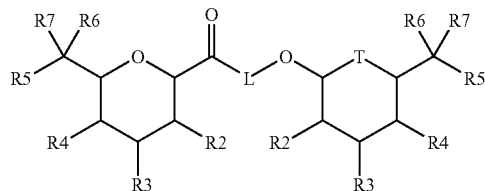
Va

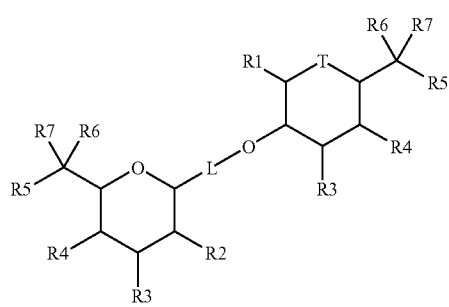
Vb

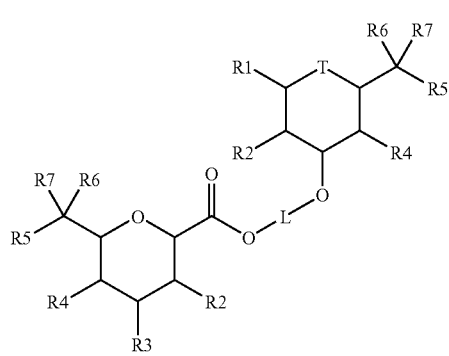
Vc

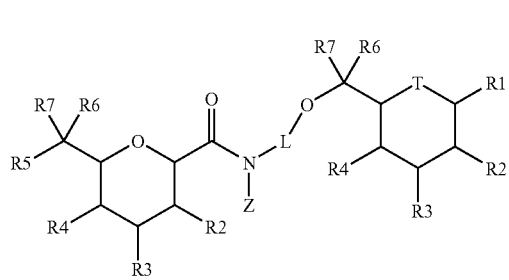
Vd

Another preferred embodiment of the first aspect provides for compounds of formula I in which
In group A, T is oxygen,
The linkage, d-L-e, is a linkage in which R1 in group A is d, R1 in group B is e, and both d and e are independently chosen from: a covalent bond;

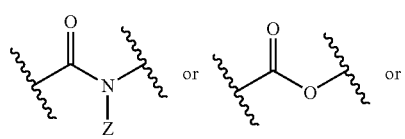 or 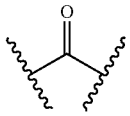 or

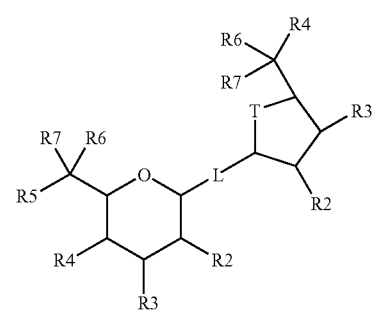

L must be present;
Importantly, The R groups on each ring may be selected independently from each other. For example, R2 on ring A may be different from R2 on ring B.

Exemplary Structures of this Embodiment Include but are not Limited to:

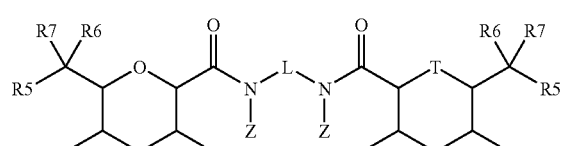
VIa

VIb

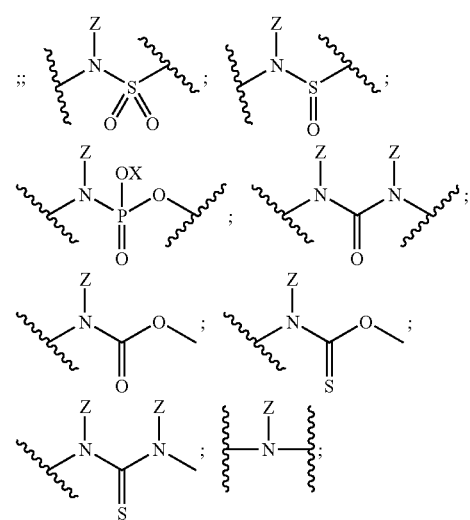

Another preferred embodiment of the first aspect provides for compounds of formula I in which
In group A, T is oxygen,
The linker, d-L-e, is a linkage in which any R group R1 to R5 in group A may be d and is selected from -continued

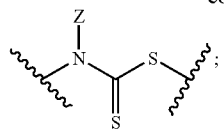

And any R group R1 to R5 in group B may be e and e is

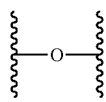

L must be present.

Importantly, The R groups on each ring may be selected independently from each other. For example, R2 on ring A may be different from R2 on ring B.

Exemplary structures of this embodiment include but are not limited to the list below.

VIIa

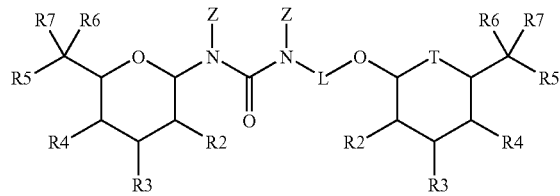

VIIb

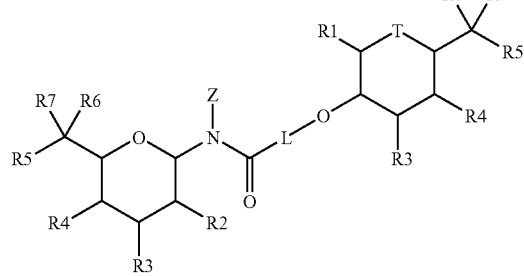

VIIc

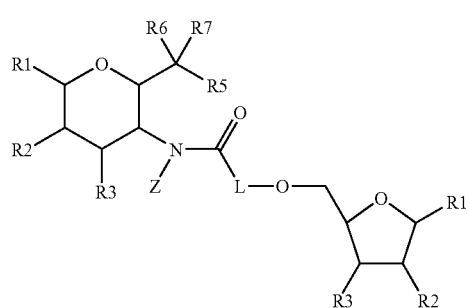

-continued

VIId

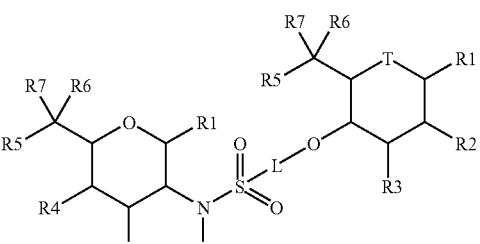

Another preferred embodiment of the first aspect provides for compounds of formula I in which In group A, T is oxygen, The linkage, d-L-e, is a linkage in which any R group R1 to R5 in groups A and B may be d and e respectively and d and e are independently selected from

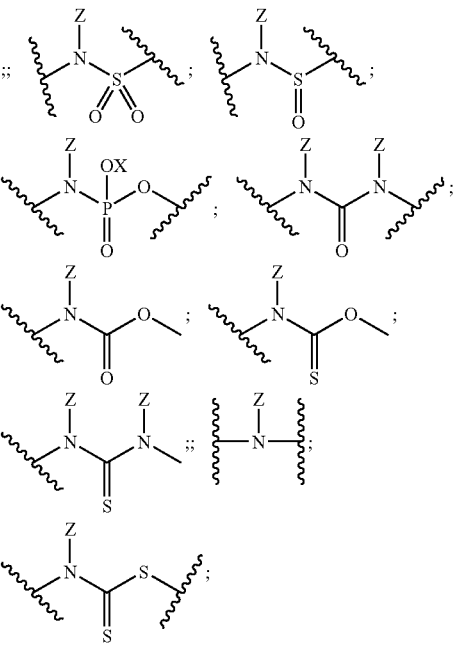

L must be present.

Importantly, The R groups on each ring may be selected independently from each other. For example, R2 on ring A may be different from R2 on ring B.

Exemplary structures of this embodiment include but are not limited to the list below.

VIIIa

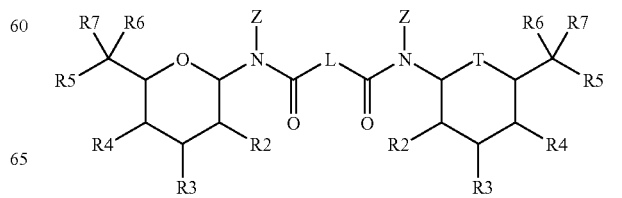

-continued

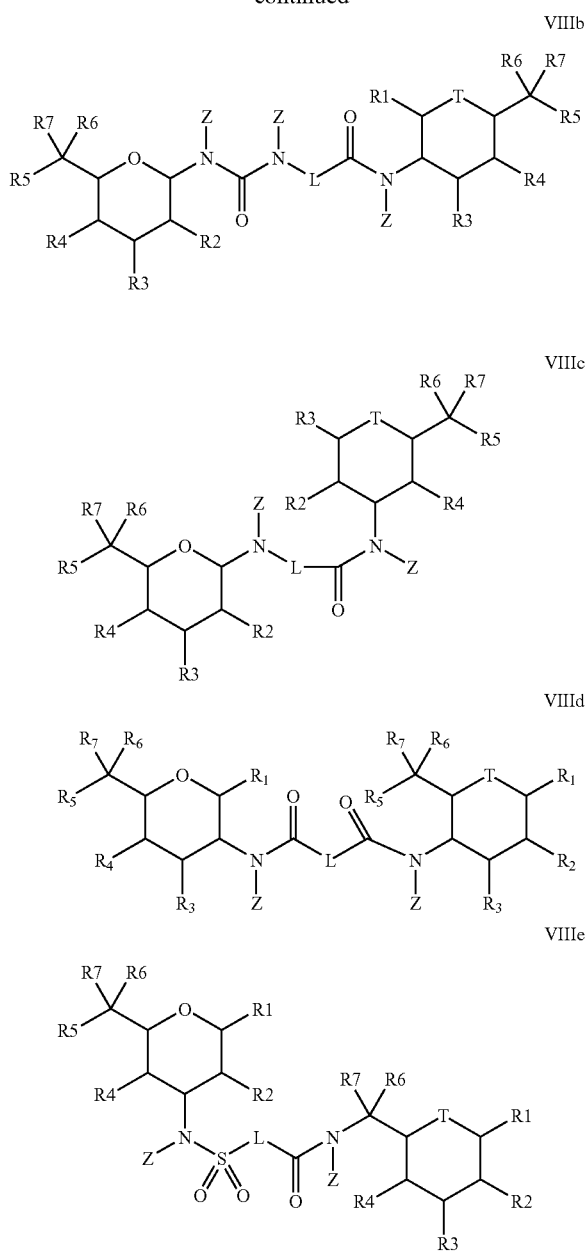

In a second aspect, the invention provides for a method of synthesis of compounds of formula I comprising the step of reacting two appropriately substituted and protected monosaccharide compounds A and B in solution.

In a third aspect, the invention provides for a method of combinatorial synthesis of compounds of the formula I comprising the step of immobilizing a compound of group B onto a support through any of the functionalized positions R1 to R5. Said support may be soluble or insoluble. Non-limiting examples of insoluble supports include derivatised polystyrene, tentagel, wang resin, MBHA resin, aminomethylpolystyrene, rink amide resin etc. Non-limiting examples of soluble supports include DOX-mpeg, polyethylene glycol etc.

Compounds of the invention are useful in screening for biological activity.

For the purposes of this specification it will be clearly understood that the word "comprising" means "including but not limited to", and that the word "comprises" has a corresponding meaning.

General Method 1: Urea Formation

To the diamine (1.05 mmol) dissolved in N,N-dimethylformamide (11 mL), was added isocyanate (1.99 mmol), and the solution stirred for 2.5 h. Toluene (20 mL) was added and all solvent removed to leave an oil. This procedure was repeated twice more. This residue was then triturated with ether and the resulting solid filtered to afford the product.

General Method 2: Transesterification

To a solution of the sugar (16.2 mmol) in a 1:1 mixture of methanol/dichloromethane (110 mL) was added sodium methoxide (6.5 mmol) and the whole stirred under nitrogen for 2 h. Amberlite IR 120 $H^+$ was added until pH 5 was reached. The resin was filtered off and washed several times with methanol and the combined filtrates were then concentrated to dryness to leave a residue. The residue was either triturated with ether or purified by column chromatography to give the desired product.

General Method 3: Azide Reduction

To a solution of the azido compound (0.30 mmol) in 4:1 N,N,-dimethylformamide/methanol (5 mL) was added a solution of ammonium chloride (1.50 mmol) in water (0.5 mL). Activated zinc dust (8.98 mmol) was then added and the suspension stirred for 40 min. A second addition of ammonium chloride (0.50 mmol) in water (0.25 mL) and zinc dust (1.5 mmol) was made and the suspension stirred for a further 40 min. After this time chloroform (50 mL) was added and the suspension filtered through celite and washed with chloroform/N,N,-dimethylformamide (1:1). These combined filtrates were then washed with brine, dried ($MgSO_4$), and all solvent removed in vacuo to typically leave solid.

General Method 4: HBTU Coupling

To a solution of the acid (0.05 mmol) and HBTU (0.05 mmol) in dry N, N,-dimethylformamide (0.2 mL) was added diisoproplyethylamine (0.03 mL, 0.17 mmol) and the whole stirred for 10 min. A solution of the sugar amine (0.04 mmol) in dry N,N,-dimethylformamide (0.3 mL) was then added and the whole stirred for 16 h. Chloroform (15 mL) was then added and washed with water, 10% citric acid, saturated sodium hydrogen carbonate, brine, dried ($MgSO_4$), and the solvents removed in vacuo to leave an oil. The crude was typically carried through to the next step without further purification.

General Method 5: Global Deprotection for Formation of the Final Product-1.

The sugar (0.04 mmol) was dissolved in a solution (3 mL) of 93% dry dichloromethane, 5% triethylsilane, 2% trifluoroacetic acid and the reaction stirred at room temperature for 2 hours. The solvents were then removed in vacuo and the solution then freeze-dried to leave a white solid. This solid was then purified by prep HPLC.

General Method 6: Global Deprotection for Formation of the Final Product-2.

The sugar (0.0016 mmol) was dissolved in a solution (0.1 mL) of 83% dry dichloromethane, 15% p-thiocresol, 2% trifluoroacetic acid and the reaction stirred at room temperature for 0.5 hours. The solvents were then removed in vacuo to give the crude product.

General Method 7: DIC Coupling

To the acid (52 µmol) and HOBT (52 µmol) in dry DCM (1 mL) and dry DMF (1 drop) was added DIC (52 µmol). The solution was stirred for 1 min then added to a solution of amine (35 µmol) in dry DCM (1 mL). The reaction mixture was stirred at room temperature for 1 h then diluted with DCM, washed with 10% citric acid, saturated hydrogen carbonate, brine, dried over $MgSO_4$ and the solvents removed in vacuo.

General Method 8: Ester Hydrolysis

To crude product 4 in dioxane (0.6 mL) was added 1M aq. KOH (0.6 mL). The reaction mixture was stirred at room temperature for 1 h then concentrated in vacuo. The residue was dissolved in $CH_3CN$ (2 mL) and DCM (0.5 mL) and stirred with Amberlite for 1 h. The solution was filtered and concentrated in vacuo to yield a residue which was subsequently purified by prep HPLC.

General Method 9: Fmoc Cleavage Followed by DIC Coupling

Fmoc protected amino compound (~50 µmol) was dissolved in acetonitrile (2.4 mL) and piperidine (60 µL, 0.60 µmol) was added. The mixture was stirred over night, the solvents evaporated in vacuo and the residue azeotroped with toluene to afford a residue. The residue was taken up in dry dichloromethane (2 mL) and a solution of octanoic acid (12 µL, 75 µmol) and DIC (12 µL, 75 µmol) in dry dichloromethane (2 mL) (stirred for 5 min at room temperature prior to addition) was added. Stirring was continued for 1 h and the mixture was diluted with dichloromethane (50 mL), washed with 10% citric acid, satd. sodium bicarbonate solution, filtered over a pad of cotton, and the solvents removed in vacuo to afford the product as a crude mixture.

General Method 10: Amine Deprotection

The fully protected block [2 mmol] was suspended in butanol (15 ml) and ethylene diamine (15 ml) and the mixture heated at reflux for 20 h. The solvents were evaporated, the residue taken up in chloroform, washed with dilute brine, dried ($MgSO_4$) and evaporated. The compound was loaded onto a pad of silica with chloroform and eluted with 9% methanol in chloroform to yield the pure diamine quantitatively.

General Method II: Diamine Coupling

The diamine (17 mg, 0.023 mmol) was dissolved in dry chloroform (0.5 ml), DIPEA (3 mg, 4 µl, 1 equiv) added and the solution cooled to –78° C. A solution of FMOC-Cl (4.2 mg, 0.7 equiv) in chloroform (0.2 ml) was added dropwise and allowed to warm to rt slowly before stirring for 16 h. The mixture was partitioned between chloroform and water, the organic layer washed with $NaHCO_3$, brine, dried ($MgSO_4$) and evaporated to dryness. This gave the monoprotected amine as the major product.

General Method 12: Thiourea Formation

To a solution of the sugar (0.48 mmol) in N,N-dimethylformamide (4.8 mL), was added 4-fluorophenylisothiocyanate (0.48 mmol), and the solution stirred at room temperature for 4 h. Toluene (5 mL) was added and all solvent removed to leave an oil.

General Method 13: CBz Formation

To a solution of the sugar (0.48 mmol) in chloroform (4.8 mL), was added diisopropylethylamine (0.52 mmol). After 5 minutes benzyl chloroformate (0.52 mmol) was added and the solution stirred at room temperature for 2 h. Chloroform (5 mL) was then added and washed with water, 10% citric acid, saturated sodium hydrogen carbonate, brine, dried ($MgSO_4$), and the solvents removed in vacuo to leave an oil.

General Method 14: Sulphonamide Formation

To a solution of the sugar amine (0.0267 mmol) and diisopropylethylamine (0.014 ml, 0.08 mmol) in dry dichloromethane (0.25 mL), was added p-toluenesulfonyl chloride (10.2 mg, 0.054 mmol) and the solution stirred for 72 hrs. The reaction mixture was diluted with dry dichloromethane (2 mL), washed with water (2 ml), dried ($MgSO_4$), and the solvents removed in vacuo to afford the product as a crude mixture.

General Method 15: Acylation with Acetic Anhydride

To a solution of the sugar amine (0.04 mmol) and diisopropylethylamine (0.02 ml, 0.12 mmol) in dry dichloromethane (0.4 mL) was added dropwise acetic anhydride (0.015 mL, 0.12 mmol) and the solution stirred for 1. h. The solution was concentrated in vacuo to yield the crude product.

General Method 16: Fmoc Cleavage

Fmoc protected amino compound (0.48 mmol) was dissolved in chloroform (4 mL) and piperidine (1 ml). The mixture was stirred for 1 hr, evaporarted to dryness. The residue was taken up in acetonitrile (4 ml) and the solid was filtered off and the filter cake washed with acetonitrile (1 ml). The acetonitrile solutions were combined and evaporated to dryness. The residue was purified by column chromatography (dichloromethane:methanol 20:1) to afford the desired product.

General Method 17: Hydrolysis of Triflouroacetate Ester and Purification of the Final Products.

The sugar (0.04 mmol) was dissolved in a solution of methanol (2 mL) and concentrated aqueous ammonium hydroxide (2 ml); the reaction stirred at room temperature for 2 hours. The solvents were then removed in vacuo and the solution then freeze-dried to leave a white solid. This solid was then purified by prep HPLC.

EXAMPLE 1
Preparation of a Compound with a Glycosidic Linkage as Described by Compounds of Formula II
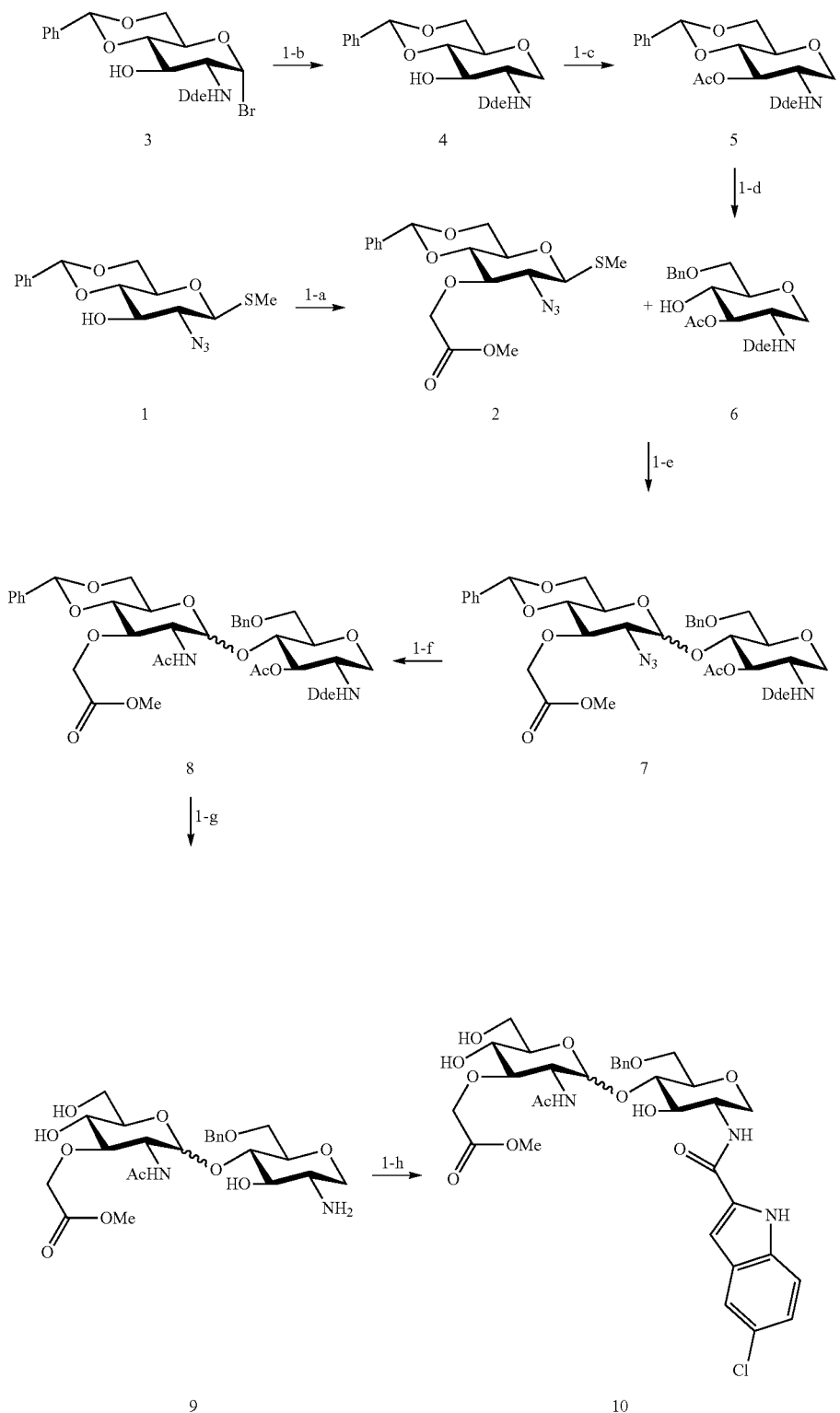

Conditions: (1-a) Methyl bromoacetate, NaH, DMF, 80%; (1-b) Bu₃, 75%; (1-c) Ac₂O, Pyridine, 95%; (1-d) NaCNBH₃; (1-e) MeOTf, DCM, 70%; (1-f) (i) dithiothreitol, (ii) Ac₂O, Pyridine, 80% overall; (1-g) (i) NaOMe/MeOH, (ii) TFA, (iii) NH₃.H₂O; (1-h) (i) 4-chloroindole-2-carboxylate, HBTU, DMF, DIPEA, (ii) NaOH.
EXAMPLE 2
Preparation of a Compound with an Amide Linkage as Described by Compounds of Formula III
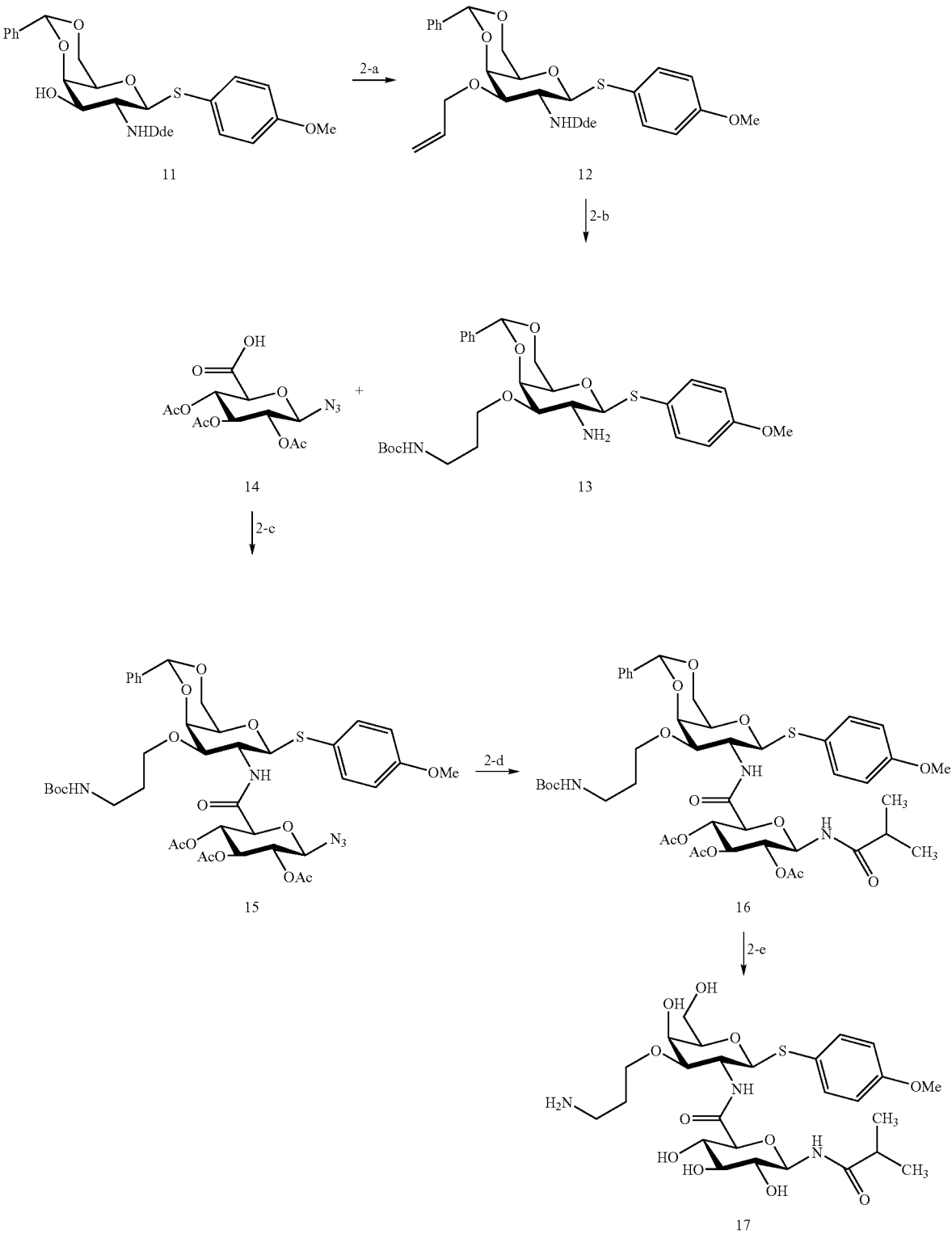

Conditions: (2-a) Allyl-Br, DMF, NaH, 85%; (2-b) (i) 9-BBN, THF, NaOAc, H$_2$O$_2$, (ii) Ph$_3$P, CBr$_4$, (iii) NaN$_3$, DMF, (iv) DTT, Boc$_2$O, (v) NH$_3$.H$_2$O; (2-c) HBTU, DIPEA, DMF; (2-d) (i) DTT, (ii) HBTU, DIPEA, isobutyric acid; (2-e) (i) NaOMe/MeOH, (ii) TFA.
EXAMPLE 3
Preparation of a Compound with an Ether Linkage as Described by Compounds of Formula IV
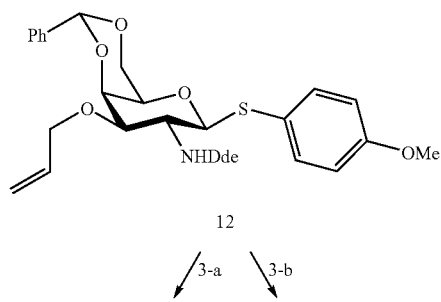
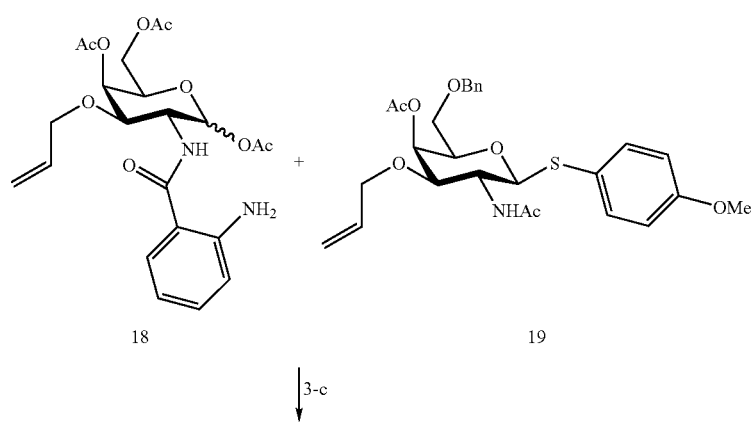
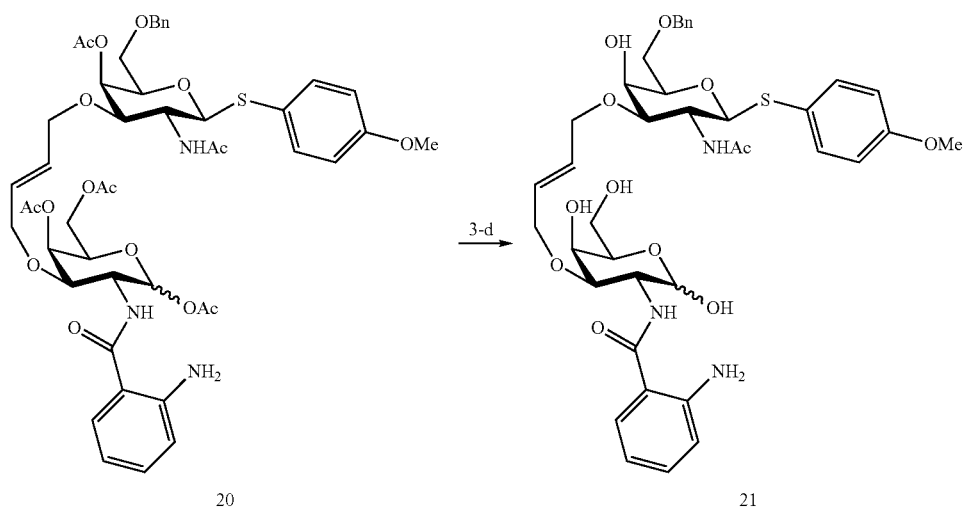

Conditions: (3-a) (i) NaCNBH₃, (ii) NH₃.H₂O, (iii) Ac₂O, pyridine; (3-b) (i) NBS, acetone, (ii) TFA, (iii) Ac₂O, pyridine, (iv) NH₃H₂O, (v) HBTU, DIPEA, 2-aminobenzoic acid; (3-c) grubbs catalyst; (3-d) NaOMe/MeOH.
EXAMPLE 4
Preparation of a Compound with an Ether Linkage as Described by Compounds of Formula IV
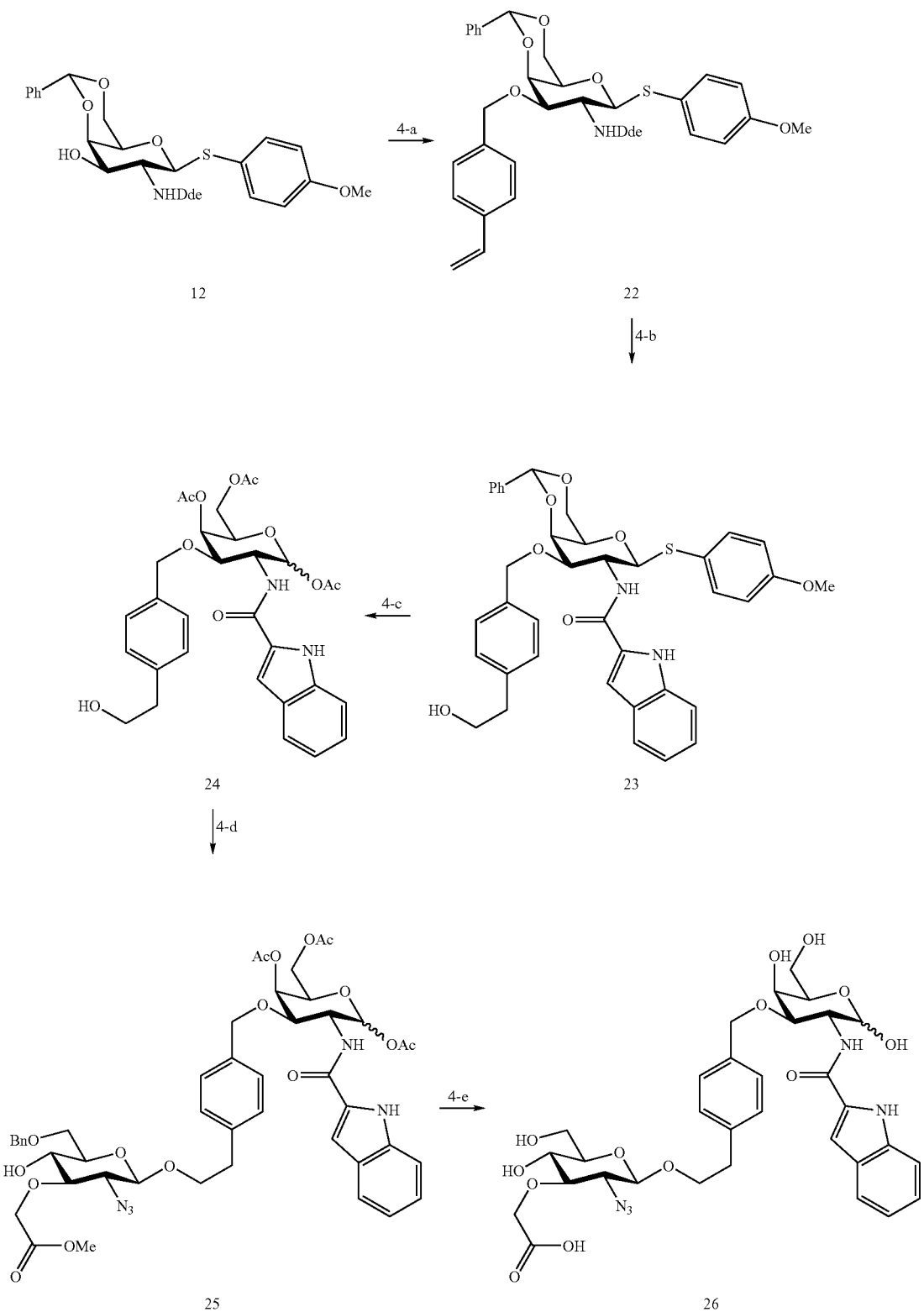

Conditions: (4-a) Vinylbenzyl chloride, NaH, DMF; (4-b) 9-BBN, NaOAc, H₂O₂; (4-c) (1) Chloroacetylchloride, (ii) NBS, acetone, TFA, (iii) Ac₂O, pyridine, (iv) NH₃.H₂O, HBTU, DIPEA, indole-2carboxylate, (vi) thiourea; (4-d) MeOTf, (4-e) (i) NaCNBH₃, (ii) NaOH.
EXAMPLE 5
Preparation of a Compound with an Ether Linkage as Described by Compounds of Formula V
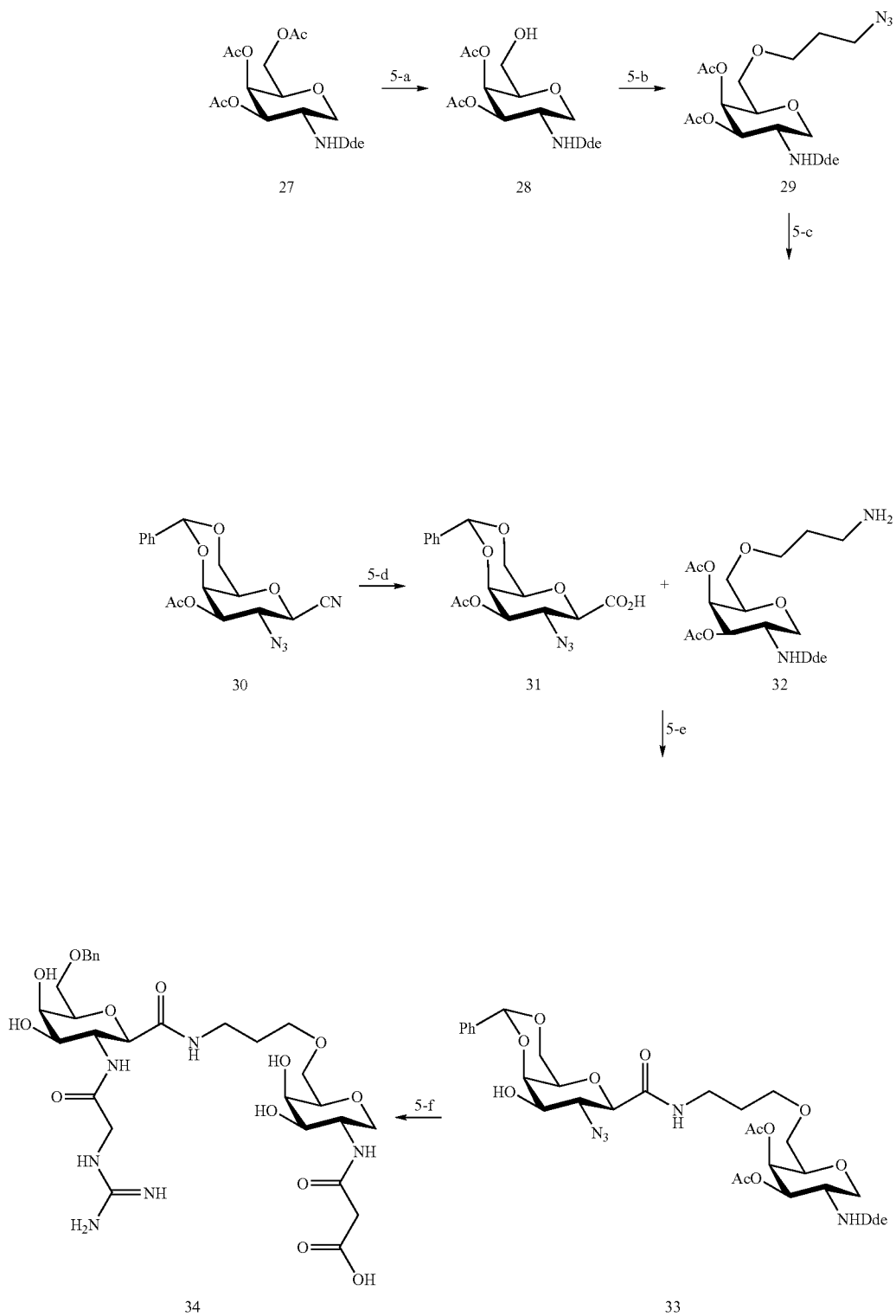

Conditions: (5-a) NaOMe, −40° C.; (5-b) 3-azidopropyl bromide, NaH, DMF; (5-c) DTT; (5-d) NaOH; (5-e) HBTU, DIPEA, DMF; (5-f) (i) DTT, (ii) HBTU, Boc-Glycine, (iii) NaCNBH₃, TFA, (iv) 1H-pyrazole-1-carboxamidine hydrochlorie, (v) NH₃.H₂O, (vi) mono-methyl malonate, DCC, (vii) NaOMe.
EXAMPLE 6
Preparation of a Compound with a Linkage as Described by Compounds of Formula V and VI
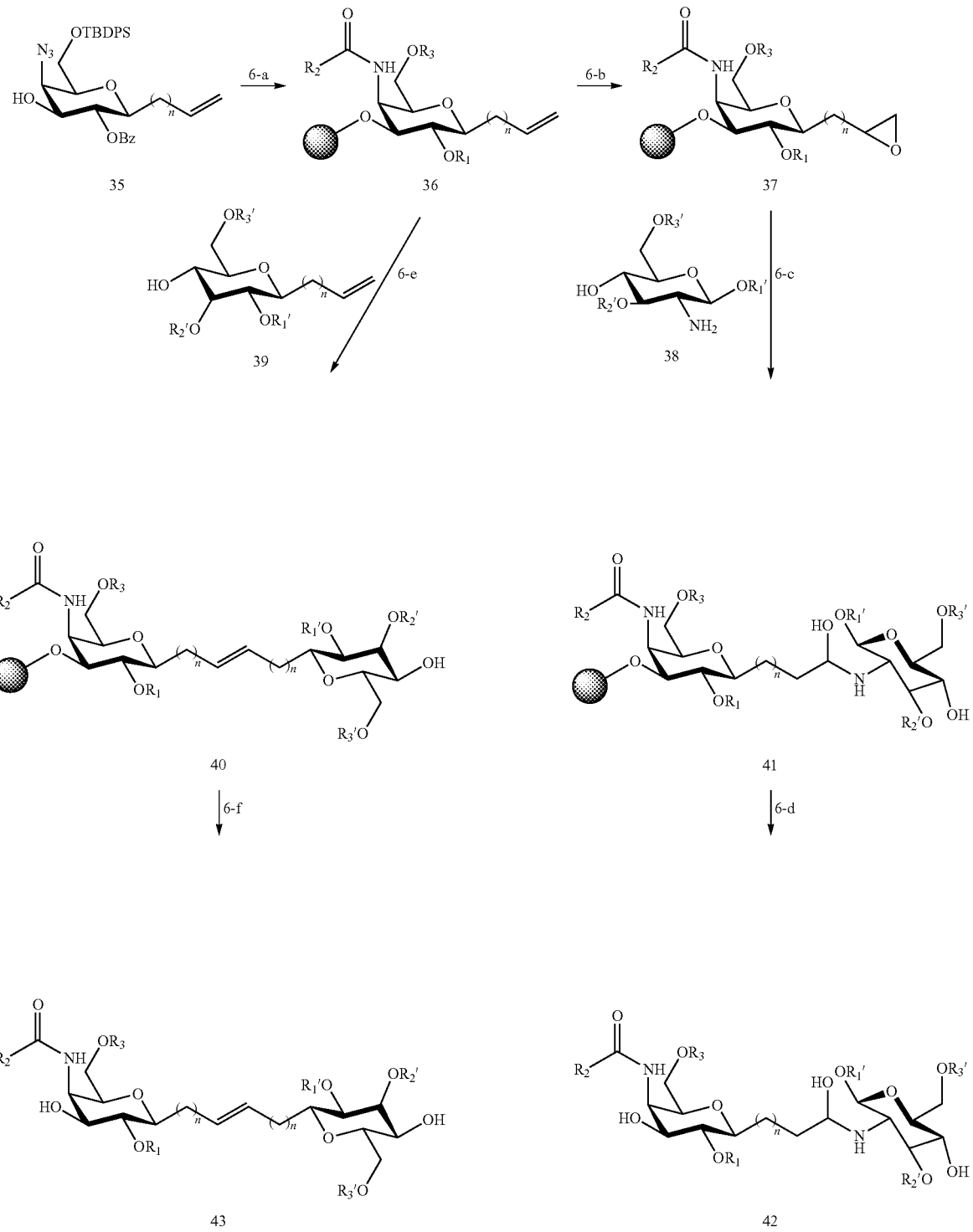

Conditions: (6-a) (i) wang OTCA resin, BF$_3$.Et$_2$O, (ii) NaOMe/MeOH, (iii) R$_1$—Br, base, (iv) TBAF, MeOH, THF, (v) R$_3$—Br, base, (vi) DT, (vii) HBTU, DIPEA, DMF, R$_2$—CO$_2$H; (6-b) m-CPBA; (6-c) amine 38, DMF; (6-d) TFA cleavage; (6-e) grubbs cleavage; (6-f) TFA cleavage.
EXAMPLE 7
Preparation of a Compound with a Linkage as Described by Compounds of Formula VI
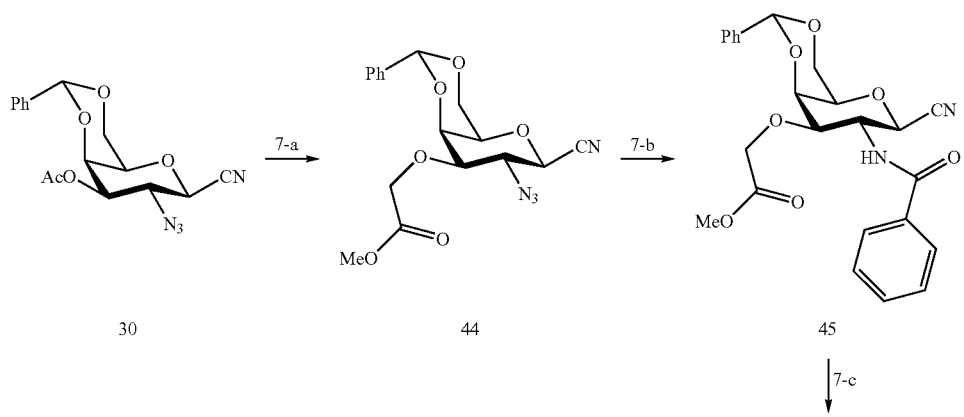
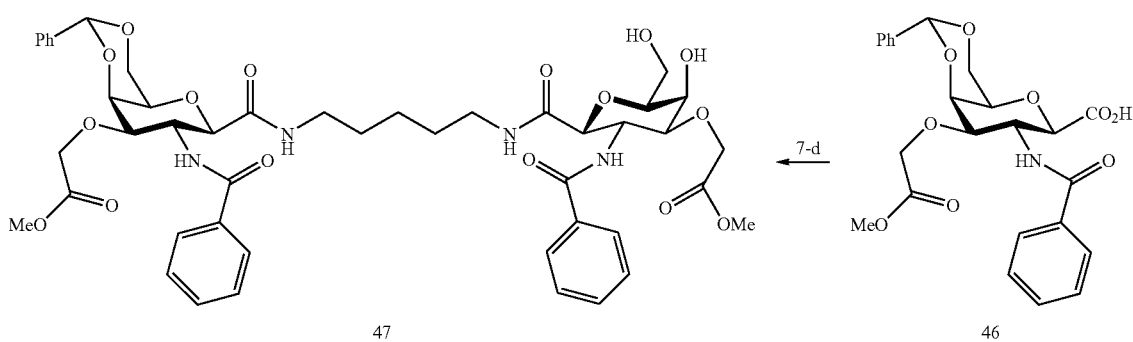

Conditions: (7-a) (i) NaOMe/MeOH, (ii) Methyl bromoacetate, NaH, DMF; (7-b) DTT, benzoylchloride, DMF; (7-c) SP-nitrilase immobilised enzyme, acetonitrile, water; (7-d) (i) HBTU, DIPEA, 1,5-diaminopentane (ii) TFA, acetonitrile, H₂O.
EXAMPLE 8
Preparation of a Compound with a Linkage as Described by Compounds of Formula VII
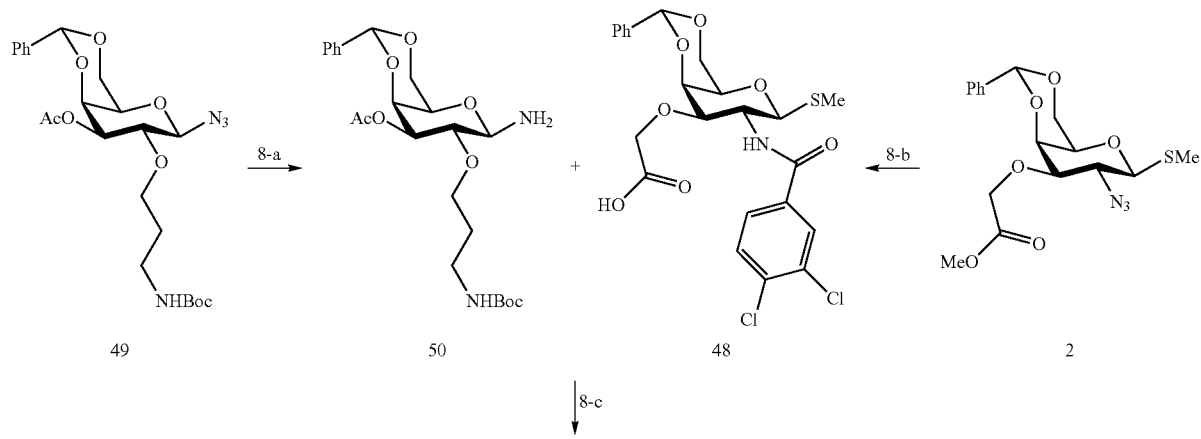
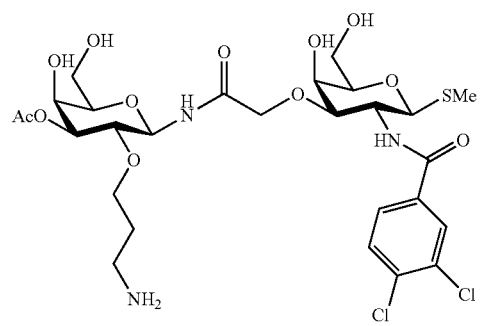

Condition: (8-a) DTT; (8-b) (i) DTT; (ii) 3,4-dichlorobenzoyl chloride, (iii) NaOH; (8-c) (i) HBTU, DIPEA, DMF, (ii) NaOMe/MeOH, (iii) TFA, acetonitrile, water.

EXAMPLE 9

Preparation of a Compound with a Linkage as Described by Compounds of Formula VIII

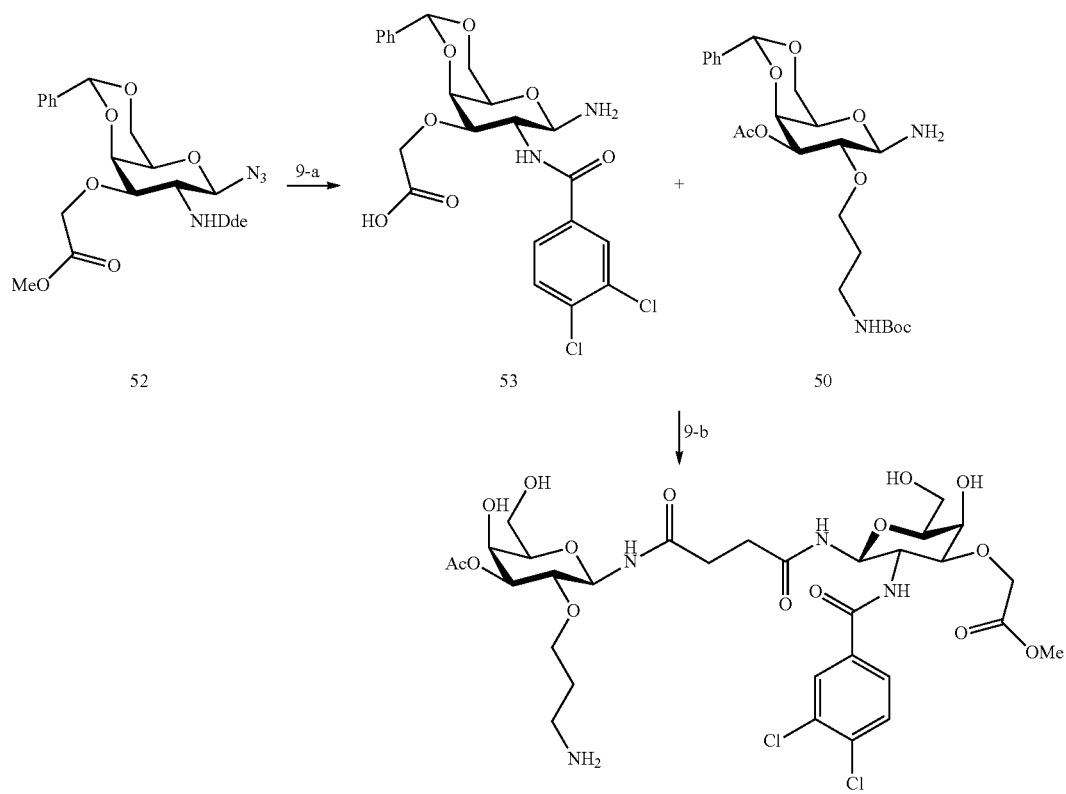

Conditions: (9-a) (i) NH$_3$.H$_2$O, (ii) 3,4-dichlorobenzoyl chloride, (iii) DTT; (9-b) (i) succinic anhydride, (ii) HBTU, DIPEA, (iii) NaOH, (iv) TFA, acetonitrile, water.

EXAMPLE 10

Synthesis of 1,5-Anhydrogalactitol Acceptor

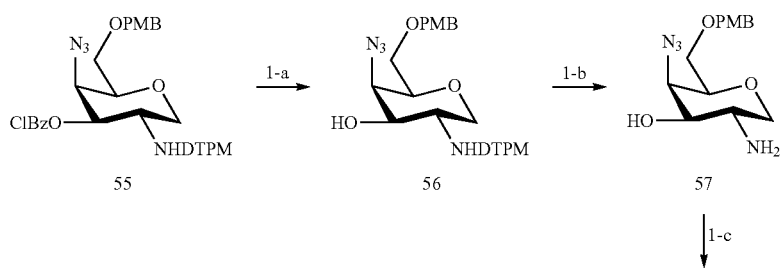

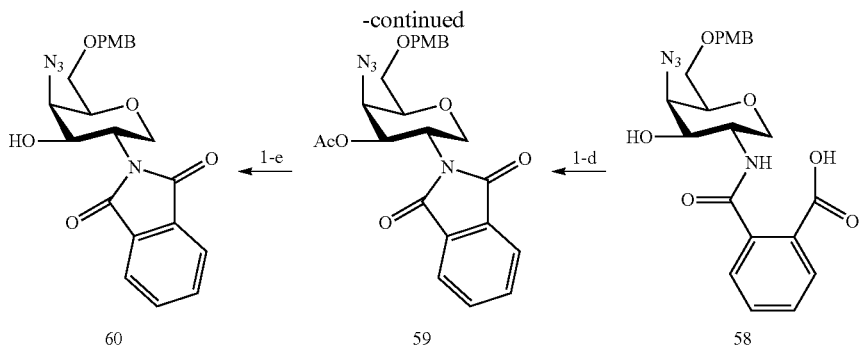

10-a. Synthesis of 1,5-anhydro-4-azido-2,4-dideoxy-2-DTPM-6-O-(4-methoxybenzyl)-D-galactitol (56)

Compound 56 was prepared according to the procedure described in General Method 2, $\delta_H$ (400 MHz; CDCl$_3$) 3.25 (3 H, s), 3.26 (3 H, s), 3.65 (5 H, m), 3.80 (3 H, s), 4.09 (3 H, m), 4.50 (2 H, q, J 9.5 Hz and J 3.6 Hz), 6.89 (2 H, d, J 8.8 Hz), 7.26 (2 H, d, J 8.8 Hz), 8.21 (1 H, d, J 13.6 Hz), and 10.15 (1 H, br t, J 11.4 Hz); LCMS [M+H]$^+$=475.

10-b. Synthesis of 2-amino-1,5-anhydro-4-azido-2,4-dideoxy-6-O-(4-methoxybenzyl)-D-galactitol (57)

To a solution of the sugar 56 (16.0 mmol) in a 3:1 mixture of dry methanol/N, N,-dimethylformamide (120 mL) was added hydrazine monohydrate (86.3 mmol) and the resulting reaction mixture was stirred for 3 h. The resulting precipitate was removed by filtration and the filtrate concentrated in vacuo. The residue was then redissolved in dichloromethane, washed with saturated sodium chloride, dried (MgSO$_4$) and all solvent removed under reduced pressure to leave a solid 57. The solid was used directly in the next step.

10-c. Synthesis of 1,5-anhydro-4-azido-2-(3-carboxybenzyl)-2,4-dideoxy-6-O-(4-methoxybenzyl)-D-galactitol (58)

To a solution of the amine 57 (16.2 mmol) in methanol (55 ml), was added phthalic anhydride (216.2 mmol), and the whole stirred for 2 h. The mixture was then evaporated to dryness under reduced pressure and the residue azeotroped with toluene to leave a cream solid 58.

10-d. Synthesis of 3-O-acetyl-1,5-anhydro-4-azido-2,4-dideoxy-6-O-(4-methoxybenzyl)-2-phthallimido-D-galactitol (59)

The acid 4 (16.3 mol) was suspended in dry pyridine (19 ml), cooled to 0° C., and acetic anhydride (48.7 mmol) added. The suspension was then stirred for 1 h at 0° C. followed by 18 h at room temperature. The solvent was then removed in vacuo and the resulting residue azeotroped with toluene, redissolved in chloroform and washed with water, 10% citric acid, saturated sodium hydrogen carbonate, brine, dried (MgSO$_4$) and the solvent removed in vacuo to leave a yellow solid 59.

10-e. Synthesis of 1,5-Anhydro-4-azido-2,4-dideoxy-6-O-(4-methoxybenzyl)-2-phthallimido-D-galactitol (60)

Compound 60 was prepared according to the procedure described in General Method 2, yield (77% from 55), $\delta_H$ (400 MHz; CDCl$_3$) 3.58 (1 H, dd, J 14.3 Hz and J 7.3 Hz), 3.66-3.74 (1 H, m), 3.82 (3 H, s), 3.82-3.93 (1 H, m), 4.03 (1 H, t, J 11.4 Hz), 4.10 (1 H, d, J 3.7 Hz), 4.42-4.52 (1 H, m), 4.52 (2 H, s), 4.66 (1 H, dd, J 3.7 Hz and J 10.7 Hz), 6.90 (2 H, d, J 8.9 Hz), 7.28 (2 H, d, J 8.9 Hz), 7.74 (2 H, m) and 7.67 (2 H, m); [M+NH$_4$]+=456.

EXAMPLE 11

Synthesis of a Trichloroacetimidate Donor

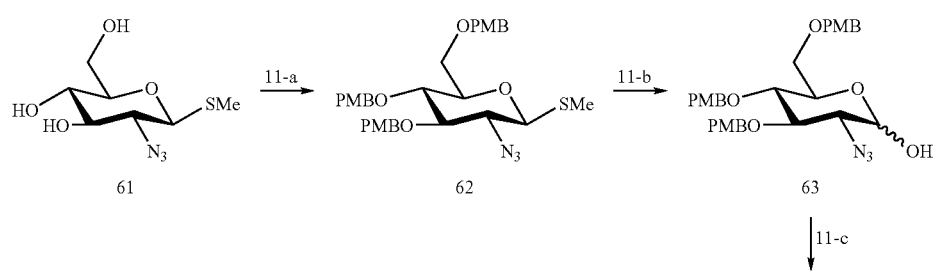

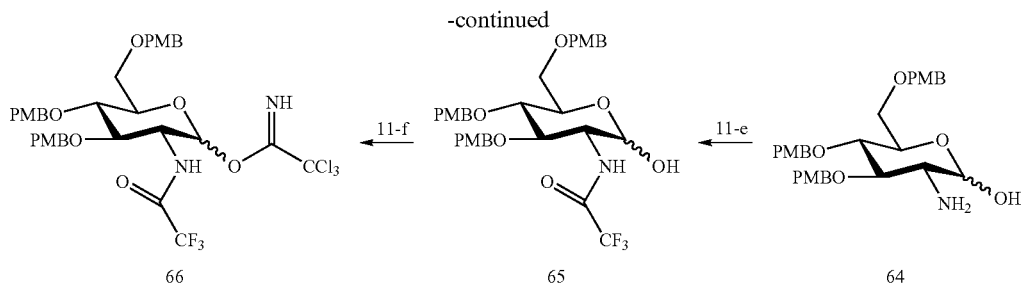

11-a. Thiomethyl 2-azido-2-deoxy-3,4,6-tri-O-(4-methoxybenzyl)-β-D-glucopyranoside (62)

The thioglycoside 61 (21.2 mmol) was added in portions to a suspension of sodium hydride (84.8 mmol) in DMF (106 ml) at 0° C. After 20 min, the mixture was allowed to return to room temperature and stirred for 30 min prior to recooling to 0° C. To the suspension was then added 4-methoxybenzyl chloride (11.5 ml) over 20 mins. The reaction mixture was then allowed to return to room temperature and stirred for 16 h. The resulting solution was cooled to 0° C. and quenched with ammonium chloride solution. The reaction mixture was partitioned between water and chloroform, and the organic layer subsequently washed with brine, dried (MgSO$_4$) and evaporated. Residue was purified by column chromatography to give the desired product 62 as a solid in quantitative yield, $\delta_H$ (400 MHz; CDCl$_3$) 2.22 (3 H, s), 3.32-3.48 (3 H, m), 3.54-3.70 (3 H, m), 3.80 (3 H, s), 3.81 (3 H, s), 3.82 (3 H, s), 4.17 (1 H, d, J 9.5 Hz), 4.46 (1 H, d, J 9.3 Hz), 4.49 (1 H, d, J 10.3 Hz), 4.55 (1 H, d, J 11.6 Hz), 4.63 (1 H, d, J 5.2 Hz), 4.82 (2 H, s), 6.75-6.95 (6 H, m), 7.09 (2 H, d, J 8.9 Hz), 7.24 (2 H, d, J 8.9 Hz) and 7.30 (2 H, d, J 10.3 Hz); LCMS [M+Na]$^+$= 618.2.

11-b. Synthesis of 2-Azido-2-deoxy-3,4,6-tri-O-(4-methoxybenzyl)-D-glucopyranose (63)

To a solution of thioglycoside 62 (112.9 mmol) in acetone (450 mL) at 0° C., shielded from light, was added water (277.8 mmol), N-iodosuccinimide (134.9 mmol), followed by TMSOTf (11.2 mmol), and the solution stirred for 90 min. Chloroform (400 mL) was added and the chloroform layer separated and washed with saturated sodium hydrogen carbonate solution, saturated Na$_2$S$_2$O$_3$ solution, brine, dried (MgSO$_4$) and concentrated in vacuo to leave a solid. The solid was triturated with ether to give the desired product 63 as a cream coloured solid (98%), $\delta_H$(400 MHz; CDCl$_3$) 3.42 (1 H, dd, J 3.0 Hz and J 10.0 Hz), 3.52-3.66 (3 H, m), 3.78 (3 H, s), 3.81 (3 H, s), 3.82 (3 H, s), 3.97 (1 H, t, J 9.8 Hz), 4.03 (1 H, dq, J 2 Hz, J 4.9 Hz and J 9.8 Hz), 4.42 (2 H, t, J 10.3 Hz), 4.53 (1 H, d, J 11.8 Hz), 4.62 (1 H, br d, J 4.9 Hz), 4.73 (1 H, d, J 10.6 Hz), 4.82 (2 H, s), 6.81-6.93 (6 H, m), 7.05 (2 H, d, J 8.8 Hz), 7.24 (2 H, d, J 11.7 Hz) and 7.30 (2 H, d, J 8.8 Hz); LCMS [M+Na]$^+$=588.3.

11-c. Synthesis of 2-Amino-2-deoxy-3,4,6-tri-O-(4-methoxybenzyl)-D-glucopyranose (64)

To a solution of the azide 63 (110.2 mmol) in dry DMF (275 mL) was added dithiothreitol (220.4 mmol). The reaction mixture was then degassed with a stream of nitrogen, cooled to 0 C, and triethylamine (220.4 mmol) added. The solution was then allowed to return to room temperature and subsequently stirred for 24 h. The solution was then diluted with ethyl acetate and washed with water, brine, dried (MgSO$_4$), the solvents removed in vacuo, and resulting residue treated with diethyl ether (~250 mL) to give the desired product 64 as a white solid (69%), LCMS [M+H]$^+$=540.25.

11-d. Synthesis of 2-Deoxy-3,4,6-tri-O-(4-methoxybenzyl)-2-trifluoroacetamido-D-glucopyranose (65)

To a solution of the amine 64 (75.6 mmol) in dry chloroform (400 ml) at 0° C. was added diisoproplyethylamine (113.4 mmol) and trifluoroacetic acid (16.0 mL, 113.4 mmol). The resulting reaction mixture was then stirred for 30 min after which time the reaction was allowed to return to room temperature and stir for a further 1 h. At this time the reaction was cooled to 0° C. and further diisoproplyethylamine (113.4 mmol) and trifluoroacetic acid (113.4 mmol) added, the reaction was allowed to return to room temperature and stirred for 3 h. The reaction mixture was then poured into dilute sodium hydrogen carbonate and the mixture stirred for 30 min. The solid was washed with water, transferred to a flask and dried by co-evaporation with acetonitrile to give the crude product. Ethyl acetate was then added to the residue and the resulting suspension refluxed for 2 h. Petrol ether (~300 mL) was then added to this, the mixture cooled to room temperature, and the resulting solid filtered and dried under high vacuum to give the desired product 65 as a solid (77%), $\delta_H$(400 MHz; CDCl$_3$) 3.04-3.17 (1 H, m), 3.54-3.60 (2 H, m), 3.61-3.71 (2 H, m), 3.79 (3 H, s), 3.80 (3 H, s), 3.81 (3 H, s), 4.01 [dt, J 3.0 Hz and J 10.4 Hz] and 4.16 [dt, J 3.7 Hz and J 10.1 Hz] (1 H), 4.43 (2 H, t, J 10.4 Hz), 4.50-4.60 (2 H, m), 4.66-4.78 (2 H, m), 5.23 (1 H, d, J 4.0 Hz), 6.11 (1 H, br d, J 2.9 Hz), 6.80-6.90 (6 H, m), 7.06 (2 H, d, J 11.1 Hz), 7.18 (2 H, d, J 12.6 Hz) and 7.24 (2 H, d, J 11.1 Hz); LCMS [M+Na]$^+$= 658.2.

11-f. Formation of Imidate (65)

To a solution of the lactol 11 (8.7 mmol) in tetrahydofuran (540 mL) was added trichloroacetonitrile (172.9 mmol), followed by potassium carbonate (103.9 mmol), and the suspension stirred for 8 days. After 8 days the suspension was filtered through celite, washed with tetrahydrofuran and all the solvent removed in vacuo to leave a brown oil. The oil was then purified by column chromatography (eluent toluene/acetone; 20:1) to give the desired product 12 as a brown semi-solid (60%).

EXAMPLE 12
Synthesis of Disaccharide and Functionalisation
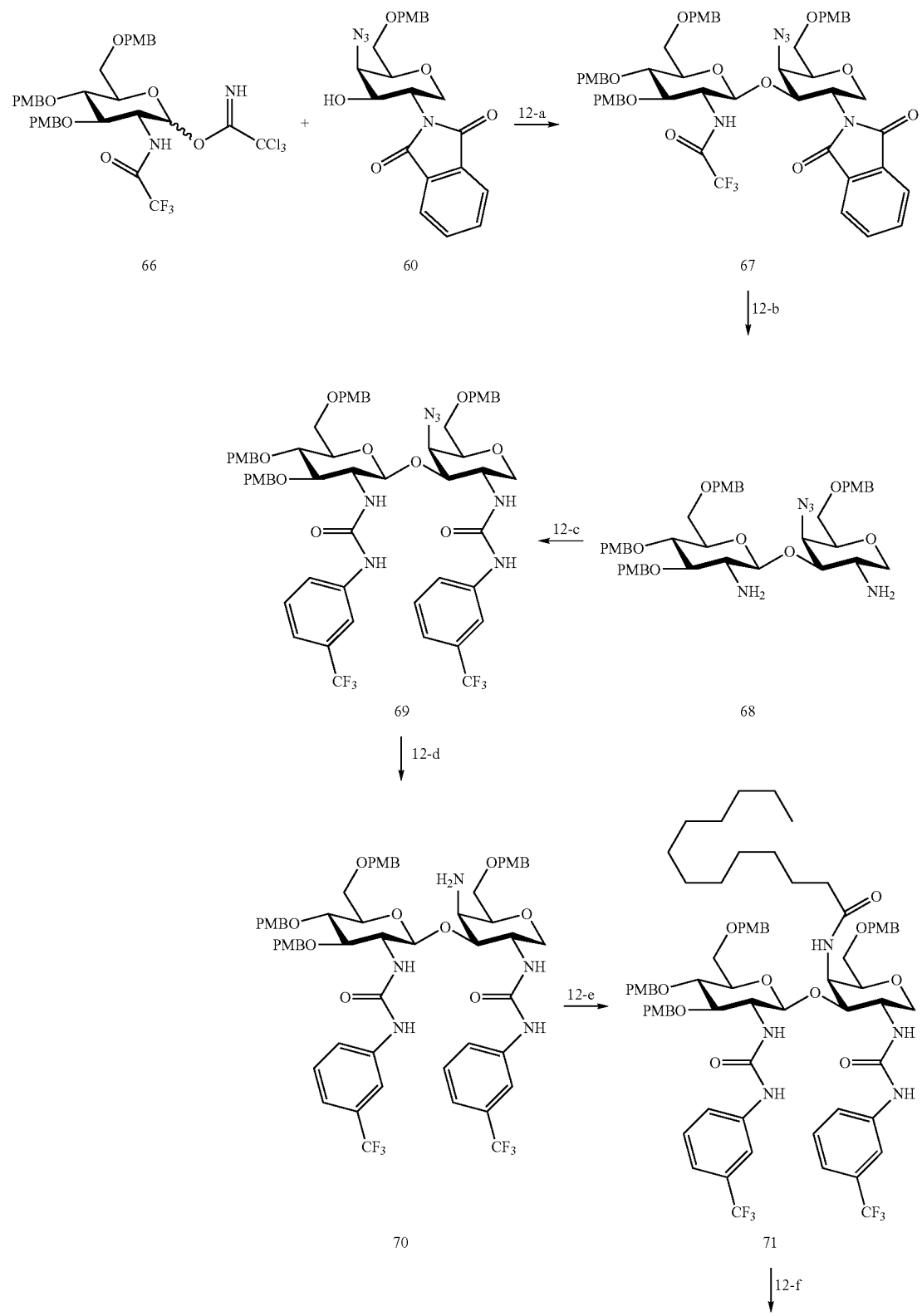

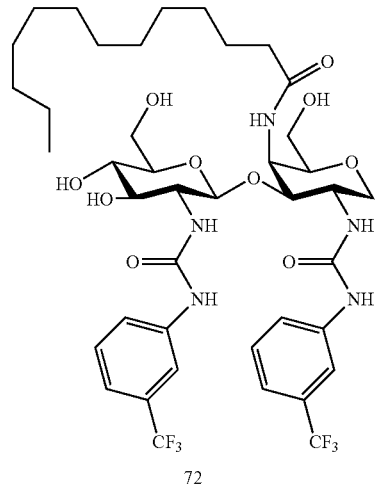

72

12-a. Glycosylation with a Trichloroacetimidate Donor to Afford Disaccharide (67)

To a solution of the acceptor 60 (1.8 mmol) and the donor 66 (2.7 mmol) in dry 1,2-dichloroethane (84 mL) was added 3A acid-washed molecular pellets (4 g) and the resulting mixture stirred for 20 min. To the mixture was then added TMSOTf (1.8 mL of a 0.1M solution in dry 1,2-dichloroethane, 0.18 mmol) and the reaction then stirred for 15 min. After this time triethylamine (6 mL) was added and the suspension filtered, washed with dichloromethane and all solvent removed in vacuo to leave a yellow solid. This resulting solid was triturated with ether and filtered to give the disaccharide 67 as a cream solid (65%), $\delta_H$ (400 MHz; CDCl$_3$) 3.26-3.35 (1 H, m), 3.42-3.66 (5 H, m), 3.68-3.72 (1 H, m), 3.74 (3 H, s), 3.76 (3 H, s), 3.76-3.82 (4 H, m), 3.78 (6 H, s), 3.87-3.96 (1 H, m), 4.32-4.54 (6 H, m), 4.62-4.79 (3 H, m, [4.66, dd, J 3.4 Hz and J 13.3 Hz]), 5.02 (1 H, dd, J 3.8 Hz and J 12.6 Hz), 5.04 (1 H, d, J 10.7 Hz), 6.34 (1 H, d, J 10.3 Hz), 6.76-6.92 (8 H, m), 7.07 (4 H, dd, J 1.6 Hz and J 9.0 Hz), 7.20-7.24 (4 H, m), 7.69-7.74 (2 H, m) and 7.77-7.85 (2 H, m); LCMS [M+H+Na]$^+$=1078.2.

12-b. Amine Deprotection to Afford the Diamino Derivative (68)

The protected disaccharide 67 (0.95 mmol) was suspended in n-butanol/ethylenediamine (1:1, 14 mL) and heated at reflux for 16 h. The solvent was then removed in vacuo, and the residue taken up in chloroform, washed with dilute brine, dried (MgSO$_4$), and solvent removed in vacuo to leave an oil. The oil was purified by column chromatography (eluent 10:1, chloroform/methanol) to give the desired product 68 as a gummy solid [72%, used directly in next step], $\delta_H$ (400 MHz; CDCl$_3$) 2.91 (1 H, dd, J 8.2 and J 10.3 Hz), 2.96-3.08 (1 H, m), 3.21-3.29 (1 H, m), 3.35-3.50 (4 H, m), 3.52-3.68 (5 H, m), 3.74-3.82 (12 H, singlets), 3.91-3.98 (1 H, m), 4.16 {1 H, (d, J 3.6 Hz) and 4.32 (d, J 7.8 Hz)}, 4.35-4.52 (7 H, m), 4.58-4.64 (1 H, m), 4.71 {1 H, (d, J 10.3 Hz) and 4.91 (d, J 10.9 Hz)}, 6.80-6.92 (8 H, m), 7.11 (2 H, d, J 8.8 Hz), 7.2-7.32 (6 H, m); LCMS [M+H]$^+$=830.35.

12-c. Urea Formation (69)

Compound 69 was prepared according to the procedure described in General Method 1, yield [30%, used directly in next step], LCMS [M+H]$^+$=1204.53.

12-d. Azide Reduction (70)

Compound 70 was prepared according to the procedure described in General Method 3 [99%, used directly in next step], LCMS [M+H]$^+$=1178.65.

12-e. Lipid HBTU Coupling (71)

Compound 71 was prepared according to the procedure described in General Method 4, LCMS [M+H]$^+$=1374.83.

12-f Global Deprotection (72)

Compound 72 was prepared according to the procedure described in General Method 5, [30%, yield over two steps from compound 70] as a white solid; LCMS [M+H]$^+$=894.22.

EXAMPLE 13
Synthesis of an Aminoacid Linked Lipidic Side Arm
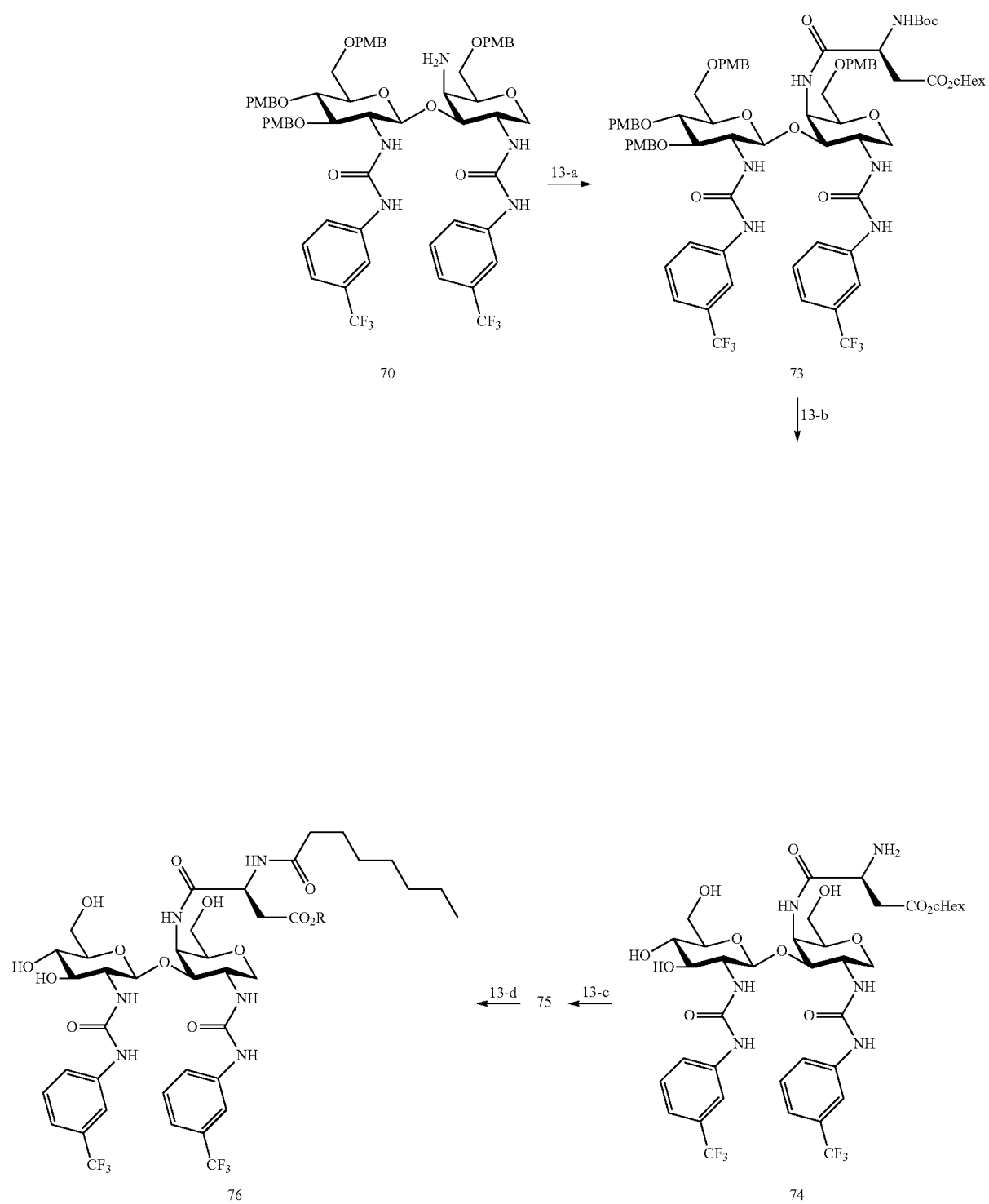

13-a. DIC Coupling of a Aminoacid Side Arm (73)

Compound 73 (using 0.034 mmol of 70) was prepared according to the procedure described in General Method 7; HPLC Method A, Rt=7.5 min, [M+H]$^+$=1475.

13-b. Deprotection of the Boc Protected Amine and 4Methoxybenzyl Groups (74)

Compound 74 was prepared according to the procedure described in General Method 5; HPLC Method A, Rt=4.82 min, [M+H]$^+$=895.

13-c. DIC Coupling of a Lipidic Side Arm (75)

Compound 75 was prepared according to the procedure described in General Method 7; HPLC-Method A, Rt=6.18 mins, [M+H]$^+$=1117; RT=7.16 min, [M+H]$^+$=1147.

13-d. Ester Hydrolysis to Provide the Free Acid (76)

Compound 75 was prepared according to the procedure described in General Method 8, yield 25.7% from 70; HPLC Method A, Rt=4.75 min, [M+H]$^+$=939.

EXAMPLE 14

Synthesis of an Aminoacid Linked Lipidic Side Arm-2

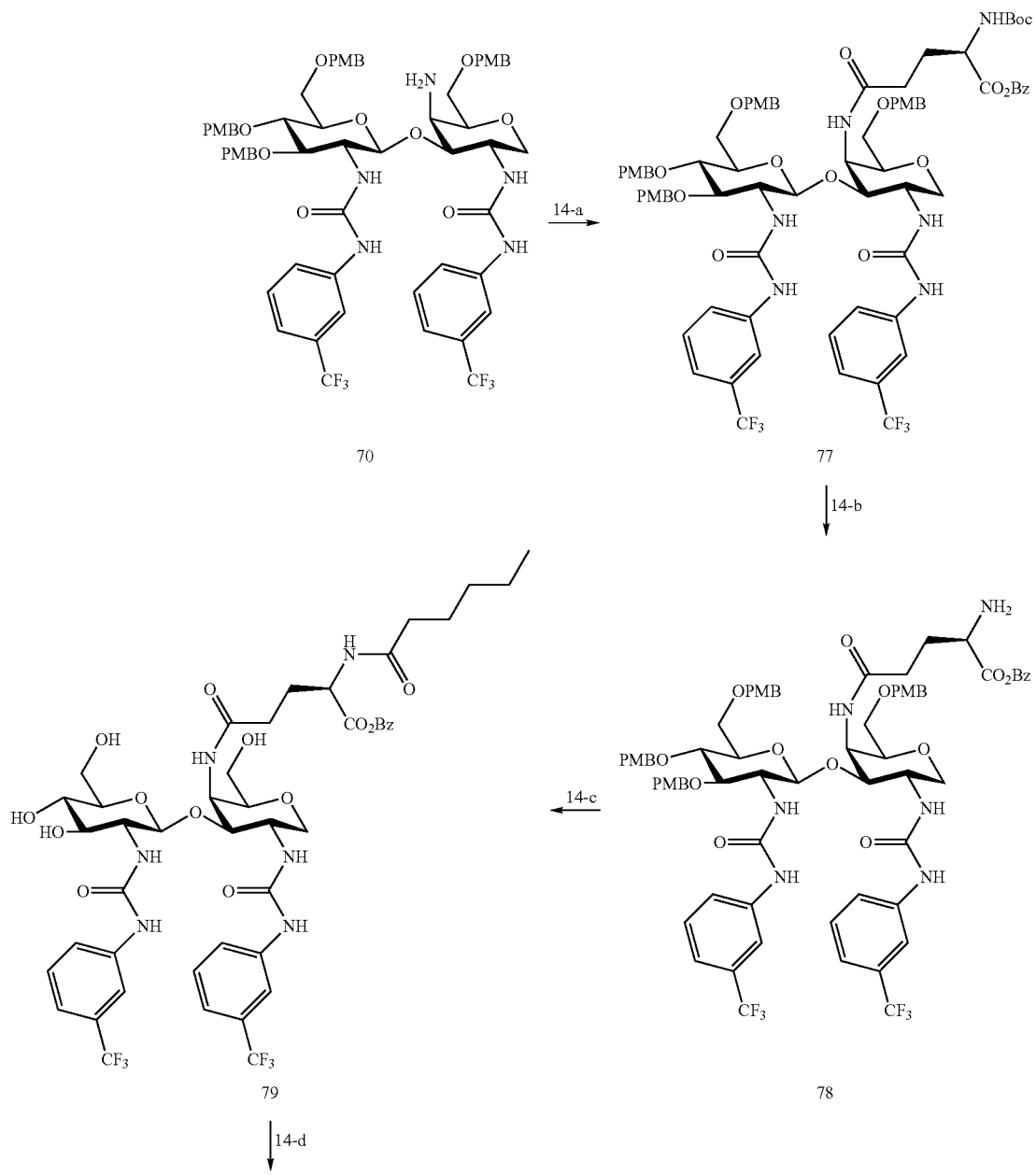

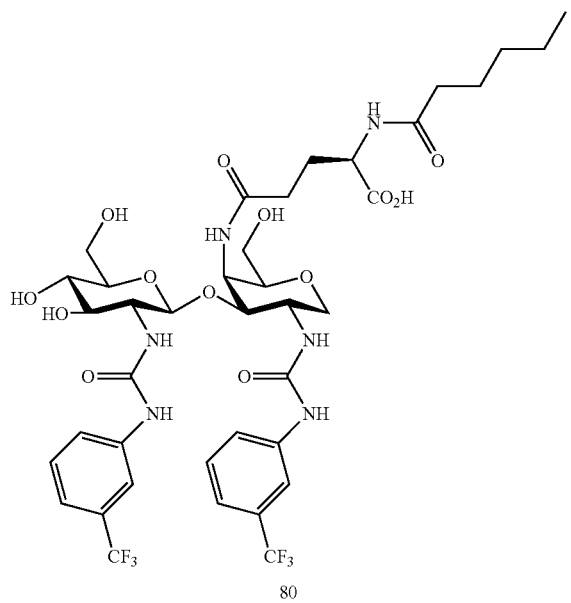

80

14-a. DIC Coupling of a Aminoacid Side Arm (77)

Compound 77 was prepared (using 0.034 mmol of 70) according to the procedure described in General Method 7, HPLC Method A, Rt=7.3 mins, [M+H]$^+$=1497.

14-b. Deprotection of the Boc Protected Amine and 4-Methoxybenzyl Groups (78)

Crude 77 was stirred at room temperature in DCM (2 mL), TFA (40 μL) and TES (100 μL) for 2 hrs. The reaction mixture was concentrated in vacuo, HPLC Method A, Rt=4.5 mins, [M+H]$^+$=917.

14-c. DIC Coupling of a Lipidic Side Arm (79)

Compound 79 was prepared according to the procedure described in General Method 7; HPLC Method A, Rt=5.15 mins, [M+H]$^+$=1014.

14-d. Ester Hydrolysis to Provide the Free Acid (80)

Compound 79 was prepared according to the procedure described in General Method 8, yield (from 70) 24.5%; HPLC-Method A, Rt=4.50 mins, [M+H]$^+$=925.

EXAMPLE 15
Synthesis of 2-deoxy-2-(3-trifluoromethyl)-ureido-β-D-glucopyranosyl 1,5-anhydro-2,4-dideoxy-4-(1-decanesulphonamido)-2-(3-trifluoromethyl)-ureido-D-galactitol 4 with a Sulphonamide Lipidic Side Arm

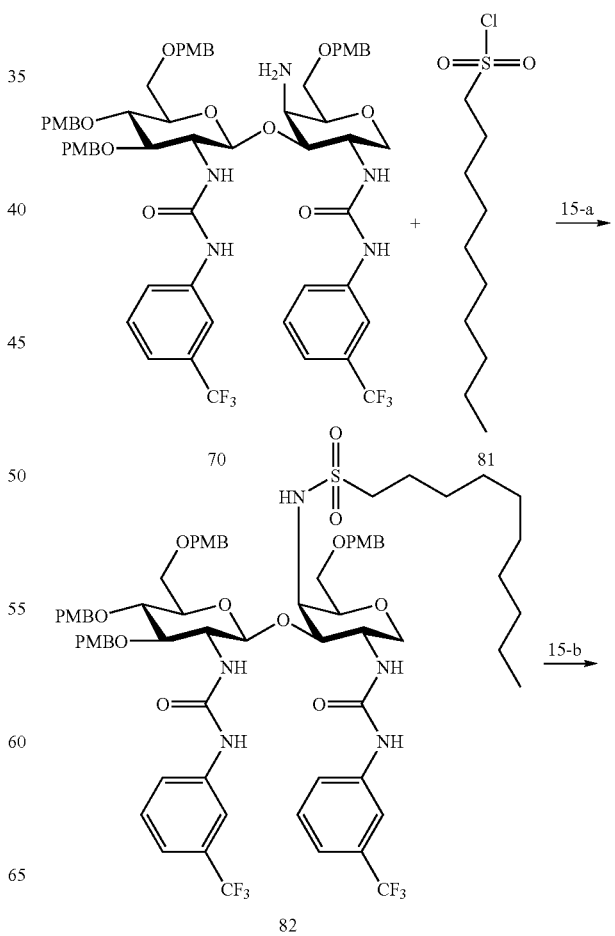

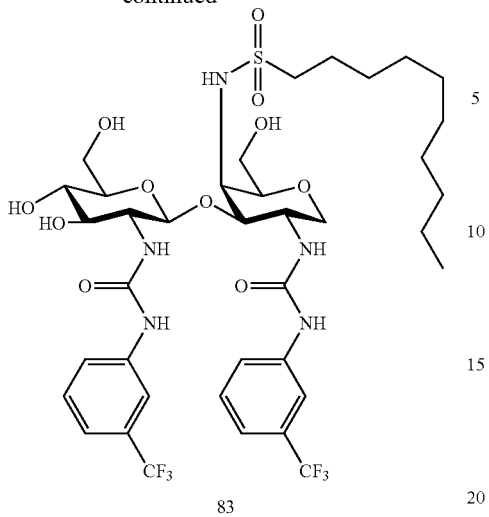

83

15-a. Formation of a Sulphonamide Linked Lipidic Side Arm (82)

To a solution of compound 70 (0.034 mmol) and pyridine (36.4 equiv) in dry dichloromethane (1 ml) was added 81 (20 equiv) in several portions. The resulting reaction mixture was stirred under nitrogen atmosphere for 2 hr and saturated sodium bicarbonate solution (20 ml) added. After 30 min stirring, the aqueous phase was extracted with dichloromethane; the combined organic solutions were dried over $MgSO_4$ and evaporated in vacuo to dryness. The residue was purified by preparative TLC (eluent: neat EtOAc) to furnish the crude 2-deoxy-3,4,6-tri-O-(4-methoxybenzyl)-2-(3-trifluoromethyl)-ureido-β-D-glucopyranosyl 1,5-anhydro-2,4-dideoxy-6-(4-methoxybenzyl)-4-(1-decanesulphonamido)-2-(3-trifluoromethyl)-ureido-D-galactitol 82 (HPLC Method A, Rt=7.71 mins, $[M+H]^+=1382.4$). The product was used for the next step without further purification.

15-b. Global Deprotection to provide the Final Product (83)

Compound 83 was prepared according to the procedure described in General Method 5, (10.8% from 70) HPLC Method A, Rt=11.85 mins, $[M+H]^+=902.53$)

EXAMPLE 16

Synthesis of 2-deoxy-2-(3-trifluoromethyl)-ureido-β-D-glucopyranosyl 1,5-anhydro-2,4-dideoxy-4-(1-decylphosphonamido)-2-(3-trifluoromethyl)-ureido-D-galactitol 7

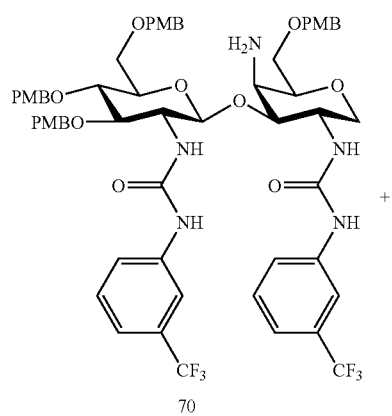

70

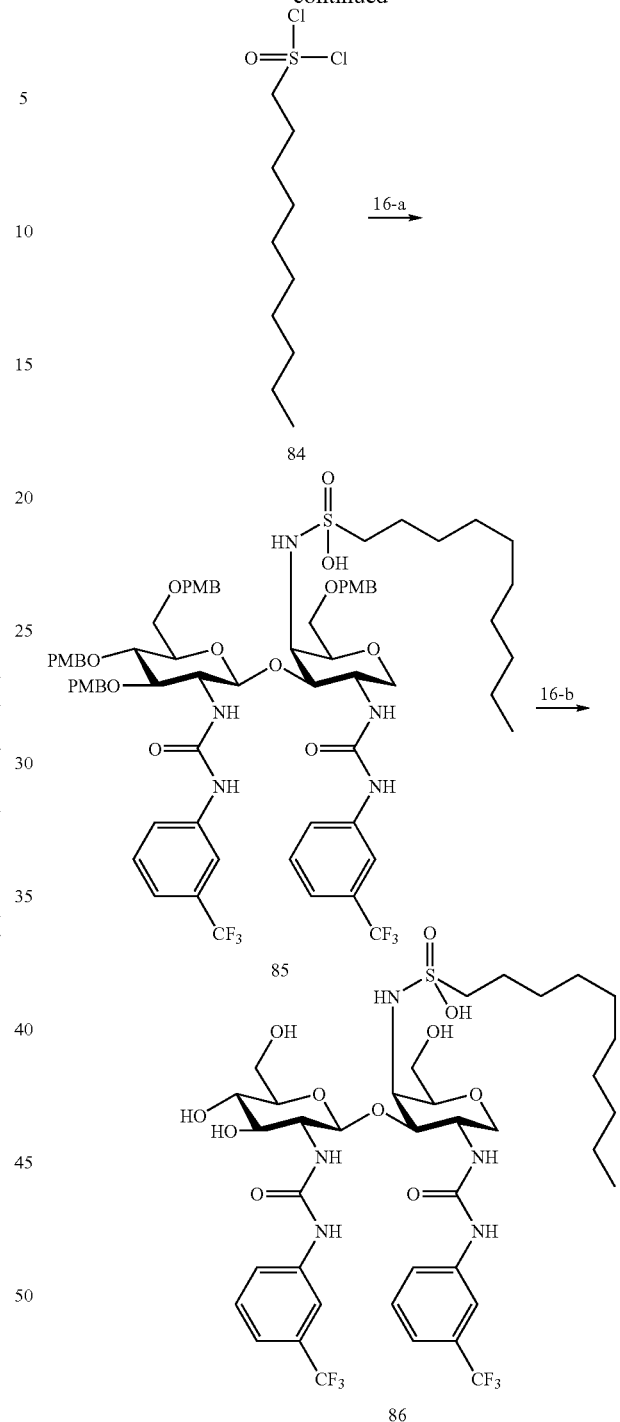

16-a. Formation of a Phosphonamide Linked Lipidic Side Arm (85)

To a solution of 1-decylphosphonic acid (1 mmol) and dimethylformamide (1.7 µl) in dry dichloromethane (4 ml) was added drop-wise oxalylchloride (261.2 µl, 3 mmol). The resultant solution was stirred at room temperature under nitrogen atmosphere for 1 hr and evaporated to dryness in vacuo. The residue was dried under high vacuum for 1 hr to afford compound 84 as brownish liquid. To a 84 (1 mmol) in DCM (4 ml) was added triethylamine (695 µl, 5 mmol) followed by compound 70 [0.034 mmol]. The resultant reaction mixture was stirred under nitrogen atmosphere for 1 hr and 1N hydrochloride solution (20 ml) added; the aqueous phase was extracted with dichloromethane (3×20 ml); the combined organic solutions were dried over MgSO4 and evaporated in vacuo to dryness. The product was used for the next step without further purification. (HPLC Method A, Rt=7.67 min, [M+H]$^+$=1382.82).

16-b. Global Deprotection to Provide the Final Product (86)

Compound 86 was prepared according to the procedure described in General Method 5, yield 8% (from 70); HPLC Method A, Rt=5.36 mins, [M+H]$^+$=902.5)

EXAMPLE 17

Synthesis of 2-deoxy-2-(3-trifluoromethyl)-ureido-(-β-D-glucopyranosyl 1,5-anhydro-2,4-dideoxy-4-(N-octanoylglycylamido)-2-(3-trifluoromethyl)-ureido-D-galactitol

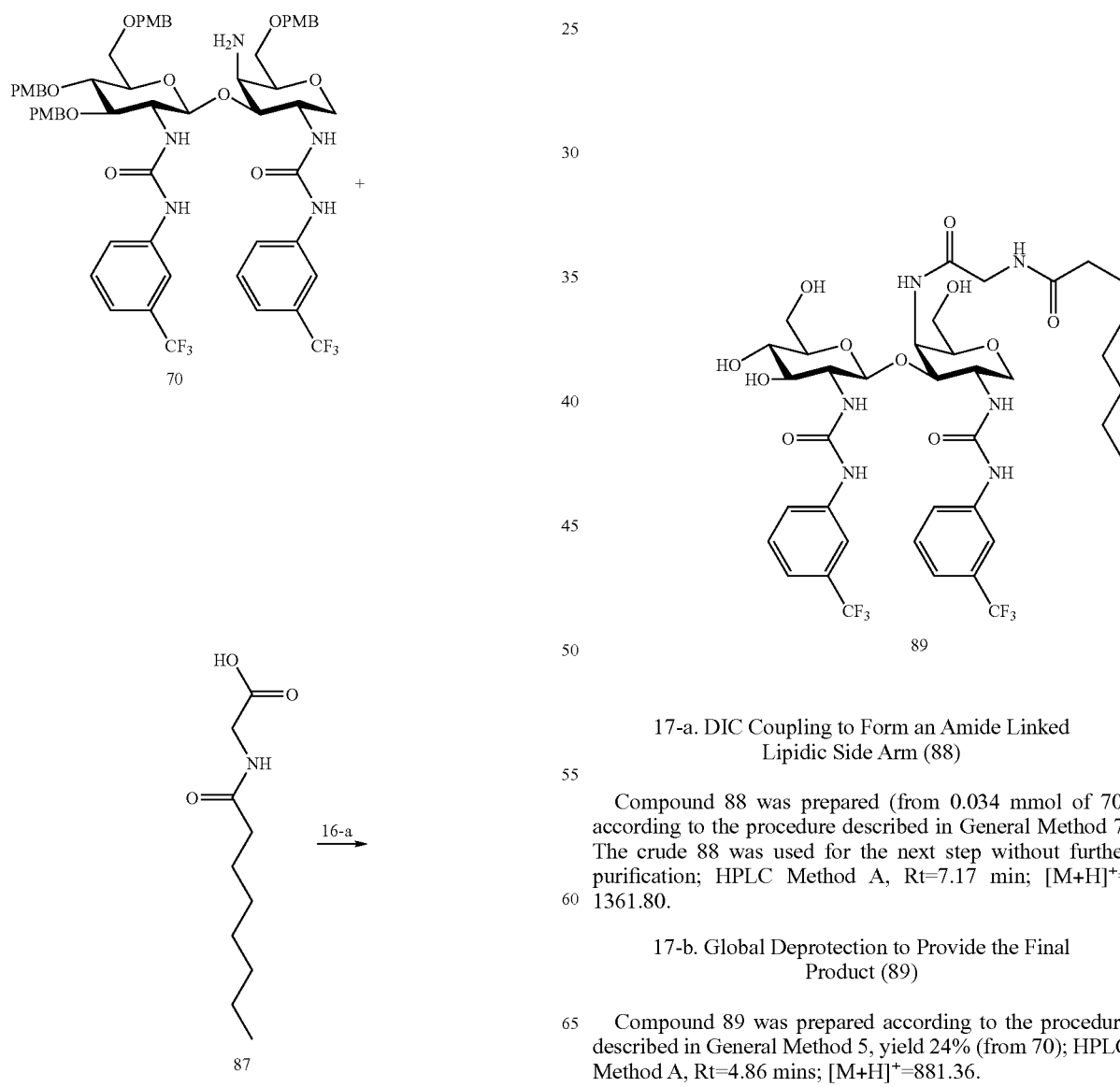

17-a. DIC Coupling to Form an Amide Linked Lipidic Side Arm (88)

Compound 88 was prepared (from 0.034 mmol of 70) according to the procedure described in General Method 7. The crude 88 was used for the next step without further purification; HPLC Method A, Rt=7.17 min; [M+H]$^+$=1361.80.

17-b. Global Deprotection to Provide the Final Product (89)

Compound 89 was prepared according to the procedure described in General Method 5, yield 24% (from 70); HPLC Method A, Rt=4.86 mins; [M+H]$^+$=881.36.

EXAMPLE 18

Synthesis of 2-deoxy-2-(3-trifluoromethyl)-ureido-β-D-glucopyranosyl 1,5-anhydro-2,4-dideoxy-4-(N-octanoyl-N'-yl-3,4-dioxo-cyclobutene-1.2-diamine)-2-(3-trifluoromethyl)-ureido-D-galactitol 92.

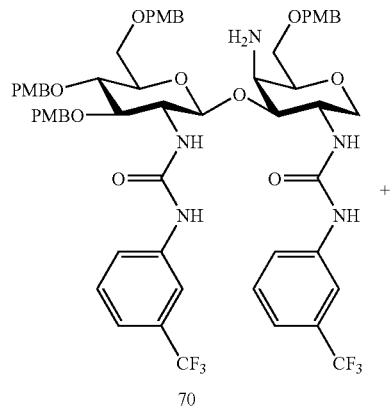

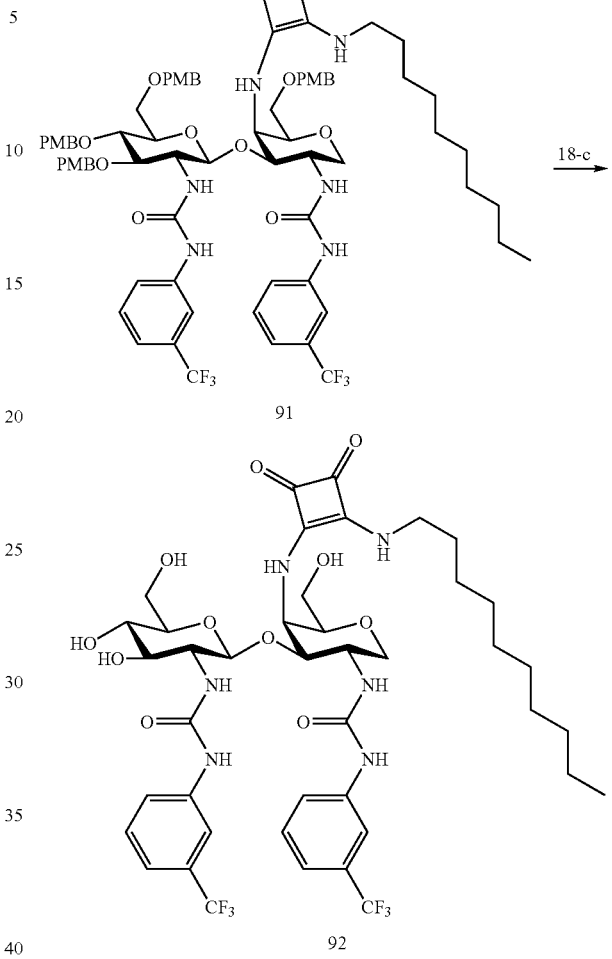

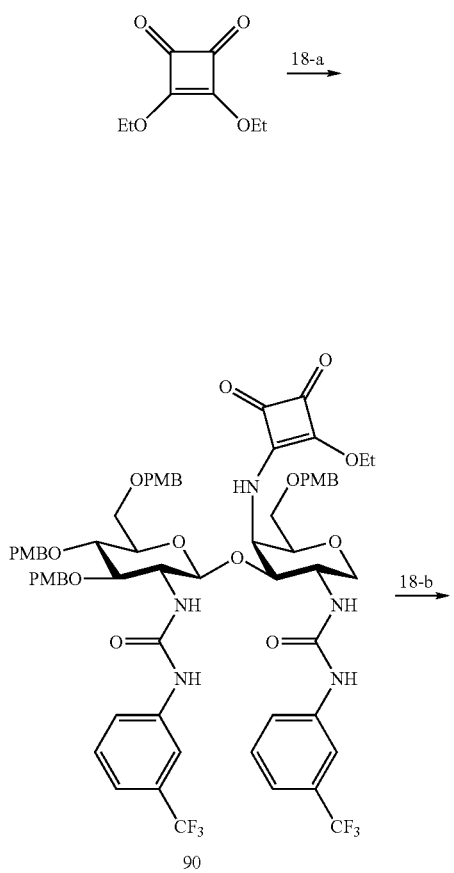

18-a. Coupling of Diethyl Squarate to Form a Vinylogous Amide (90)

Amine 70 (0.034 mmol) was dissolved in Ethanol and DIPEA (35 mmol) and diethylsquarate (70 μmol) was added. After stirring at room temperature a complete conversion of the starting material to 5 was observed; HPLC Method A, Rt=6.70 mins; [M+H]$^+$=1302.47.

18-b. Coupling of an Alkylamine Side Chain to the Squarate (91)

Decylamine (100 μmol) was added in the mixture (from 18-a) and heated to 50° C. over night. The mixture was diluted with ethyl acetate, washed twice with 10% citric acid, satd. sodium bicarbonate solution, and the solvents removed in vacuo. The crude 91 was used without further purification in the next step; HPLC Method A, Rt=7.66 mins, [M+H]$^+$=1413.15.

18-c. Global Deprotection to Provide the Final Product (92)

Compound 86 was prepared according to the procedure described in General Method 5 to give pure 92, yield 26.2% (from 70); HPLC Method A, Rt=5.61 mi; [M+H]$^+$=933.32.

EXAMPLE 19

Synthesis of 2-deoxy-2-(3-trifluoromethyl)-ureido-β-D-glucopyranosyl 1,5-anhydro-2,4-dideoxy-4-((N-hexanoyl)-4-amino-butyroyl)-2-(3-trifluoromethyl)-ureido-D-galactitol 10

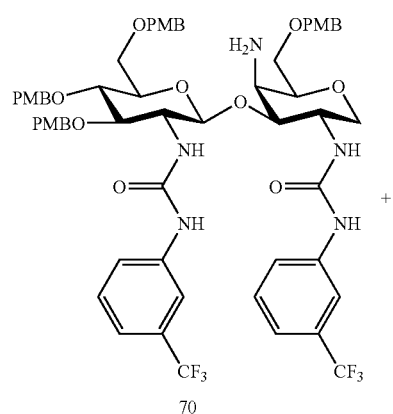

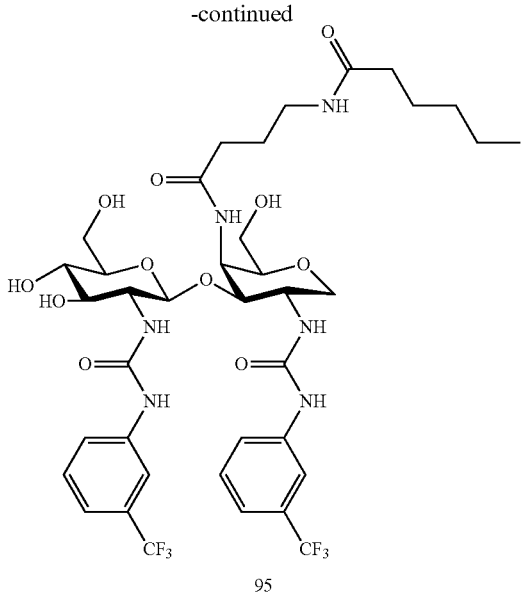

19-a. DIC Coupling to Form an Amide Linked Lipidic Side Arm (94)

Compound 94 was prepared (from 0.034 mmol of 70) according to the procedure described in General Method 7; HPLC Method A, Rt=6.85 min; $[M+H]^+=1361.47$. The crude product was directly used for the next step.

19-b. Global Deprotection to Provide the Final Product (95)

Compound 95 was prepared according to the procedure described in General Method 5, to give pure 10, yield 42.1% (from 70); HPLC Method A, Rt=4.60 min; $[M+H]^+=881.39$.

EXAMPLE 20

Synthesis of a Disaccharide with a Lipidic Side Chain and Acid Function

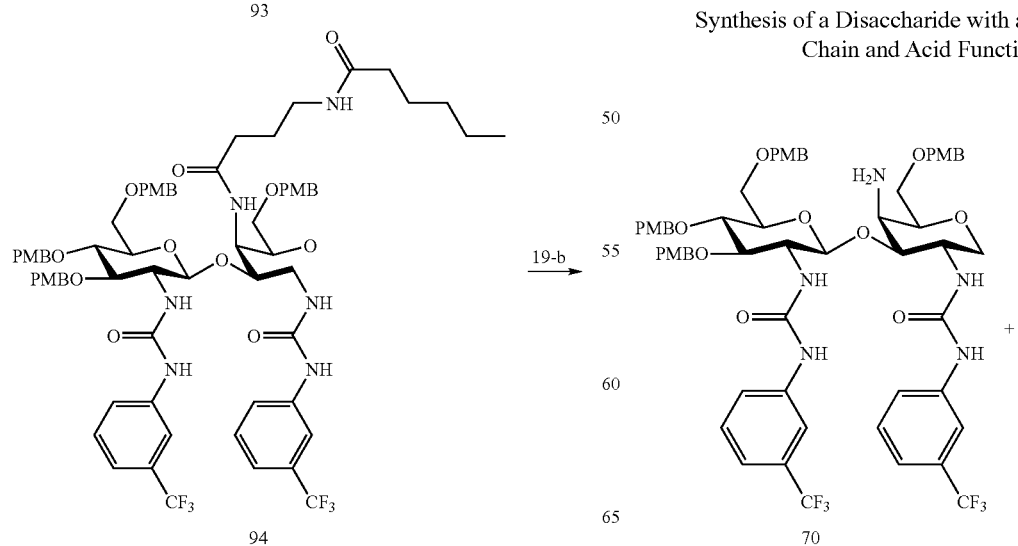

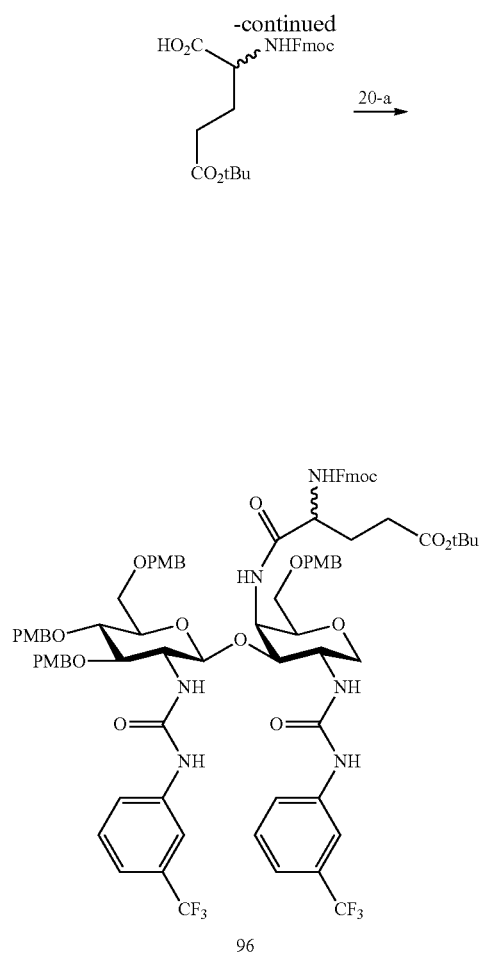

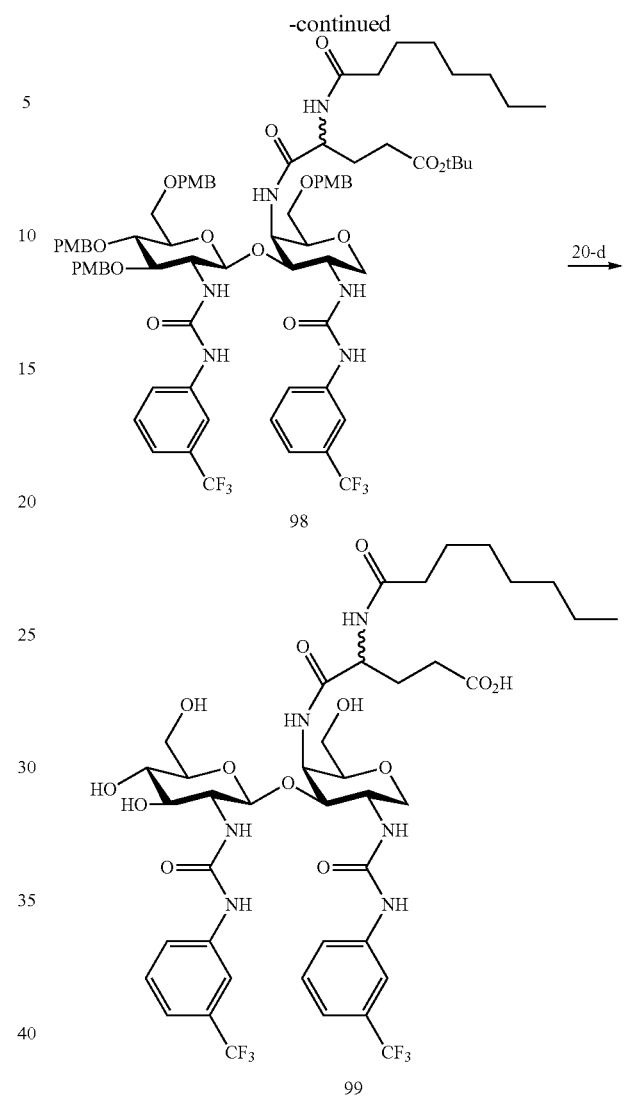

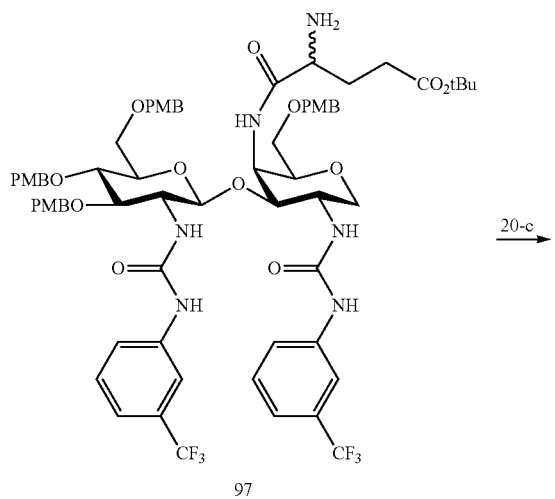

NB. Reaction series was completed separately for both the R and the S isomers.

20-a. DIC Coupling to Form an Amide Linked Lipidic Side Arm (96)

Compound 96 was prepared according to the procedure described in General Method 7, the crude product was directly used for the next step; HPLC Method A, Rt=7.70 mins; [M+H]$^+$=1585.45.

20-b and 20-c. Fmoc Deprotection Followed by Amide Formation (98)

Compound 98 was prepared according to the procedure described in General Method 9, the crude product was directly used for the general deprotection, (HPLC Method B, Rt=18.51 mins, [M+H]$^+$=1489.77).

20-d. Global Cleavage to Afford the Final Product

Compound 99 was prepared according to the procedure described in General Method 5, yield (R isomer) 27.5% from 70. yield (S isomer) 10.5% from 70; HPLC Method A, Rt=4.88 mins; [M+H]$^+$=953.46

EXAMPLE 21

Synthesis of a Disaccharide with a PEG Side Chain

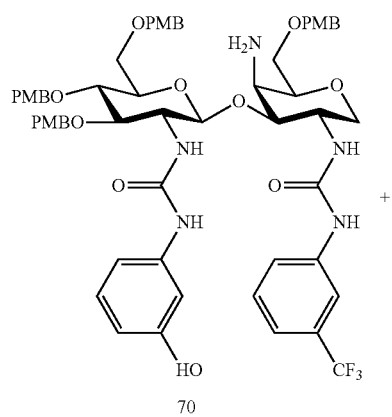

70

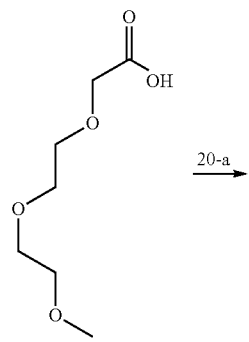

20-a →

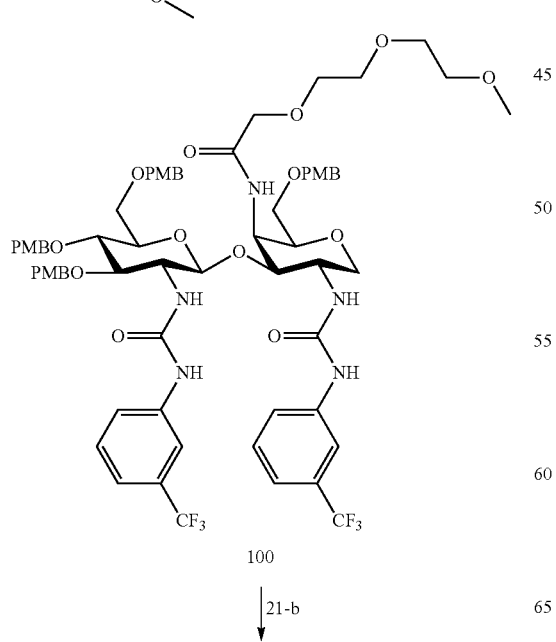

100

↓ 21-b

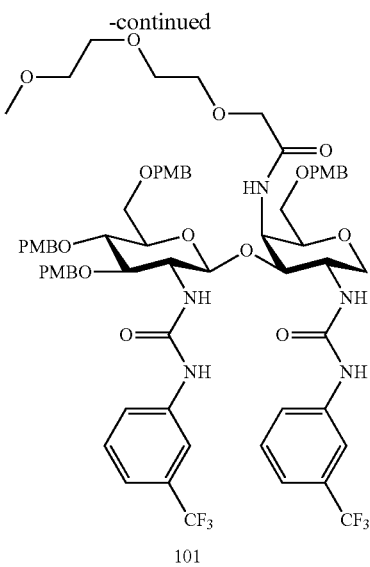

101

21-a. DIC Coupling to Form an Amide Linked PEG Side Arm (100)

Compound 100 was prepared according to the procedure described in General Method 7; HPLC Method A, Rt=6.81 mins; [M+H]$^+$=1338.49. The crude product was directly used for the next step.

21-b. Global Cleavage to Afford the Final Product (101).

Compound 101 was prepared according to the procedure described in General Method 5 (101 purified by preparative chromatography on a C18 column), yield 21.8% (from 70); HPLC Method A, Rt=4.27 min; [M+H]$^+$=958.52.

EXAMPLE 22

Synthesis of a Range of Lipid Conjugates

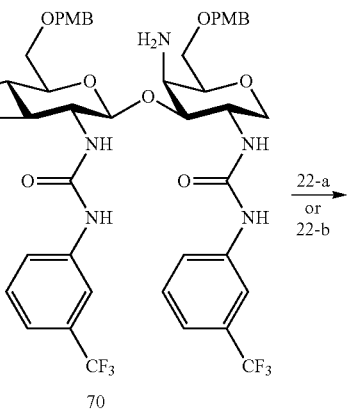

70

22-a or 22-b →

-continued

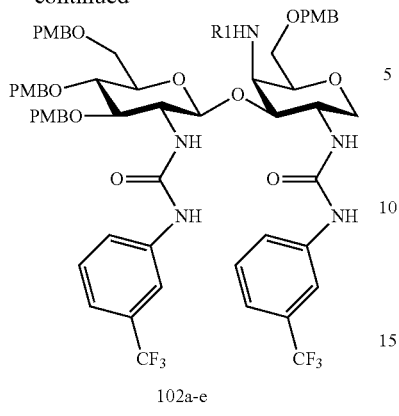

102a-e

|22-c
↓

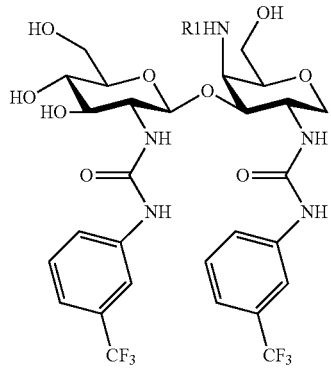

103a-e

22-a. Preparation of Amido Derivatives at C-4 (102a, 102b, 102c, 102e)

Compounds 102a, 102b, 102c, 102e were prepared according to the procedure provided in General Method 4.

22-b. Reaction with Acetic Anhydride (102d)

Added dropwise to a solution of the sugar amine (0.04 mmol) in dry dichloromethane (0.4 mL) was acetic anhydride (0.12 mmol) and the solution stirred for 16 h. Chloroform (15 mL) was then added and washed with water, 10% citric acid, saturated sodium hydrogen carbonate, brine, dried (MgSO$_4$) and the solvent removed under reduced pressure to give the title compound 5 quantitatively as an oil, LCMS [M+H]$^+$= 1220.5.

22-c. Global Cleavage to Afford the Final Product (103a-103e)

Compound 103a-e were prepared according to the procedure described in General Method 5.

TABLE 1

Derivatives prepared in Example 22.

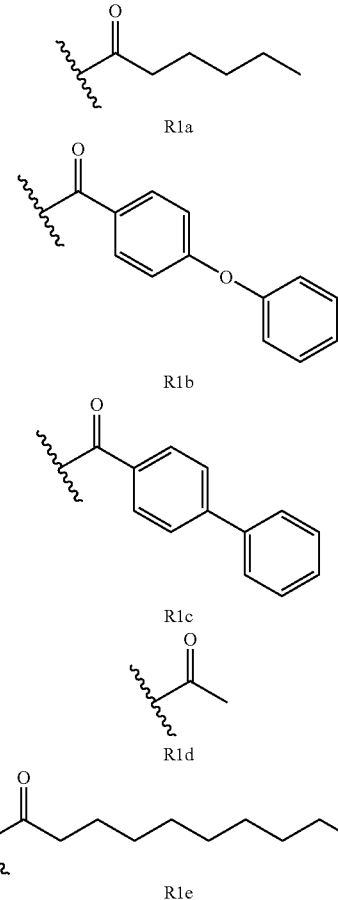

| Comp. No. | R1  | R2  | Molecular Ion       | Yield  |
|-----------|-----|-----|---------------------|--------|
| 102a      | R1a | R2a | [M+H]$^+$ = 1276.2  | 87%    |
| 102b      | R1b | R2a | [M+H]$^+$ = 1374.2  | Quant. |
| 102c      | R1c | R2a | [M+H]$^+$ = 1358.3  | Quant. |
| 102d      | R1d | R2a | [M+H]$^+$ = 1220.5  | Quant. |
| 102e      | R1e | R2a | [M+H]$^+$ = 1346.5  | Quant. |
| 103a      | R1a | R2b | [M+H]$^+$ = 796.3   | 50%    |
| 103b      | R1b | R2b | [M+H]$^+$ = 894.3   | 49%    |
| 103c      | R1c | R2b | [M+H]$^+$ = 878.3   | 30%    |
| 103d      | R1d | R2b | [M+H]$^+$ = 740.1   | 30%    |
| 103e      | R1e | R2b | [M+H]$^+$ = 866.2   | 41%    |

Side Arms for Table 1.

TABLE 1-continued

Derivatives prepared in Example 22.

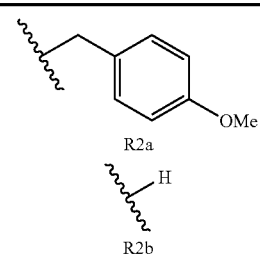

| Comp. No. | R1 | R2 | Molecular Ion | Yield |
|---|---|---|---|---|

R2a

R2b

EXAMPLE 23

Synthesis of a Further Disaccharidic Library

Part 1: Preparation of Compounds 111-01 to 111-30

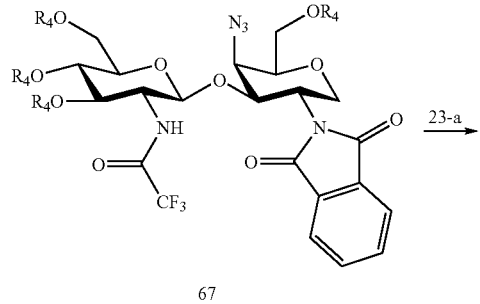

67

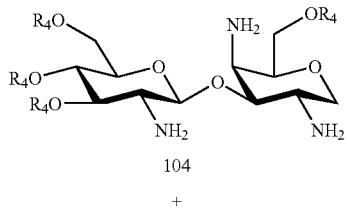

104
+

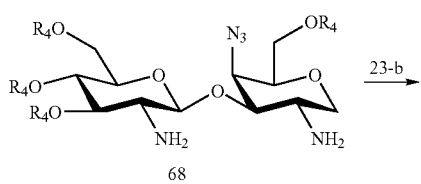

68

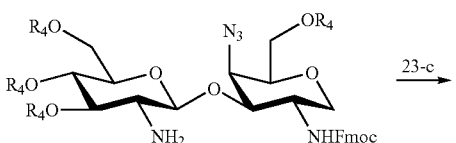

105

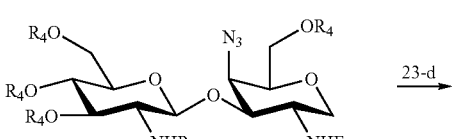

106-01 to 106-07

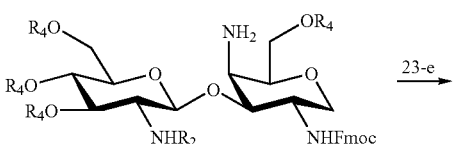

107-01 to 107-05

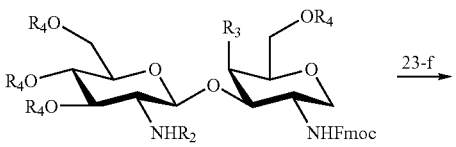

108-01 to 108-10

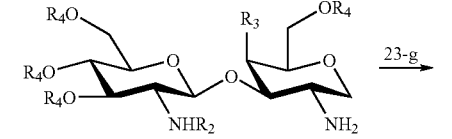

109-01 to 109-05

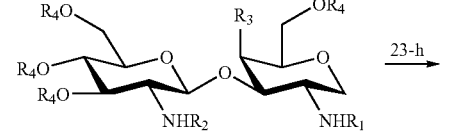

110-01 to 110-31

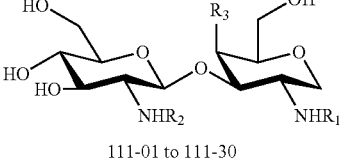

111-01 to 111-30

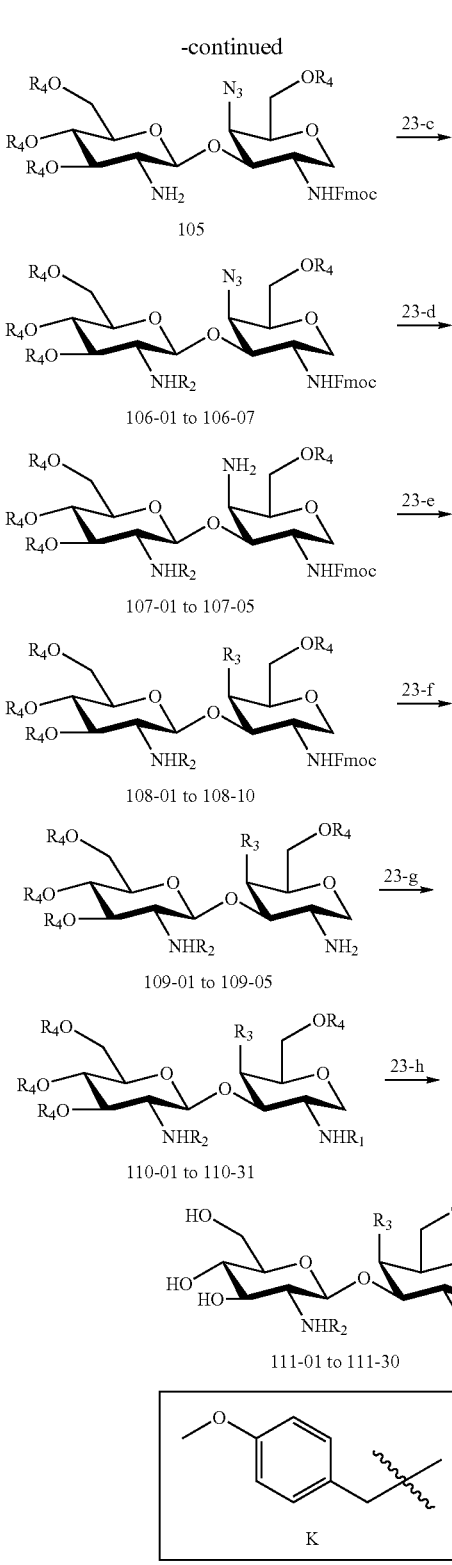

K

Conditions: (23-a) General Method 10; (23-b) General Method 11; (23-c) For General Methods used for specific compounds see Table 2; (23-d) General Method 3; (23-e) For General Methods used for specific compounds see Table 2; (23-f) and (x-g) General Method 9; (23-h) For General Methods used for specific compounds see Table 2.

Part 2: Preparation of Compound 113-01 to 113-03

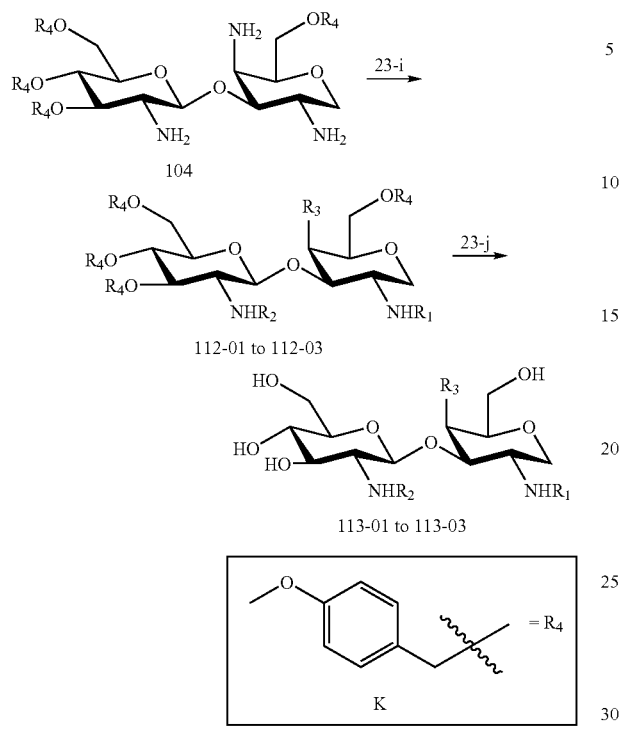

Conditions: (a) For General Methods for specific compounds see Table 2; (b) General Method 5

Part 3: Preparation of Compounds 114-01-114-03 for the Synthesis of Alternate Urea Building Blocks For the Preparation of Further Derivatives at $R_3$ as Exemplified by Structures 117-01-117-15 (by employing 5 different lipidic side chains).

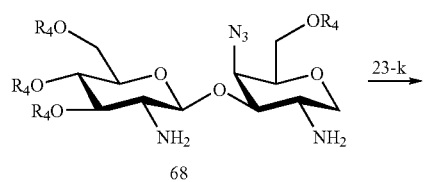

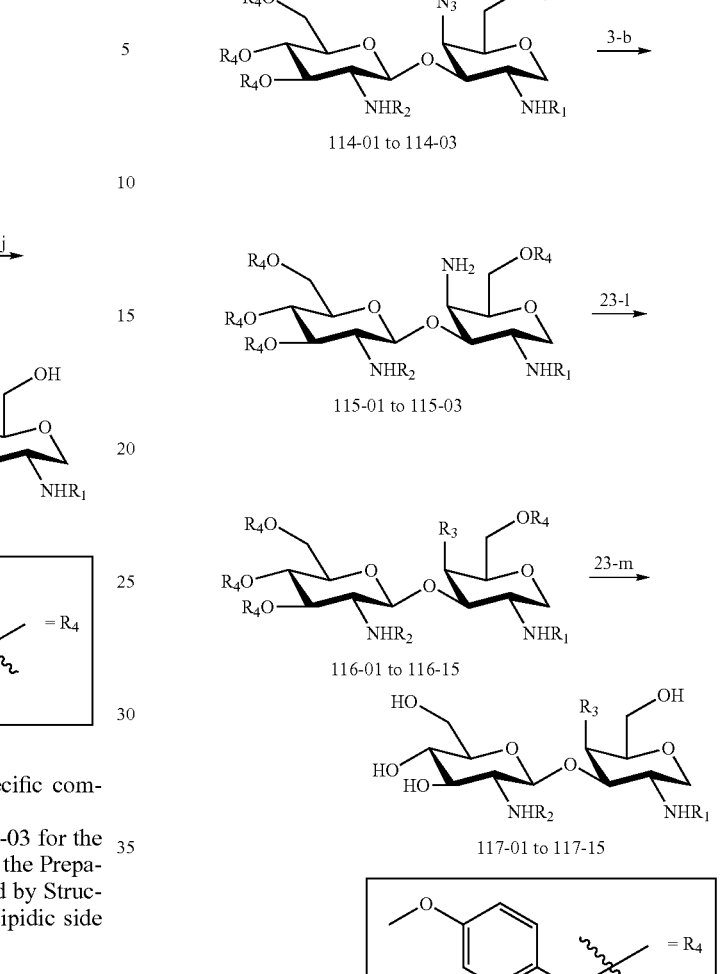

Conditions: (a) General Method 1; (b) General Method 3; (c) General Methods 1,4,7,14 and 15 as appropriate depending upon lipidic side chain to be coupled (d) General Method 5 6 and 17.

TABLE 2

Experimental Results, Intermediates and Products for Example 23

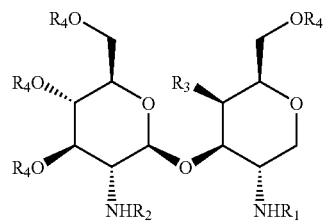

| Product | SM* | M§ | R1 | R2 | R3 | R4 | [M+X]+ | Rt (min)‡ | Yield (%) |
|---|---|---|---|---|---|---|---|---|---|
| 68 | 67 | 10 | I | I | L | K | [M+H]+ = 830.5 | 6.07 | 74.8 |
| 104 | 67 | 10 | I | I | M | K | [M+H]+ = 804.5 | 5.36 | 18 |

TABLE 2-continued

| | | | | | | | | | |
|---|---|---|---|---|---|---|---|---|---|
| 105 | 68 | 11 | H | I | L | K | [M+H]⁺ = 1052.52 | 8.0–12.0 | 32 |
| 106-01 | 105 | 15 | H | N | L | K | [M+H]⁺ = 1094.6 | 6.90 | 100 |
| 106-02 | 68 | 11 | H | H | L | K | [M+H]⁺ = 1274.7 | 7.66 | 19.5 |
| 106-03 | 105 | 4 | H | C | L | K | [M+H]⁺ = 1224.7 | 7.32 | 84 |
| 106-04 | 105 | 14 | H | D | L | K | [M+Na]⁺ = 1228.6 | 7.45 | 100 |
| 106-05 | 105 | 1 | H | E | L | K | [M+Na]⁺ = 1261.7 | 7.38 | 78 |
| 106-06 | 105 | 14 | H | F | L | K | [M+H]⁺ = 1205.7 | 7.35 | 98 |
| 106-07 | 105 | 13 | H | G | L | K | [M+Na]⁺ = 1208.8 | 7.43 | 82 |
| 107-01 | 106-03 | 3 | H | C | M | K | Detected in 108-01 form | | 100 |
| 107-02 | 106-04 | 3 | H | D | M | K | Detected in 108-02 form | | 96 |
| 107-03 | 106-05 | 3 | H | E | M | K | Detected in 108-03 form | | 100 |
| 107-04 | 106-06 | 3 | H | F | M | K | Detected in 108-04 form | | 100 |
| 107-05 | 106-07 | 3 | H | G | M | K | Detected in 108-05 form | | 100 |
| 108-01 | 107-01 | 15 | H | C | B | K | [M+H]⁺ = 1240.7 | 6.99 | 100 |
| 108-02 | 107-02 | 15 | H | D | B | K | [M+H]⁺ = 1222.7 | 7.07 | 90 |
| 108-03 | 107-03 | 15 | H | E | B | K | [M+H]⁺ = 1255.5 | 6.99 | 100 |
| 108-04 | 107-04 | 15 | H | F | B | K | [M+H]⁺ = 1221.3 | 7.42 | 86 |
| 108-05 | 107-05 | 15 | H | G | B | K | [M+Na]⁺ = 1224.8 | 7.05 | 95 |
| 108-06 | 107-01 | 4 | H | C | A | K | [M+Na]⁺ = 1366.9 | 8.09 | 85 |
| 108-07 | 107-02 | 4 | H | D | A | K | [M+H]⁺ = 1348.9 | 8.01 | 67.7 |
| 108-08 | 107-03 | 4 | H | E | A | K | [M+H]⁺ = 1381.9 | 8.33 | 88 |
| 108-09 | 107-04 | 4 | H | F | A | K | [M+H]⁺ = 1347.4 | 7.86 | 100 |
| 108-10 | 107-05 | 4 | H | G | A | K | [M+H]⁺ = 1328.6 | 8.18 | 100 |
| 109-01 | 108-06 | 16 | I | C | A | K | Detected in 110-02 form | | 67 |
| 109-02 | 108-07 | 16 | I | D | A | K | Detected in 110-03 form | | 61 |
| 109-03 | 108-08 | 16 | I | E | A | K | Detected in 110-04 form | | 90 |
| 109-04 | 108-09 | 16 | I | F | A | K | Detected in 110-05 form | | 58 |
| 109-05 | 108-10 | 16 | I | G | A | K | Detected in 110-06 form | | 51 |
| 110-01 | 68 | 15 | N | N | L | K | [M+H]⁺ = 914.5 | 5.71 | 100 |
| 110-02 | 109-01 | 15 | N | C | A | K | [M+H]⁺ = 1186.76 | 7.50 | 100 |
| 110-03 | 109-02 | 15 | N | D | A | K | [M+H]⁺ = 1168.77 | 7.54 | 100 |
| 110-04 | 109-03 | 15 | N | E | A | K | [M+H]⁺ = 1201.8 | 7.33 | 100 |
| 110-05 | 109-04 | 15 | N | F | A | K | [M+H]⁺ = 1167.5 | 7.30 | 100 |
| 110-06 | 109-05 | 15 | N | G | A | K | [M+H]⁺ = 1148.5 | 7.51 | 100 |
| 110-07 | 109-01 | 4 | C | C | A | K | [M+H]⁺ = 1316.7 | 7.59 | 86.8 |
| 110-08 | 109-02 | 4 | C | D | A | K | [M+H]⁺ = 1298.6 | 7.94 | 100 |
| 110-09 | 109-03 | 4 | C | E | A | K | [M+H]⁺ = 1331.71 | 7.90 | 100 |
| 110-10 | 109-04 | 4 | C | F | A | K | [M+H]⁺ = 1297.5 | 7.58 | 100 |
| 110-11 | 109-05 | 4 | C | G | A | K | [M+H]⁺ = 1278.7 | 7.82 | 100 |
| 110-12 | 109-01 | 14 | D | C | A | K | [M+H]⁺ = 1298.5 | 7.68 | 84.7 |
| 110-13 | 109-02 | 14 | D | D | A | K | [M+H]⁺ = 1280.4 | 7.92 | 100 |
| 110-14 | 109-03 | 14 | D | E | A | K | [M+H]⁺ = 1313.83 | 8.03 | 100 |
| 110-15 | 109-05 | 14 | D | G | A | K | [M+H]⁺ = 1260.5 | 7.89 | 28.2 |
| 110-16 | 109-01 | 1 | E | C | A | K | [M+Na]⁺ = 1353.8 | 7.86 | 100 |
| 110-17 | 109-02 | 1 | E | D | A | K | [M+H]⁺ = 1313.81 | 7.81 | 100 |
| 110-18 | 109-04 | 1 | E | F | A | K | [M+H]⁺ = 1312.8 | 7.64 | 100 |
| 110-19 | 109-05 | 1 | E | G | A | K | [M+H]⁺ = 1293.8 | 7.88 | 100 |
| 110-20 | 109-01 | 12 | F | C | A | K | [M+H]⁺ = 1297.9 | 7.60 | 80 |
| 110-21 | 109-02 | 12 | F | D | A | K | [M+H]⁺ = 1279.8 | 7.92 | 77 |
| 110-22 | 109-03 | 12 | F | E | A | K | [M+H]⁺ = 1312.84 | 7.65 | 100 |
| 110-23 | 109-04 | 12 | F | F | A | K | [M+H]⁺ = 1278.8 | 7.73 | 73 |
| 110-24 | 109-05 | 12 | F | G | A | K | [M+H]⁺ = 1259.9 | 7.64 | 70 |
| 110-25 | 109-01 | 13 | G | C | A | K | [M+H]⁺ = 1278.8 | 7.64 | 66 |
| 110-26 | 109-02 | 13 | G | D | A | K | [M+H]⁺ = 1260.8 | 7.91 | 75 |
| 110-27 | 109-03 | 13 | G | E | A | K | [M+H]⁺ = 1293.87 | 7.96 | 100 |
| 110-28 | 109-04 | 13 | G | F | A | K | [M+H]⁺ = 1259.8 | 7.75 | 72 |
| 110-29 | 109-05 | 13 | G | G | A | K | [M+H]⁺ = 1240.8 | 7.67 | 80 |
| 110-30 | 109-03 | 1 | O | E | A | K | Compound fragments to 110-31 under LCMS conditions | | 100 |
| 110-31 | | | P | E | A | K | [M+H]⁺ = 1202.81 | 7.26 | |
| 111-01 | 110-07 | 5 | C | C | A | I | [M+H]⁺ = 836.4 | 5.33 | 100 |
| 111-02 | 110-08 | 5 | C | D | A | I | [M+H]⁺ = 818.4 | 5.57 | 100 |
| 111-03 | 110-09 | 5 | C | E | A | I | [M+H]⁺ = 851.5 | 5.43 | 100 |
| 111-04 | 110-10 | 6 | C | F | A | I | [M+H]⁺ = 817.4 | 5.44 | 18 |
| 111-05 | 110-11 | 5 | C | G | A | I | [M+H]⁺ = 798.4 | 5.54 | 100 |
| 111-06 | 110-12 | 5 | D | C | A | I | [M+H]⁺ = 818.4 | 5.56 | 100 |
| 111-07 | 110-13 | 4 | D | D | A | I | [M+H]⁺ = 800.4 | 5.47 | 100 |
| 111-08 | 110-14 | 5 | D | E | A | I | [M+H]⁺ = 833.4 | 5.83 | 100 |
| 111-09 | 110-15 | 5 | D | G | A | I | [M+H]⁺ = 780.4 | 5.41 | 100 |
| 111-10 | 110-16 | 5 | E | C | A | I | [M+H]⁺ = 851.3 | 5.64 | 100 |
| 111-11 | 110-17 | 5 | E | D | A | I | [M+H]⁺ = 833.3 | 5.75 | 100 |
| 111-12 | 110-18 | 5 | E | F | A | I | [M+H]⁺ = 832.5 | 5.53 | 16 |
| 111-13 | 110-19 | 5 | E | G | A | I | [M+H]⁺ = 813.3 | 5.69 | 100 |
| 111-14 | 110-20 | 6 | F | C | A | I | [M+H]⁺ = 817.4 | 5.49 | 51 |
| 111-15 | 110-21 | 6 | F | D | A | I | [M+H]⁺ = 799.4 | 5.46 | 48 |
| 111-16 | 110-22 | 5 | F | E | A | I | [M+H]⁺ = 832.5 | 5.65 | 2 |
| 111-17 | 110-23 | 6 | F | F | A | I | [M+H]⁺ = 798.4 | 5.36 | 20 |
| 111-18 | 110-24 | 6 | F | G | A | I | [M+H]⁺ = 779.5 | 5.58 | 53 |
| 111-19 | 110-25 | 5 | G | C | A | I | [M+H]⁺ = 798.5 | 5.30 | 100 |
| 111-20 | 110-26 | 5 | G | D | A | I | [M+H]⁺ = 780.5 | 5.57 | 100 |

TABLE 2-continued

| | | | | | | | | | |
|---|---|---|---|---|---|---|---|---|---|
| 111-21 | 110-27 | 5 | G | E | A | I | [M+H]⁺ = 813.4 | 5.69 | 100 |
| 111-22 | 110-28 | 6 | G | F | A | I | [M+H]⁺ = 779.5 | 5.08 | 10 |
| 111-23 | 110-29 | 5 | G | G | A | I | [M+H]⁺ = 760.5 | 5.28 | 100 |
| 111-24 | 108-06 | 5 | H | C | A | I | [M+H]⁺ = 886.55 | 6.07 | 100 |
| 111-25 | 108-07 | 5 | H | D | A | I | [M+H]⁺ = 868.58 | 5.99 | 100 |
| 111-26 | 108-08 | 5 | H | E | A | I | [M+H]⁺ = 901.4 | 6.00 | 100 |
| 111-27 | 108-09 | 6 | H | F | A | I | [M+H]⁺ = 867.6 | 6.03 | 20 |
| 111-28 | 108-10 | 5 | H | G | A | I | [M+H]⁺ = 848.6 | 5.91 | 100 |
| 111-29 | 110-30 | 5 | P | E | A | I | [M+H]⁺ = 722.4 | 4.63 | 100 |
| 111-30 | 109-03 | 5 | I | E | A | I | [M+H]⁺ = 679.5 | 4.62 | 100 |
| 112-01 | 104 | 15 | N | N | B | K | [M+Na]⁺ = 952.7 | 5.01 | 47 |
| 112-02 | 104 | 4 | C | C | Q | K | [M+H]⁺ = 1320.5 | 6.99 | 76 |
| 112-03 | 104 | 1 | E | E | R | K | [M+H]⁺ = 1365.4 | 7.21 | 92 |
| 113-01 | 112-01 | 5 | N | N | B | I | [M+H]⁺ = 450.26 | 0.69 | 100 |
| 113-02 | 112-02 | 5 | C | C | Q | I | [M+H]⁺ = 840.4 | 4.53 | 100 |
| 113-03 | 104 | 5 | I | I | M | I | [M+H]⁺ = 324.2 | 0.62 | 100 |
| 114-01 | 68 | 1 | S | S | L | K | [M+H]⁺ = 1204.9 | 7.02 | 100 |
| 114-02 | 68 | 1 | T | T | L | K | [M+H]⁺ = 1096.5 | 6.82 | 100 |
| 115-03 | 68 | 1 | U | U | L | K | [M+H]⁺ = 1204.3 | 7.25 | 100 |
| 111-01-1 | 111-01 | 17 | C | C | A | I | As Start Material | N/A | 43 |
| 111-02-1 | 111-02 | 17 | C | D | A | I | As Start Material | N/A | 19.2 |
| 111-06-1 | 111-06 | 17 | D | C | A | I | As Start Material | N/A | 34.5 |
| 111-07-1 | 111-07 | 17 | D | D | A | I | As Start Material | N/A | 51 |
| 111-08-1 | 111-08 | 17 | D | E | A | I | As Start Material | N/A | 27 |
| 111-10-1 | 111-10 | 17 | E | C | A | I | As Start Material | N/A | 16 |
| 111-11-1 | 111-11 | 17 | E | D | A | I | As Start Material | N/A | 75 |
| 111-29-1 | 111-29 | 17 | P | E | A | I | As Start Material | N/A | 45 |

SM* = Starting Material

M§ = Method of Synthesis (General Method)

Rt (min)‡: All compounds in Table 2 were analysed by HPLC Method A.

Note:

Under the employed analytical conditions, compounds containing amino group (compounds classed as 68, 104, 105, 107, 109) elute in unusual broad peaks, sometimes several minutes wide; therefore, most of the time they are detected as acetamide derivatives obtained via acylating with acetic anhydride.]

Substituents for Table 2

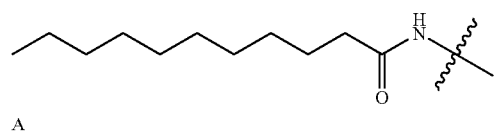

A

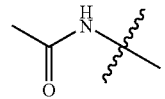

B

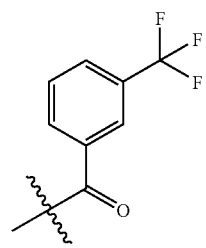

C

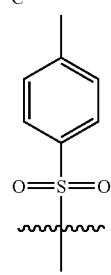

D

TABLE 2-continued
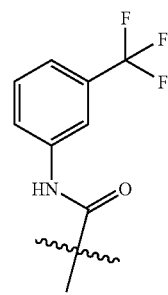
E
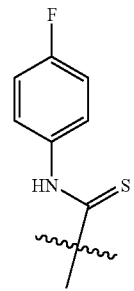
F
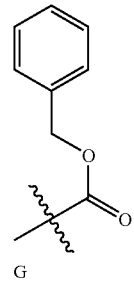
G
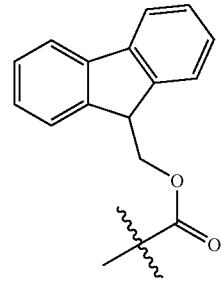
H
I
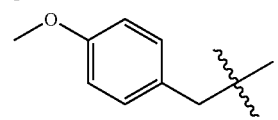
K
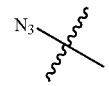
L
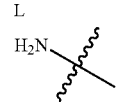
M TABLE 2-continued
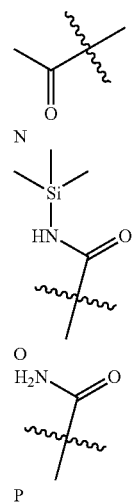
N
O
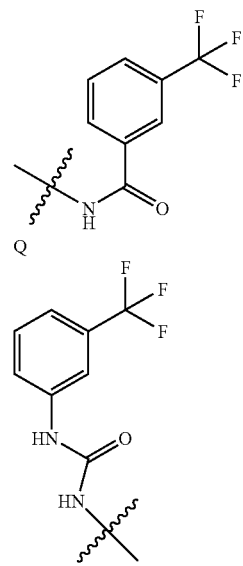
P
Q
R
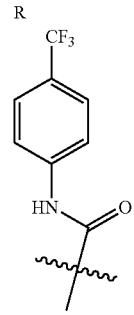
S
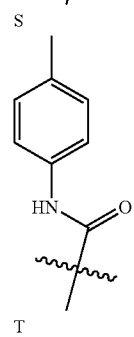
T

TABLE 2-continued

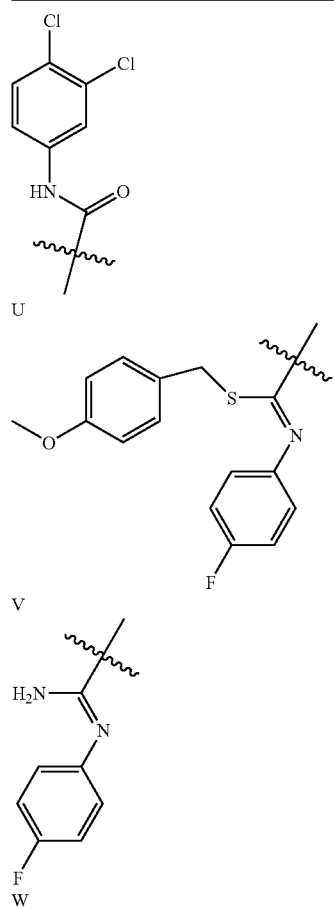

U

V

W

HPLC Methods.

| HPLC Method A | | | |
|---|---|---|---|
| Time | H₂O % | MeCN % | Flow Rate mL/min |
| 0 | 95 | 5 | 2 |
| 1 | 95 | 5 | 2 |
| 7 | 0 | 100 | 2 |
| 12 | 0 | 100 | 2 |

Agilent SB Zorbax C18 4.6×50 mm (5 μm, 80 Å)
LC Mobile Phase: Acetonitrile: Water 0.1% formic acid

| HPLC Method B | | | |
|---|---|---|---|
| Time | H₂O % | MeCN % | Flow Rate mL/min |
| 0.00 | 95 | 5 | |
| 1.00 | 95 | 5 | |
| 20.00 | 0 | 100 | |

Agilent SB Zorbax C18 4.6×50 mm (5 μm, 80 Å)
LC Mobile Phase: Acetonitrile: Water 0.1% formic acid

EXAMPLE 24

Synthesis of an Alpha 1→4 Linked Disaccharidic Compound

Selective Removal of Protecting Groups for Diversity-Part 1

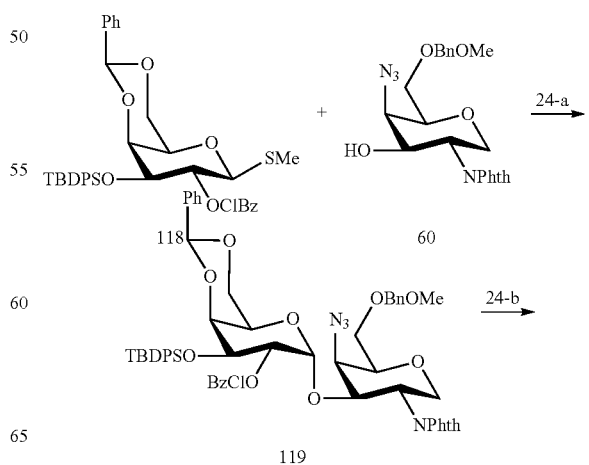

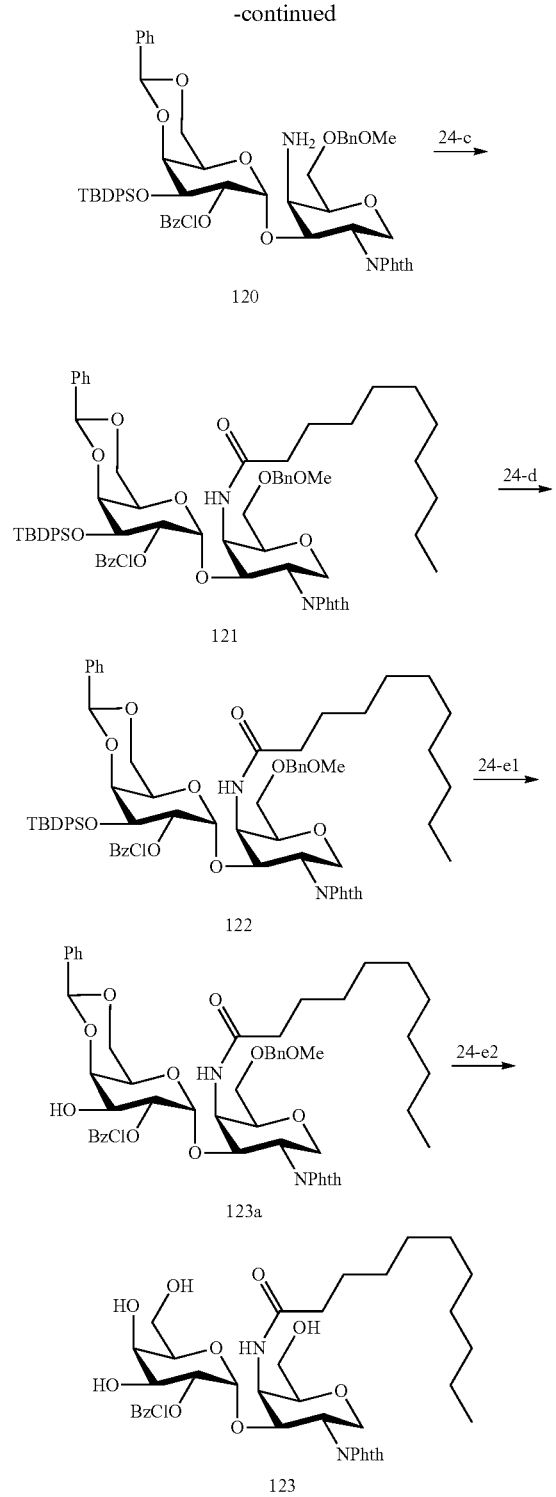

at room temperature. After 2.5 h further 60 [0.2 mmol], 2,6-di-tert.-butylpyridine [0.2 mmol] and DMTST [0.2 mmol] were added and the reaction stirred at room temperature for 1 h. The reaction was then quenched with triethylamine, the solvents were removed in vacuo and the product purified by column chromatography (silica, petrolether/ethyl acetate 2:1) to give 119 as a colourless foam [63%]; HPLC Method A, Rt=8.09 mins, [M+Na]$^+$=1087.56; 1H-NMR (CDCl$_3$): 8.00 (d, 2H, Ar), 7.82-7.65 (m, 2H, Ar), 7.95-7.14 (m, 19H, Ar), 6.90 (d, 2H, Ar), 5.52 (dd, 1H, H-2', J1'-2'=3.4 Hz, J2'-3'=10.1 Hz), 5.24 (d, 1H, H1'), 4.82 (s, 1H, CHPh), 4.72-4.63 (m, 2H), 4.54 (dd, 1H, H-3', J3'-4'=3.6 Hz), 4.38 (AB, 2H, CH$_2$Ar, Jgem=11.7 Hz), 3.95-3.86 (m, 2H), 3.83 (s, 3H, OCH$_3$), 3.83-3.76 (m, 1H), 3.62-3.56 (m, 1H), 3.49 (dd, 1H, J=5.9 Hz, J=9.0 Hz), 3.38 (dd, 1H, J=7.7 Hz, J=9.2 Hz), 3.37 (dd, 1H, H4',J4'-5'<1 Hz), 3.30 (dd, 1H, H1-a, Jgem=12.5 Hz, J1a,2=1.9 Hz), 3.25 (m, 1H), 2.92 (dd, 1H, H-1b, J1b,2<1), 0.88 (s, 9H, tBu).

24-b: Azide Reduction

Compound 119 [0.164 mmol] was treated according to the procedure described in General Method 3 (NB: compound smears over several minutes on HPLC column (HPLC Method A); [M+H]$^+$=1039.53. The solution of the crude product 120 was directly used for the next conversion.

24-c: Amide Coupling

Crude 120 was treated with undecanoic acid 120 mg [0.65 mmol] according to the procudure described by General Method 7.1 The residue containing 121 was purified on a silica column (gradient petrolether/ethyl acetate 2:1 to petrolether/ethyl acetate 1:1 with 2% triethylamine) to give 121 [51%]; HPLC Method A, Rt=9.14 mins; [M+Na]$^+$=1229.69, and unreacted 120 (31%).

24-d: Silylether Cleavage

To a solution of 121 in DMF [3 mL], was added a 1 molar solution of TBAF in THF [0.5 mL] and acetic acid [30 µL], and the mixture heated to 65° C. for 6 h. The reaction mixture was diluted with ethyl acetate and the solution washed with saturated sodium bicarbonate solution and water, the dried over magnesium sulfate and the solvents removed in vacuo to give crude 122 (100% conversion by ELSD); HPLC Method A, Rt=7.17 mins; [M+H]$^+$=969.55.

24-e1 to e2: Removal of Acid Labile Protecting Groups (24-e1) Crude 122 was dissolved in dry dichloromethane [5 mL] and triethylsilane [0.5 mL] and trifluoroacetic acid [0.1 mL] were added. After stirring at room temperature for 10 min conversion to 123a was complete (HPLC Method A, Rt=6.80 min, [M+H]$^+$=849.50). (24-e2). Further stirring at room temperature for 3 h gave 123 (100% conversion by ELSD); HPLC Method A, Rt=6.71 mins; [M+H]$^+$=761.43.

24-a: Glycosylation

Compound 118 [1.0 mmol] and 60 [1.5 mmol] were dissolved in dry dichloromethane [16 mL] and stirred with molecular sieves [4 Å, acid washed] at room temperature for 1 h. To the mixture was then added 2,6-di-tert.-butylpyridine [1.6 mmol] and DMTST [1.6 mmol], and the reaction stirred Selective Removal of Protecting Groups for Diversity-Part 2

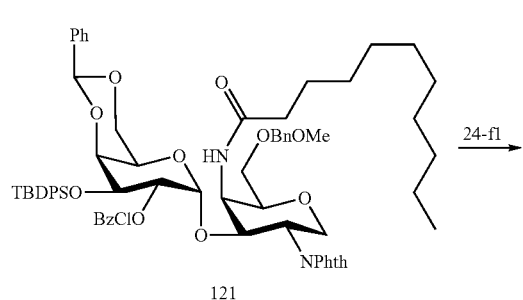
121

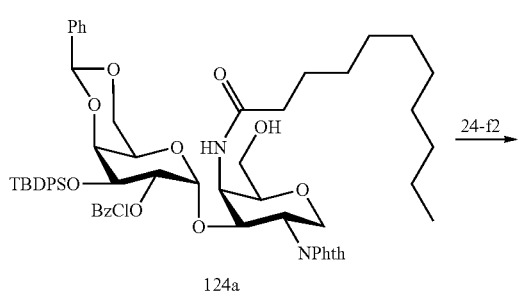
124a

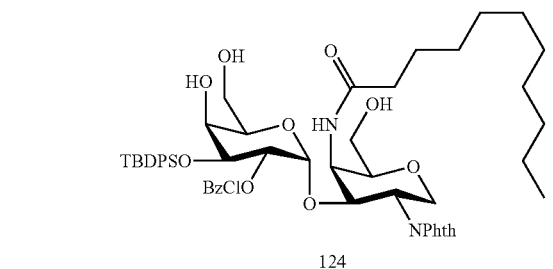
124

24-f1 to f2: Removal of Acid Labile Protecting Groups (24-f1). Compound 121 [8 μmol] was dissolved in dry dichloromethane [1 mL] and triethylsilane [0.1 mL] and trifluoroacetic acid [0.02 mL] were added. After stirring at room temperature for 2 min conversion to 124a was complete (HPLC Method A, Rt=8.54 mins, [M+H]$^+$=1187.49). (24-f2). Further stirring at room temperature for 3 hrs gave 124 (100% conversion by ELSD); HPLC Method A, Rt=7.87 mins, [M+H]$^+$=999.56.

Selective Removal of Protecting Groups for Diversity-Part 3

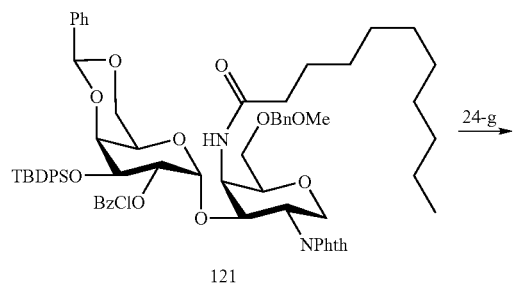
121

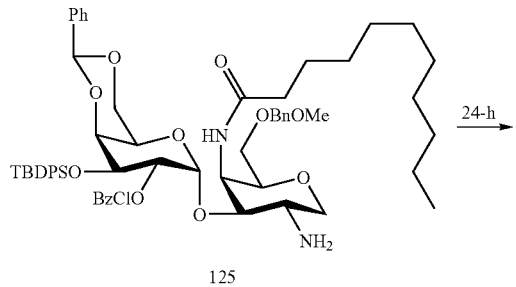
125

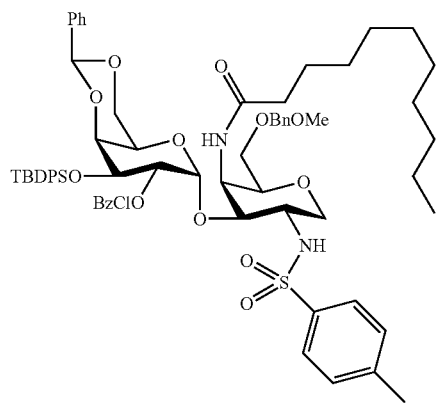
126

24-g: Phthalimido Cleavage

To a solution of 121 [0.10 mmol] in ethanol [5 mL] was added hydrazine hydrate [0.05 mL], and the solution refluxed for 20 h. The solvents were removed in vacuo and the residue co-evaporated with toluene to give crude 125 (100% conversion by ELSD). Product smears over several minutes on HPLC (HPLC Method A), [M+H]$^+$=1077.43.

24-g: Sulfonamide Formation

Compound 125 [1.8 μmol] was reacted with tosylchloride [5 mg] according to General Method 14 to give 126 (100% conversion by ELSD), HPLC Method A, Rt=9.25 mins; [M+H]$^+$=1231.65, [M+Na]$^+$=1253.63.

Selective Removal of Protecting Groups for Diversity-Part 4

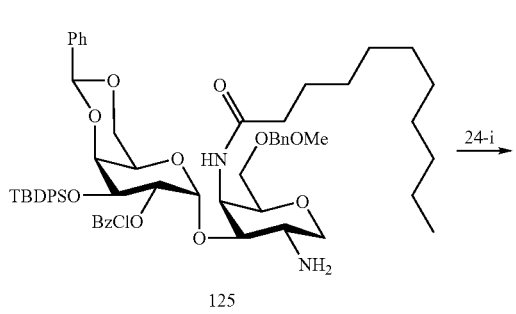
125

-continued

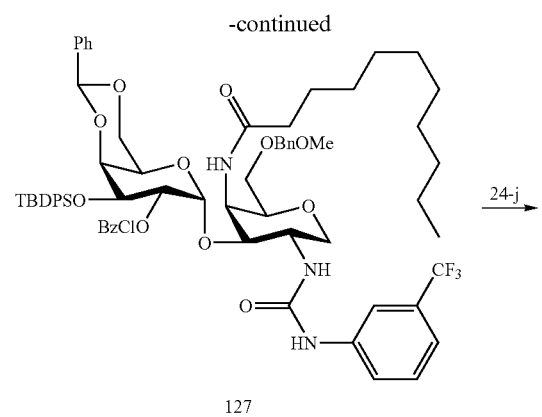

127

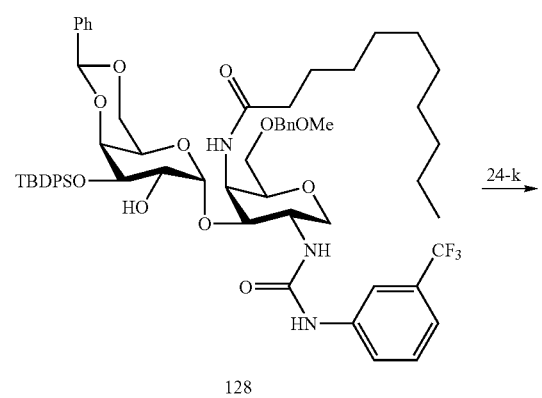

128

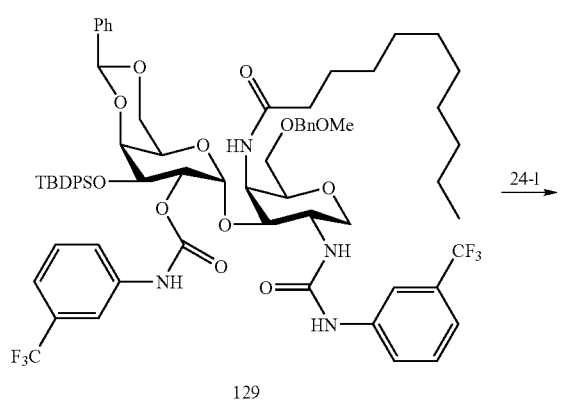

129

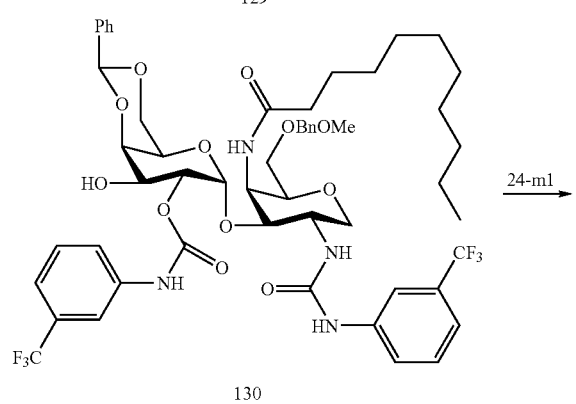

130

-continued

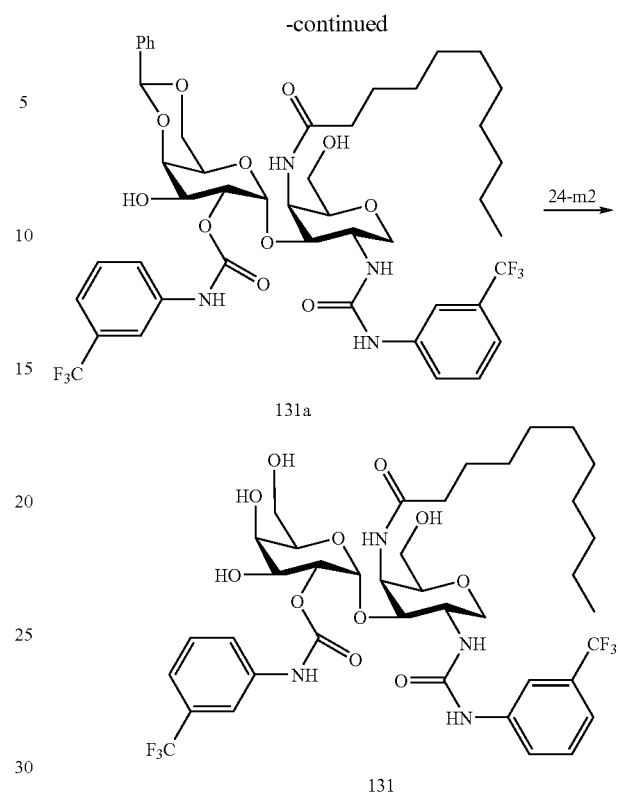

131a

131

24-i: Urea Formation

Compound 125 [0.10 mmol] was was reacted with 3-trifluoromethylphenyl isocyanate [0.4 mmol] according to General Method 1 to afford 127 (73% purity by ELSD); HPLC Method A, Rt=9.04 mins; $[M+H]^+$=1264.75.

24-j: Ester Cleavage

Compound 127 [0.10 mmol] was treated according to the procedure described in General Method 2 (with the exception that only MeOH was used as solvent) to afford crude 128; HPLC Method A, Rt=8.60 mins; $[M+H]^+$=1126.48, $[M+H]^+$=1148.46.

24-k: Carbamate Formation

To a solution of 128 [0.10 mmol] in dry DMF [5 mL], was added 3-trifluoromethylphenyl isocyanate [0.4 mmol] and DBU [45 µL], and the solution heated to 80° C. for 20 h. The reaction mixture was diluted with ethyl acetate, washed with saturated sodium bicarbonate solution and water, dried over magnesium sulfate, and the solvents removed in vacuo to give 129.

24-l: Silylether Cleavage

To a solution of 129 in DMF [3 mL], was added a 1M solution of TBAF in THF [0.5 mL] and acetic acid [30 µL], and the reaction mixture heated to 65° C. for 6 h. The reaction mixture was diluted with ethyl acetate and the solution washed with saturated sodium bicarbonate solution, water, dried over magnesium sulfate, and the solvents removed in vacuo to give crude 130.

24-m1 to 24-m2: Removal of Acid Labile Protecting Groups
(24-m1). To a solution of compound 130 in dichloromethane [5 mL] was added triethylsilane [0.5 mL] and trifluoroacetic acid [0.1 mL]. After stirring at room temperature for 2 min conversion to 131a was complete. (24-m2). Further stirring at room temperature for 3 hrs gave 131 quantitatively.
Selective Removal of Protecting Groups for Diversity-Part 5
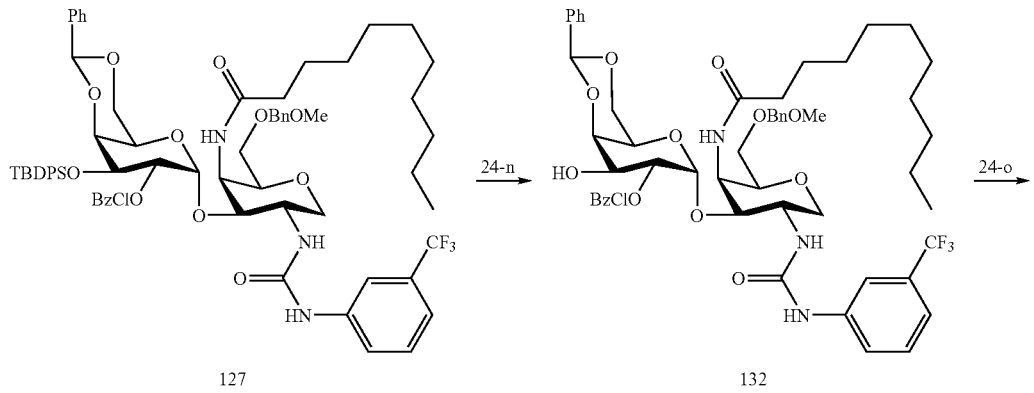
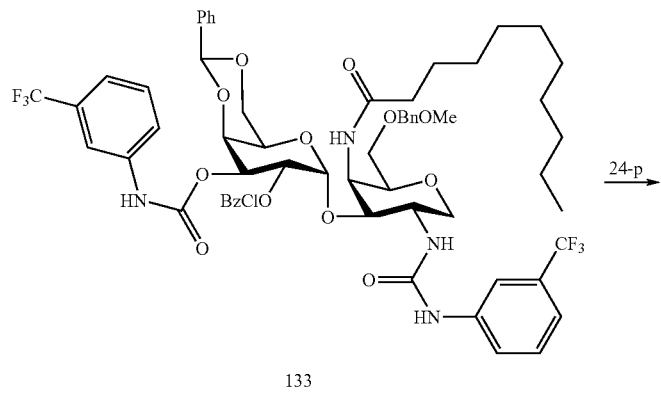
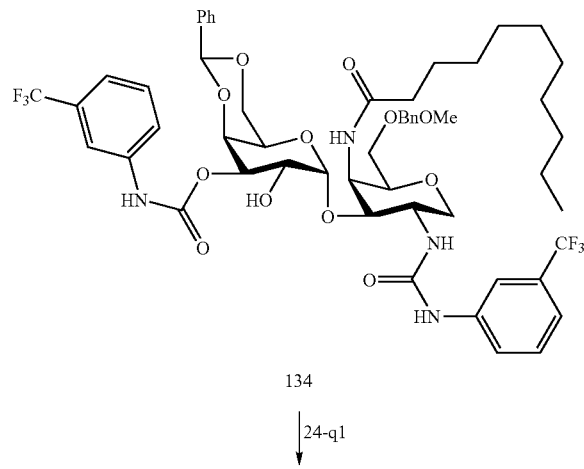

-continued

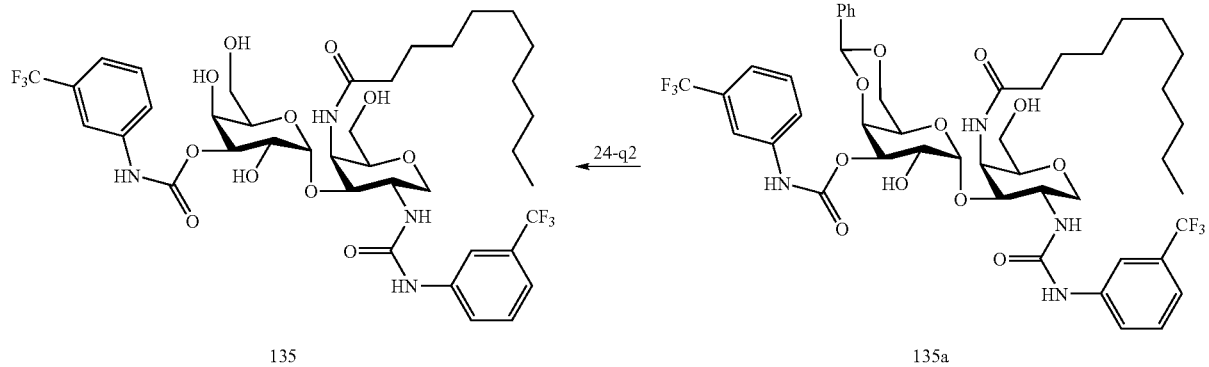

135

135a

24-n: Silylether Cleavage

To a solution of 127 in DMF [3 mL], was added a 1M solution of TBAF in THF [0.5 mL] and acetic acid [30 μL], and the mixture heated to 65° C. for 6 h. The reaction mixture was then diluted with ethylacetate and the solution washed with saturated sodium bicarbonate solution, water, dried over magnesium sulfate, and the solvents removed in vacuo to give crude 132.

24-o: Carbamate Formation

To a solution of 132 [0.10 mmol] in DMF [5 mL] was added 3-trifluoromethylphenyl isocyanate [0.4 mmol] and DBU [45 μL], and the solution heated to 80° C. for 20 h. The reaction mixture was diluted with ethyl acetate, washed with saturated sodium bicarbonate solution, water, dried over magnesium sulfate, and the solvents removed in vacuo to give 133.

24-p: Ester Cleavage

Compound 133 [0.10 mmol] was treated according to General Method 2 (with the exception that only MeOH was used as solvent) to provide crude 134.

24-q1 to 24-q2: Removal of Acid Labile Protecting Groups (24-q1). Compound 134 was dissolved in dry dichloromethane [5 mL] and triethylsilane [0.5 mL] and trifluoroacetic acid [0.1 mL] were added. After stirring at room temperature for 2 min conversion to 135a was complete. (24-q2). Further stirring at room temperature for 3 hrs gave 135.

EXAMPLE 25

Synthesis of a Beta 1→6 Linked Disaccharidic Compound For Drug Discovery-1

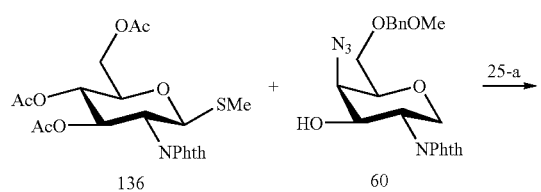

136        60

-continued

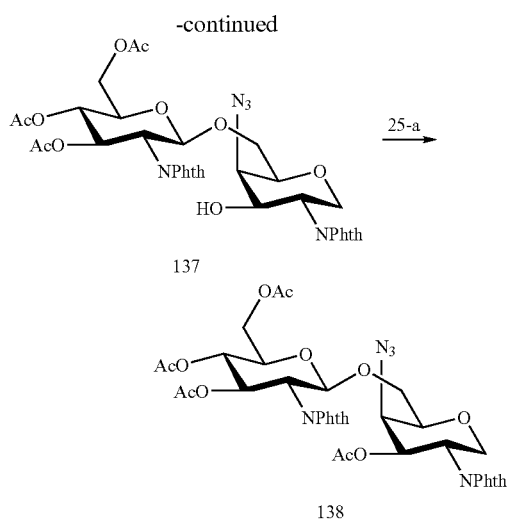

137

138

25-a: Glycosylation

To a solution of 60 [0.48 mmol] and 136 [0.70 mmol] in dichloroethane [8 mL] was added DMTST [0.48 mmol], and the mixture stirred for 45 mins at room temperature. At that time further DMTST [0.21 mmol] was added, and after stirring for 20 mins the reaction was quenched by the addition of triethylamine [0.5 mL]. The reaction mixture was then diluted with dichloromethane, washed with 10% citric acid, saturated sodium bicarbonate solution, dried over magnesium sulfate, the solvents evaporated in vacuo and the product purified by column chromatography (silica, petrol ether/ethyl acetate 1:1) to give 137 as a colorless foam [59%]; HPLC Method A, Rt=5.06 mins; [M+Na]$^+$=758.49.

25-b: Acetylation

To a solution of 137 [2 mg] in pyridine [0.2 ml] was added acetic anhydride [50 μL], and the ensuing reaction mixture stirred at room temperature for 2 hrs. The reaction mixture was then diluted with dichloromethane and washed with 10% citric acid, saturated sodium bicarbonate solution, dried over magnesium sulfate and the solvents evaporated in vacuo to give 138; $^1$H-NMR (CDCl$_3$): 7.85-7.62 (m, 8H, Ar), 5.75 (dd, 1H, H-3', $J_{2',3'}$=10.4 Hz, $J_{3',4'}$=8.8 Hz), 5.70 (dd, 1H, H-3, $J_{2,3}$=11.0 Hz, $J_{3,4}$=3.4 Hz), 5.39 (d, 1H, H-1', $J_{1',2'}$=8.7 Hz), 5.12 (dd, 1H, H-4', $J_{4',5'}$<1 Hz), 4.64 (ddd, 1H, H-2), 4.25 (dd, 1H, H-2'), 4.00 (dd, 1H, H-4), 3.88-3.76 (m, 3H, H-1a, H-5, H-5'), 3.70-3.52 (m, 5H, H-1b, H-6a, H-6b, H-6a', H-6b'), 2.07, 1.98, 1.87, 1.71 (each s, 3H, Ac).

EXAMPLE 26

Synthesis of a Beta 1→6 Linked Disaccharidic Compound For Drug Discovery-2

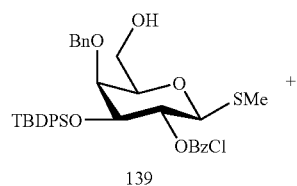

139

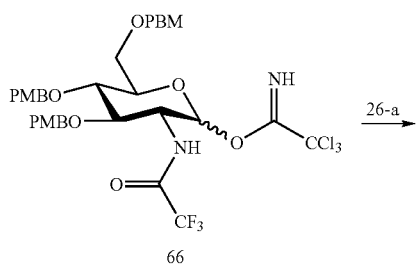

66

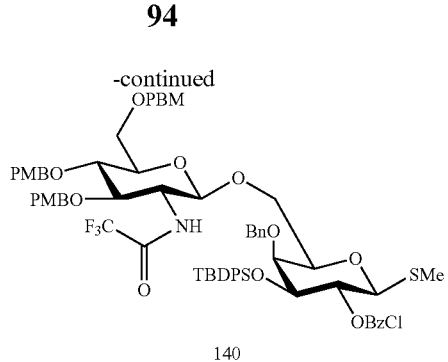

140

26a. Formation of a Beta 1→6 Linked Disaccharide

A solution of thioglycoside 139 [0.154 mmol], trichloroacetimidate 66 [1.5 eq. with respect to thioglycoside] and 4 angstrom molecular sieves [0.26 g] in 1,2-DCE [2.6 mL] was stirred at room temperature for 15 mins. At this time TMSOTf [0.3 eq.] was added. The reaction was allowed to stir for 30 mins at which time it was quenched by the addition of triethylamine [2 mL]. The reaction mixture was diluted with DCM, filtered and the resulting filtrate concentrated in vacuo to afford a residue. The residue was purified by column chromatography [toluene/acetone, 20:1] to provide the product as a colourless foam [58%]; HPLC Method A, Rt=8.02 mins; [M+Na]$^+$=1316; $^1$H-NMR, CDCl$_3$ δ4.07 (d, 1-H, H-1a $J_{1,2}$=9.2 Hz), 4.42 (d, 1-H, H-1b, $J_{1,2}$=8.2 Hz) indicating two beta linkages.

EXAMPLE 27

Synthesis of a Methyl Glycoside Disaccharide for Drug Discovery

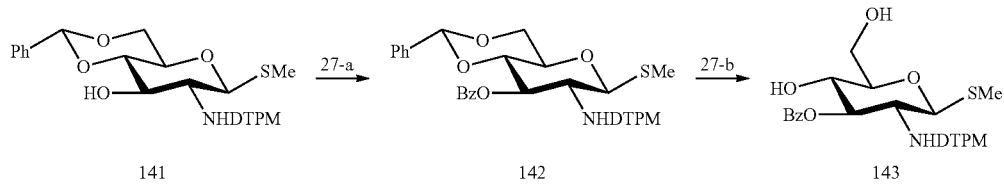

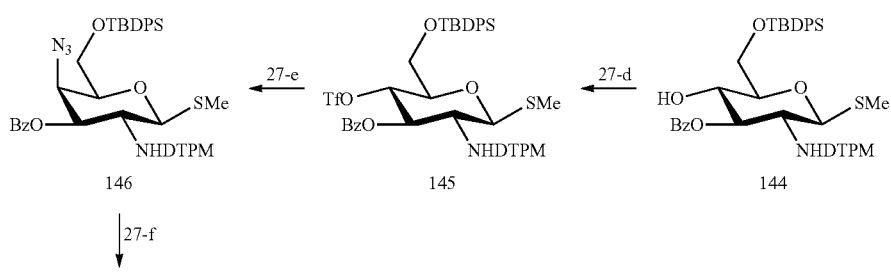

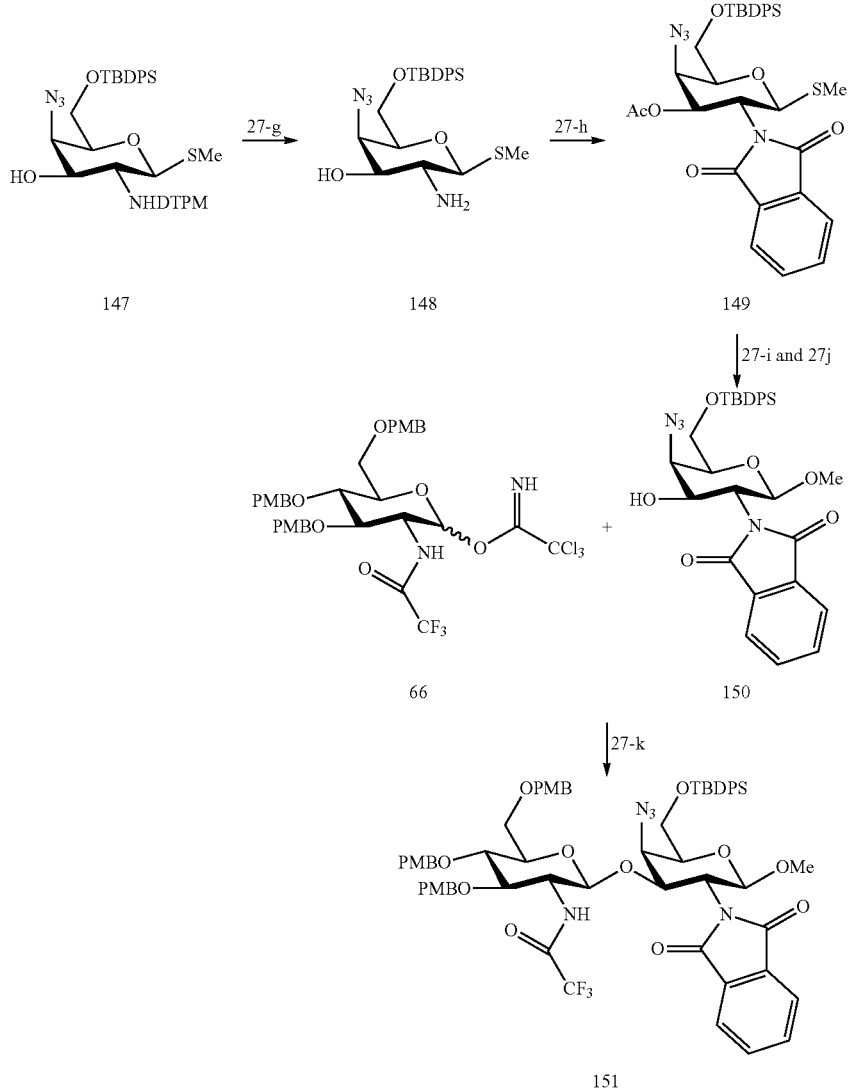

27-a. Benzoylation of the 3-OH Position

To a solution of 141 [37.2 mmol] in 1,2-dichloromethane [140 mL] at 0° C. was added DMAP [2 eq.] and benzoyl chloride [1.5 eq.]. The reaction mixture was allowed to return to room temperature, and stirred for 2 hrs. Methanol was added and the reaction mixture was stirred for a further 15 mins. The reaction mixture was then diluted with CHCl$_3$, washed with 10% citric acid solution, saturated NaHCO$_3$ solution, saturated brine solution, dried (MgSO$_4$), concentrated in vacuo. Compound was passed through a plug of silica to give 142 and used directly in the next step without further purifucation.

27-b. Benzylidene Cleavage

To a solution of thioglycoside 142 [36.7 mmol] in a mixture of MeCN/MeOH/H$_2$O [2:1:0.1, 155 mL] was added p-toluenesulphonic acid [200 mg]. The resulting reaction mixture was stirred at 75° C. for 2 hrs. The reaction was allowed to cool, to room temperature, water was added [50 mL] and the volatile solvents [MeCN and MeOH] removed in vacuo. The resulting suspension was filtered and the collected solid washed further with water followed by petroleum ether and then dried under vacuum to afford pure 143 [98%]; [M+H]$^+$= 480.3, (99.8% pure by ELSD); HPLC Method A, Rt=3.80 mins.

27-c. Sialyl Protection of a 6-OH Group

To a suspension of the diol 143 [10 mmol] in pyridine [20 mL] was added imidazole [1 mmol] and the resulting reaction mixture was then heated to 120° C. At this time TBDPS-Cl [12 mmol] was added in portions and the reaction was stirred for 1 hr at 120° C. After this time further TBDPS-Cl [0.4 eq.] was added and the reaction was allowed to stir for a further hour. The reaction mixture was then cooled, annd the volatiles removed in vacuo. The residue was taken up in DCM and washed with 1 molar HCl solution, dried (MgSO$_4$) and the solvent removed in vacuo. The residue was washed with petroleum ether to afford pure 144 as a white solid [99%]; HPLC Method A Rt=6.66 mins (100% purity by ELSD); [M+H]+=718.57.

27-d. Formation of a 4-O-Triflate

To a solution of 144 [2 mmol] in DCM [20 mL] was added pyridine [4 mmol] and the resulting mixture cooled to 0° C. At this time triflic anhydride [3.2 mmol] was slowly added and the reaction mixture was then allowed to return to room temperature. The reaction was allowed to stir for one hour at room temperature at which time it was diluted with DCM and washed with a solution of 0.5 molar HCl, dried ($MgSO_4$) and the solvent removed in vacuo to afford pure 145 [100%]; HPLC Method A, Rt=7.63 mins; [M+H]+=850.66.

27-e. Formation of an Axial Azido Derivative

To a solution of triflate 145 [1 mmol] in DMF was added $NaN_3$ [3 mmol] and the resulting reaction mixture was allowed to stir at room temperature for 10 hrs. The reaction mixture was concentrated in vacuo, and the residue washed with water followed by petroleum ether. The solid was then dried to provide the product 146 [99%]; HPLC Method A, Rt=7.23 mins; [M+H]+=743.5.

27-f. Removal of a Benzoyl Group by Transesterification

Compound 147 was prepared according to the procedure described in General Method 2 and purified by column chromatography [30% ethyl acetate/petroleum ethers] to afford a white solid [83%]; HPLC Method A, RT=6.53 min; [M+H]+=639.2.

27-g. Deprotection of the 2-Amino Group

To a solution of the sugar 147 [4.29 mmol] in DMF/MeOH [1:2, 45 mL] at room temperature was added hydrazine hydrate [0.52 mL]. The reaction mixture was stirred for two hours at which time it was filtered and the filtered solid washed with methanol. The filtrates were combined, the solvents removed in vacuo, residue taken up in $CHCl_3$, washed with saturated brine, dried ($MgSO_4$), and the solvent again removed in vacuo to provide a white solid 148 [88%]; HPLC Method A, Rt=5.96 mins; [M+H]+=473.3.

27-h. Reprotection of the 2-Amino Group

To a solution of the sugar 148 [0.22 mmol] in MeOH [1.25 mL] was added phthalic anhydride [0.4 mmol] and triethylamine [1 drop] and the solution was allowed to stir overnight. The reaction mixture was then concentrated in vacuo. The residue was the dissolved in dry pyridine [0.25 mL], cooled to 0° C., and acetic anhydride [60 μL] added dropwise. The reaction was allowed to stir overnight. The reaction was then concentrated, the residue taken up in $CHCl_3$ and washed with 10% citric acid solution, saturated sodium bicarbonate solution, saturated brine solution, dried ($MgSO_4$), the solvent removed in vacuo, and the residue purified by column chromatography [20% ethyl acetate/petroleum ethers] to afford the product as a white solid 149 [64%]; HPLC Method A, Rt=7.29 mins; [M+H]+=645.35.

27-i. Glycosylation to Form the O-Methyl Glycoside

To a solution of the sugar 149 [0.775 mmol] in DCM [5 mL] was added 3 angstrom molecular sieves, MeOH [12 mmol] and finally DMTST [2.32 mmol]. The reaction mixture was allowed to stir for 30 mins at which time the reaction was quenched with triethylamine [2.37 mmol], filtered and the filtrate concentrated in vacuo. The residue was taken up in DCM and washed with water, 10% citric acid solution, saturated sodium hydrogen carbonate solution, saturated brine, dried ($MgSO_4$) and the solvent removed in vacuo to provide a yellow oil. The oil was purified by column chromatography [20% ethyl acetate/petroleum ethers] to provide the product as a yellow oil [79%]; HPLC Method A, Rt=7.20 mins; [M+Na]+=651.3.

27-j. Zemplen Deprotection

Compound 150 was prepared according to the procedure described in General Method 2 and was purified by column chromatography [25% ethyl acetate/petroleum ethers] as a white solid [67%]; HPLC Method A, Rt=6.88 mins; [M+Na]+= 609.7.

27-k. Formation of an O—Me Glycoside, Beta 1-3 Linked Disaccharide

Donor 60 [0.128 mmol] and acceptor [85.2 mmol] were dissolved 1,2-DCE [1.0 mL]. 4 Angstrom molecular sieves were added and the mixture was stirred for 15 mins. TMSOTf [2.8 μmol] was then added and the reaction left to stir for 90 mins. The reaction mixture was then quenched with triethylamine, diluted with $CHCl_3$, washed with saturated $NaHCO_3$ solution, dried ($MgSO_4$) and the solvents removed in vacuo. The residue was purified by column chromatography to afford 151 [20%]; HPLC Method A, Rt=7.60 mins; [M+Na]+= 1226.67

EXAMPLE 28

Formation of Alternatively Linked Disaccharide Scaffolds

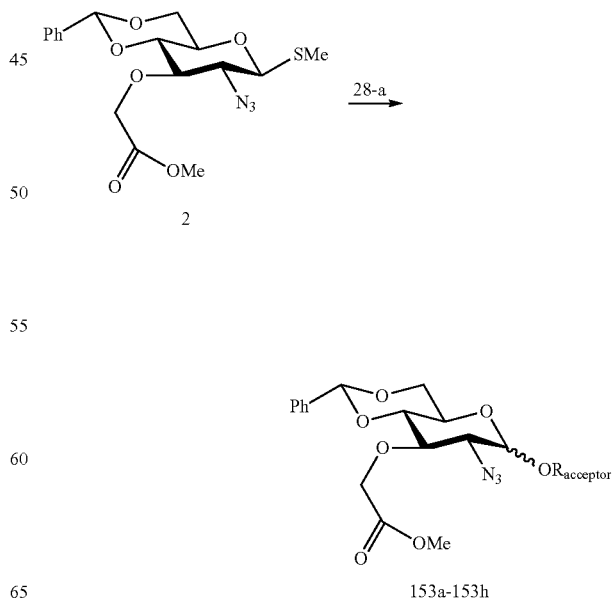

28-a. Glycosylation with a Trichloroacetimidate Donor to Afford Disaccharides (153-a to 153-h)

To solutions of the acceptor molecules 152a-152h (1.8 mmol) and the donor 2 (2.7 mmol) in dry 1,2-dichloroethane (84 mL) is added 3A acid-washed molecular pellets (4 g) and the resulting mixture stirred for 20 min. To the mixture was then added Methyl Triflate (1.8 mL of a 0.1M solution in dry 1,2-dichloroethane, 0.18 mmol) and the reaction then stirred for 30 mins. After this time triethylamine (6 mL) was added and the suspension filtered, washed with dichloromethane and all solvent removed in vacuo. This residue was purified by column chromatography to yield the title compounds as indicated in table 3 below.

TABLE 3

Disaccharide Products From Glycosylation with Donor 2

| Acceptor | Product |
|---|---|
| 152a | 153a |
| 152b | 152b |
| 152c | 153c1, 153c2 |

TABLE 3-continued
Disaccharide Products From Glycosylation with Donor 2
| Acceptor | Product |
|---|---|
| 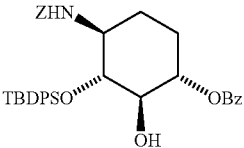<br>152d | 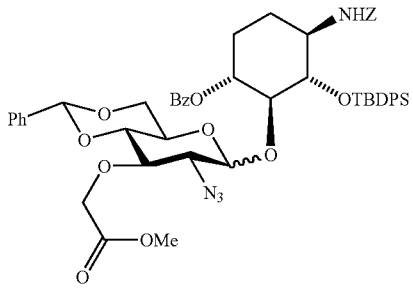<br>153d |
| 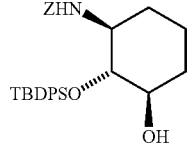<br>152e | 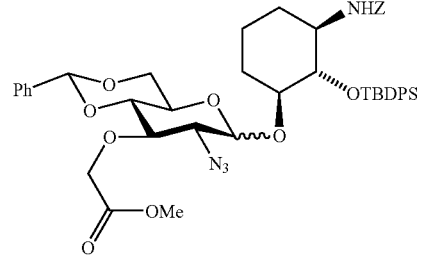<br>153e |
| 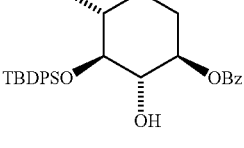<br>152f | 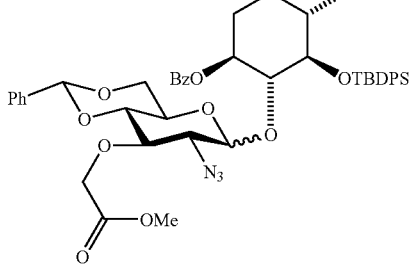<br>153f |

TABLE 3-continued

Disaccharide Products From Glycosylation with Donor 2

| Acceptor | Product |
|---|---|
| 152g | 153g |
| 152h | 153h |

28-b. Azide Reduction and Deprotection (154a-154h)

Compounds 153a-153h are hydrogenolysed at 60 psi for 1 hour with catalytic 10% palladium on activated charcoal in ethanol, to yield upon filtration and evaporation, the corresponding diamines in which the benzylidene ring has also been cleaved as indicated in the table below. These diamines may be used in their crude form for further reactions.

154a

154b

154c1

154c2

154d

154e

154f

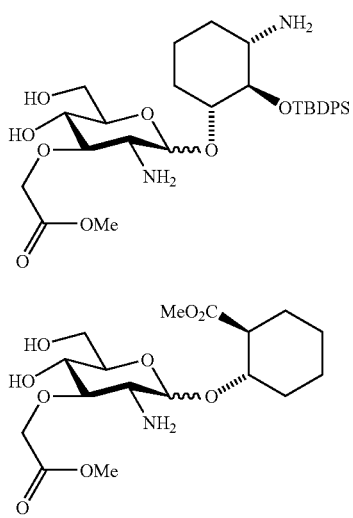

154g

154h

28-c. Amide Formation-HBTU Coupling (155a-155h)

Compounds 155a(i)-155a(iv) to 155h(i)-155h(iv) are prepared by reaction of the diamines 154a to 154h with carboxylic acids according to the procedure described in General Method 4 in a combinatorial manner. This every diamine may be reacted with an excess of every carboxylic acid to produce the bis-amide products.

TABLE 4

Acids i–iv Shown Below Are Reacted with Diamines to Give Products as Listed

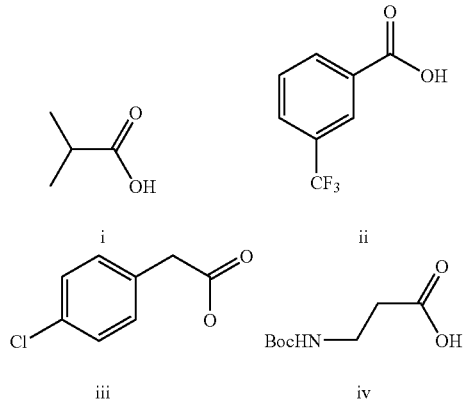

i      ii      iii      iv

| Diamine | Acids | | | |
|---|---|---|---|---|
|  | i | ii | iii | iv |
| 154a | 155a(i) | 155a(ii) | 155a(iii) | 155a(vi) |
| 154b | 155b(i) | 155b(ii) | 155b(iii) | 155b(vi) |
| 154c1 | 155c1(i) | 155c1(ii) | 155c1(iii) | 155c1(vi) |
| 154c2 | 155c2(i) | 155c2(ii) | 155c2(iii) | 155c2(vi) |
| 154d | 155d(i) | 155d(ii) | 155d(iii) | 155d(vi) |
| 154e | 155e(i) | 155e(ii) | 155e(iii) | 155e(vi) |
| 145f | 155f(i) | 155f(ii) | 155f(iii) | 155f(vi) |

TABLE 4-continued

Acids i–iv Shown Below Are Reacted with Diamines to Give Products as Listed

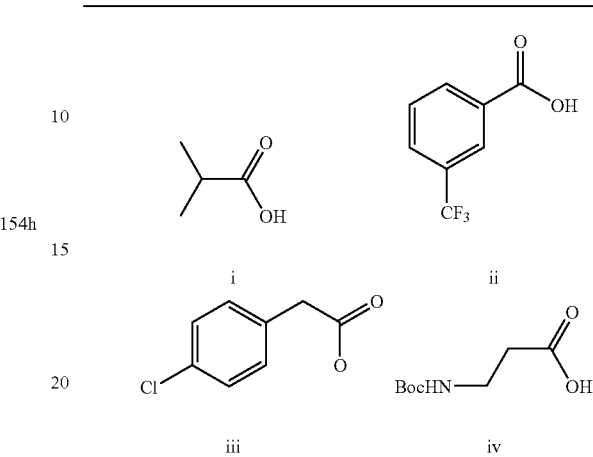

i      ii      iii      iv

| Diamine | Acids | | | |
|---|---|---|---|---|
|  | i | ii | iii | iv |
| 154g | 155g(i) | 155g(ii) | 155g(iii) | 155g(vi) |
| 154h | 155h(i) | 155h(ii) | 155h(iii) | 155h(vi) |

Examples of Table 4

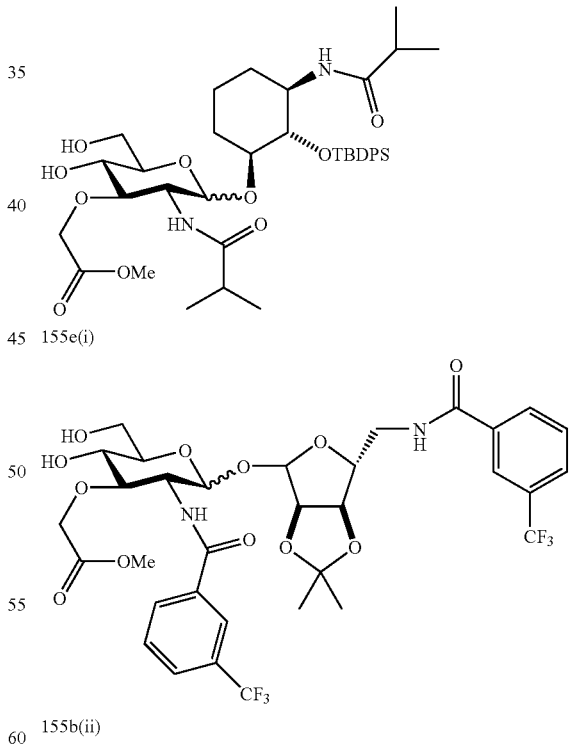

155e(i)

155b(ii)

28-d. Silyl Deprotection

The t-butyldiphenylsilyl groups are removed from Compounds 155 (as appropriate) by treatment of the silylated compound in N,N-dimethylformamide with tetrabutylammo-

EXAMPLE 29

Formation of Alternatively Amide Linked Disaccharide Scaffolds

Reduction of an Azide to an Amine

Amino sugars can be obtained by reduction of corresponding azido sugars according to the procedure described in General Method 3. Alternatively, the azide may be reduced selectively by hydrogenolysis at atmospheric pressure over 5% palladium on charcoal in methanol for 30 minutes. This latter method is suitable for the reduction of azides in the presence of benzyl ethers. Filtration of the solution and removal of the solvents in vacuo yields the crude aminosugar suitable for further reaction. Hydrogenolysis is also employed to remove the carbobenzyloxy group from compound 152d (see Amines Used in Example 28).

Formation of an Anhydride and Reaction with an Amine

Anhydrides are formed according to the following general method. Azaleic acid monomethyl ester, suberic acid monomethyl ester or fumaric acid monoethyl ester [2 equivalents] are dissolved in anhydrous dichloromethane to form a 10 millilolar solution. To this solution is added diisopropylcarbodiimide [1 equivalent] and triethylamine [1 equivelant] and the solution stirred at room temperature for 45 minutes. After this time, the solution of acid anhydride is evaporated, redissolved in N,N-dimethylformamide to form a 10 millimolar solution and added to a solution of the crude sugar amine (selected from Amines Used in Example 28) in N,N-dimethylformamide. The reaction mixture is stirred for 1 hour. The reaction mixture is quenched with water, acidified to pH 4 and extracted with ethyl acetate and back extracted with 10% sodium hydrogen carbonate solution to yield the crude sugar amide. The solvents are removed in vacuo and the esters hydrolysed by the addition of 5 equivelant of lithium hydroxide to an wet methanolic solution of the crude ester. Acidification of this mixture followed by removal of the solvents in vacuo yields the crude half acid amide which is partially purified by passing through a short bed of silica gel. This crude material in which all other protecting esters have been cleaved is suitable for further reaction. Compounds formed by this process are displayed in Half Acid Amides formed in Example 29 below.

Formation of a Dimeric Derivative

The crude sugar half acid amide, is then dissolved in N,N-dimethylformamide and treated with 1 equivalent of ethyl diisopropylamine, 1 equivelant of HBTU and finally 1.3 equivalents of the crude sugar amine. The reaction mixture is stirred for 30 to 60 minutes at room temperature, quenched by the addition of water and solvents removed in vacuo. The crude residue is finally purified by mass based fractionation to furnish the desired bis amide linked scaffolds. A combinatoral matrix of acid and amine results in a wide diversity of bis amide linked scaffolds as exemplified in Table 5.

Amines Used in Example 29:

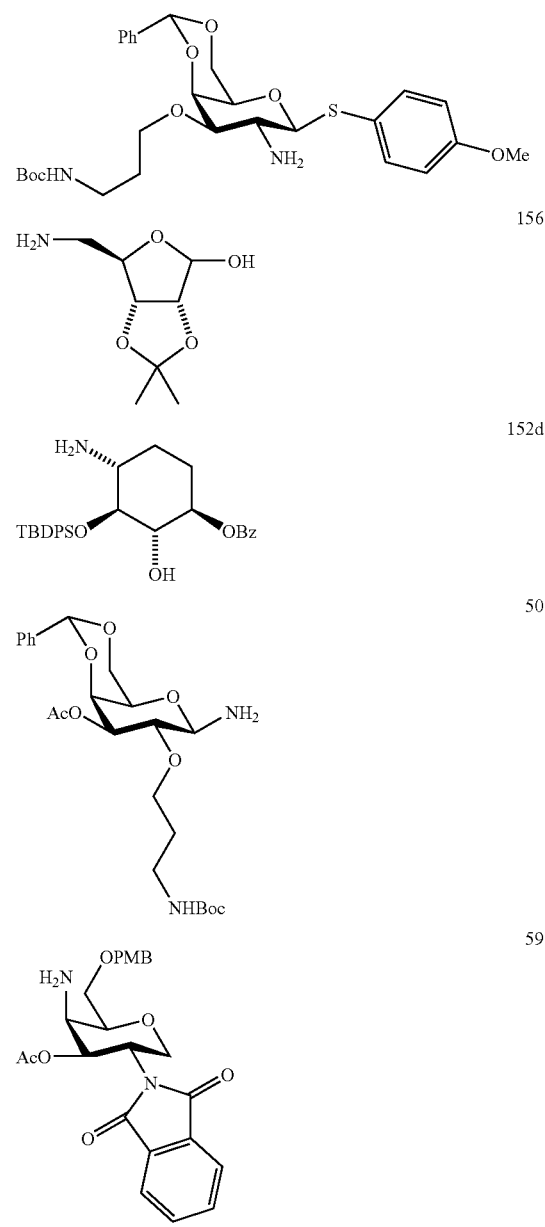

Half Amines used in Example 29:

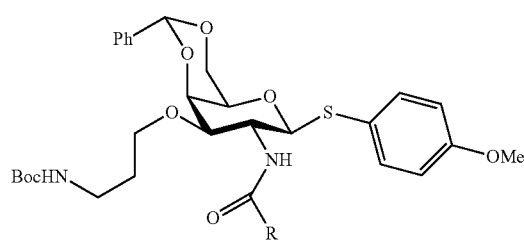

-continued

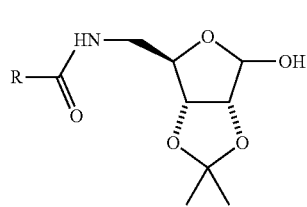
158A-C

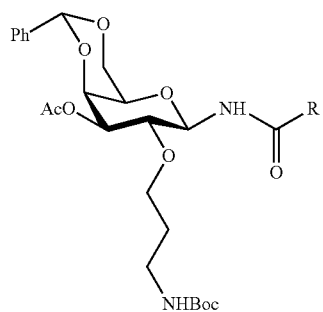
159A-C

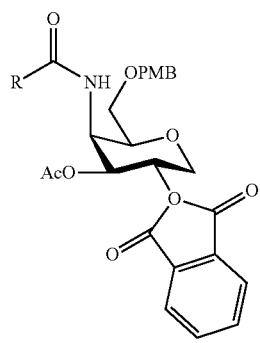
160A-C

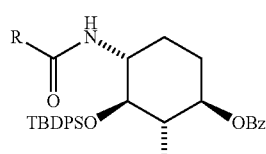
161A-C

Where R = A

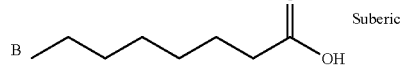
B    Suberic

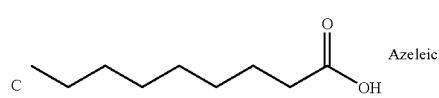
C    Azeleic

TABLE 5

Products Resulting From Reaction of Compounds From "Amines used in Example 29" with "Half Acid Amides formed in Example 29"

|      | Amine  |        |      |    |      |
|------|--------|--------|------|----|------|
| Acid | 13     | 156    | 50   | 59 | 152d |
| 157A | 157A13 |        |      |    |      |
| 157B | 157B13 |        |      |    |      |
| 157C | 157C13 |        |      |    |      |
| 158A | 158A13 | 158A156 |     |    |      |

TABLE 5-continued

Products Resulting From Reaction of Compounds From "Amines used in Example 29" with "Half Acid Amides formed in Example 29"

|      | Amine  |        |       |       |         |
|------|--------|--------|-------|-------|---------|
| Acid | 13     | 156    | 50    | 59    | 152d    |
| 158B | 158B13 | 158B156 |      |       |         |
| 158C | 158C13 | 158C156 |      |       |         |
| 159A | 159A13 | 159A156 | 159A50 |     |         |
| 159B | 159B13 | 159B156 | 159B50 |     |         |
| 159C | 159C13 | 159C156 | 159C50 |     |         |
| 160A | 160A13 | 160A156 | 160A50 | 160A59 |       |
| 160B | 160B13 | 160B156 | 160B50 | 160B59 |       |
| 160C | 160C13 | 160C156 | 160C50 | 160C59 |       |
| 161A | 161A13 | 161A156 | 161A50 | 161A59 | 161A152d |
| 161B | 161B13 | 161B156 | 161B50 | 161B59 | 161B152d |
| 161C | 161C13 | 161C156 | 161C50 | 161C59 | 161C152d |

Example structures from Table 5:

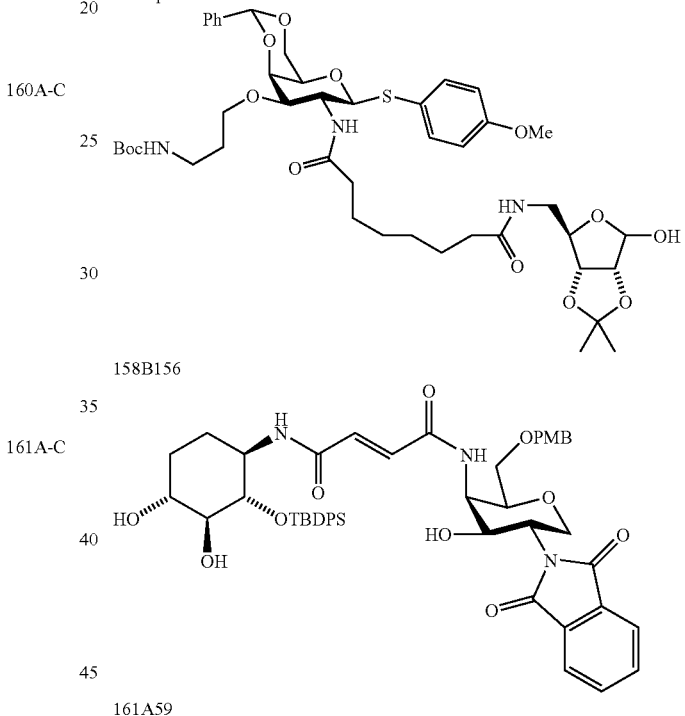

158B156

161A59

EXAMPLE 30

Formation of Amide Linked Disaccharide Scaffolds

Glucuronic acid 14, is dissolved in N,N-dimethylformamide to form a 10 millimolar solution. To this solution is added triethylamine [1.1 equivalents] followed by HBTU [1.05 equivalents. The mixture is stirred for 3 minutes at room temperature, after which time a concentrated solution of the amine [20-30 millimolar; 1 equivalent], as prepared in Example 29 [amines 13, 156, 152d, 50 and 59] is rapidly added. The reaction mixture is stirred for a further 45 minutes, then quenched with an equal volume of 10% citric acid in water, and extracted with ethyl acetate. The organic layers are dried over magnesium sulfate and solvents removed in vacuo to yield the crude product which is further purified by column chromatography, to yield the desired product.

Reaction Products:
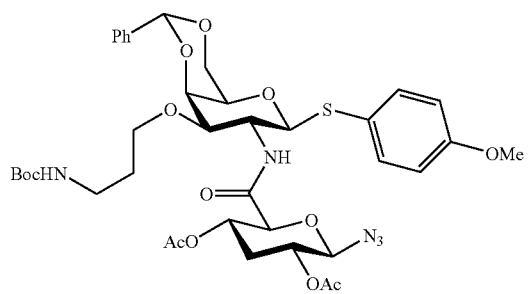
162
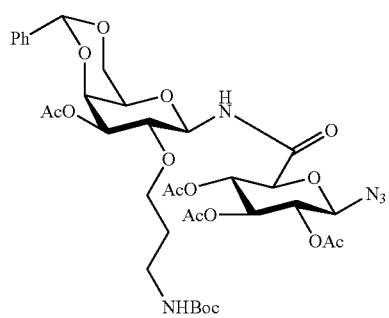
162
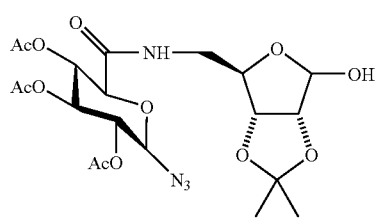
164
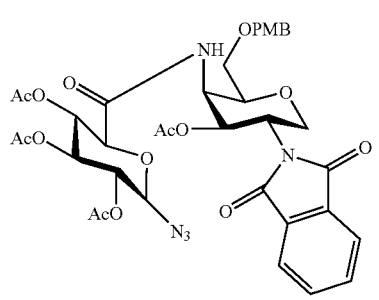
165
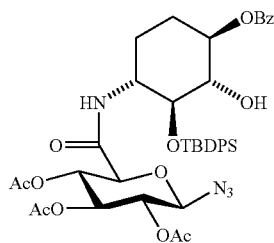
166
The Boc, isopropylidene and benzylidene protecting groups may be removed by treatment with TFA according to general procedure 5, acetate and benzoate protecting groups are removed according to general procedure 2.
EXAMPLE 31
Synthesis of an Alkylated 2-Deoxy-2-Amino Disaccharidic Compound
109-03
↓ 31-a
167
↓ 31-b -continued

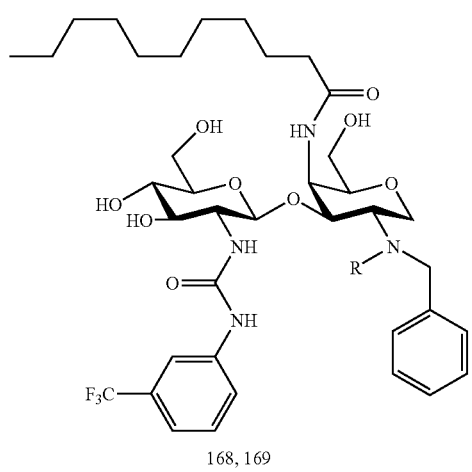

168, 169

31-a and 31-b. N-Alkylation (31-a). To a solution of the sugar 109-03 [7.4 mg] in THF/MeOH [84 μL/9.4 μL] was added benzaldehyde [0.71 μL] and the mixture stirred for 2 hrs at room temperature. To the mixture was then added acetic acid [0.5 μL] and NaCNBH$_3$ [0.8 mg] and the reaction was allowed to stir overnight at room temperature. The reaction was neutralised and concentrated in vacuo. The residue was taken up in DCM and washed with a saturated brine solution, dried (MgSO$_4$) and the solvent removed in vacuo. (31-b). The residue was treated with Ac$_2$O/pyridine [1:3] solution for two hours for the purpose of analysis; HPLC Method A, Rt (168 monobenzylated-monoacetylated)=7.56 mins, (169 bis-benzylated)=8.77 mins; mono-benzylated-mono-acetylated [M+H]$^+$=1391.9, bis-benzylated [M+H]$^+$=1339.9.

EXAMPLE 32

Synthesis of Benzimidazole Compounds

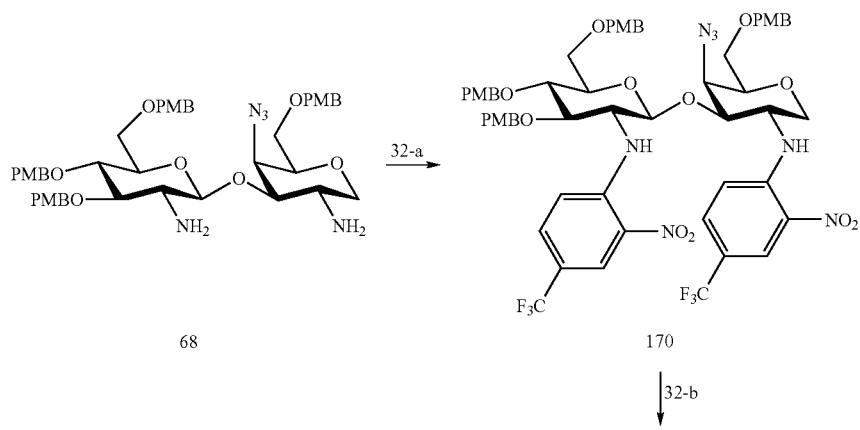

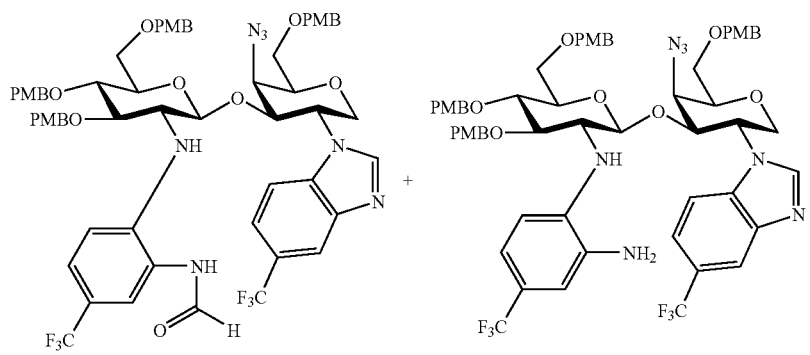

32-a. Fluorine Displacement

A solution of 3-fluoro-2-nitro-trifluoromethylbenzene [0.0715 mmol], triethylamine [0.0861 mmol] in DMF [250 μL] was added to a flask containing diamine 68 [0.0241 mmol]. The resulting reaction mixture was then stirred at 50° C. for 16 hrs. At this time the reaction was allowed to cool and the product was purified by preparative TLC [mobile phase ethyl acetate]. The product was collected in quantitative yield; HPLC Method A, Rt=7.51 mins; [M+Na]$^+$=1230.6

32-b. Formation of Benzimidazole

A solution of SnCl$_2$ [300 μL of SnCl$_2$.H$_2$O at 0.32 molar in DMF] was added to a flask containing compound 170 [2.48 μmol]. The reaction mixture was then stirred at 80° C. for 16 hrs. The reaction mixture was diluted with EtOAc/H$_2$O [1:1, 5 mL], filtered through a pad of celite. The filtrated was separated into aqueous and organic layers and the organic layer washed with H$_2$O, dreid (MgSO$_4$) and the solvent removed in vacuo to afford a mixture of products 171 and 172; HPLC Method A, Rt (171)=7.18 mins, Rt (172)=7.41 mins; [M+H]$^+$(171)=1186.8, [M+H]$^+$(172)=11.58.8.

EXAMPLE 33

Synthesis of a N-Acetyl-Lactosamine Based Library of 6'-Hydroxy Phosphonates

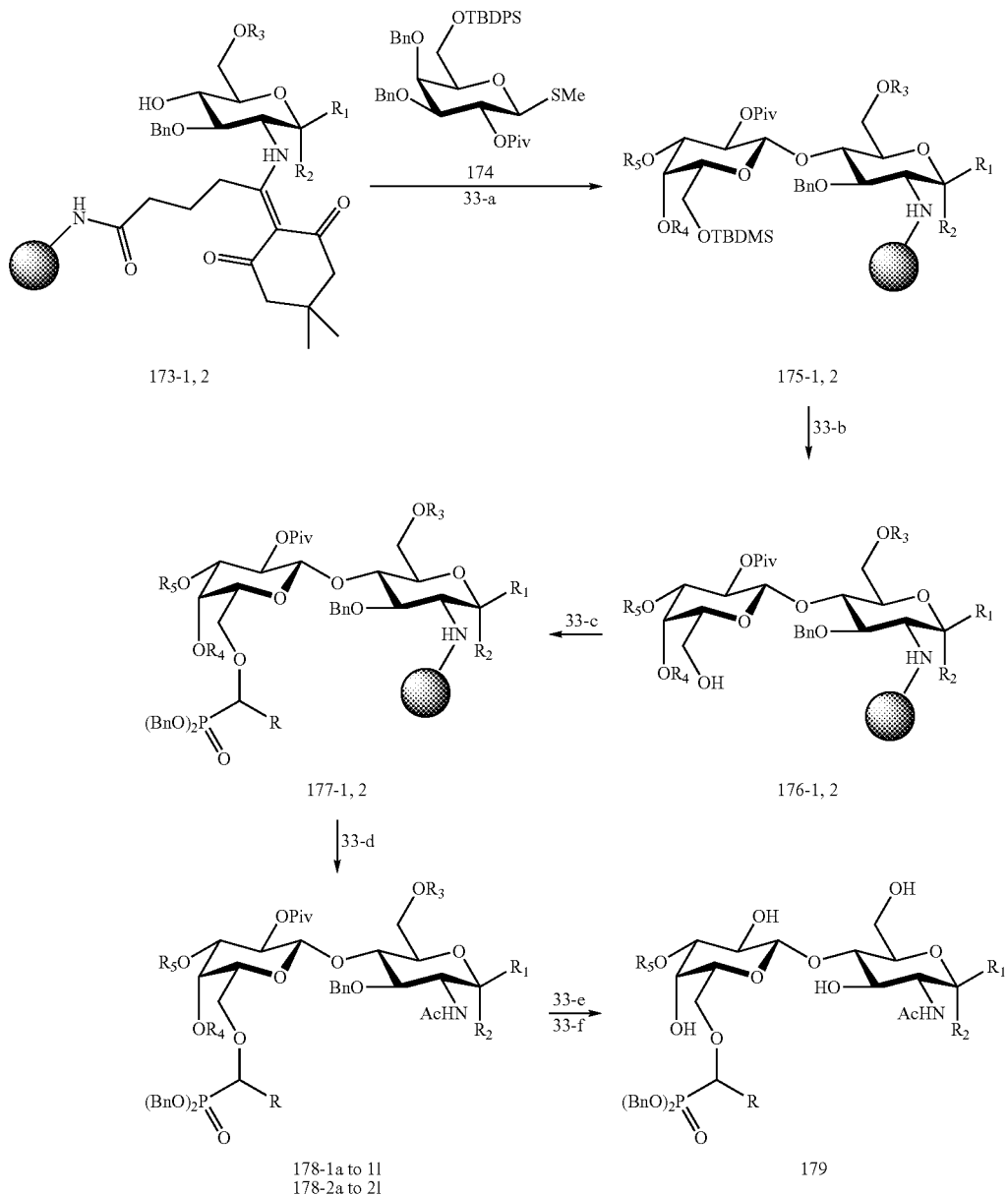

For compounds 173-1, 175-1, 176-1, 177-1 and 178,1 R$_1$ = OBn and R$_2$ = H
For compounds 173-2, 175-2, 176-2, 177-2 and 178-2, R1 = H and R2 = OMe Reactions were carried out in identical series for resins 174-1 and series 174-2. After step 33). After step 33-b each series was divided into 12 portions for the individual alkylations.

Alkylating Agents for Example 33, Where R=Sulphonate or R=Halide.

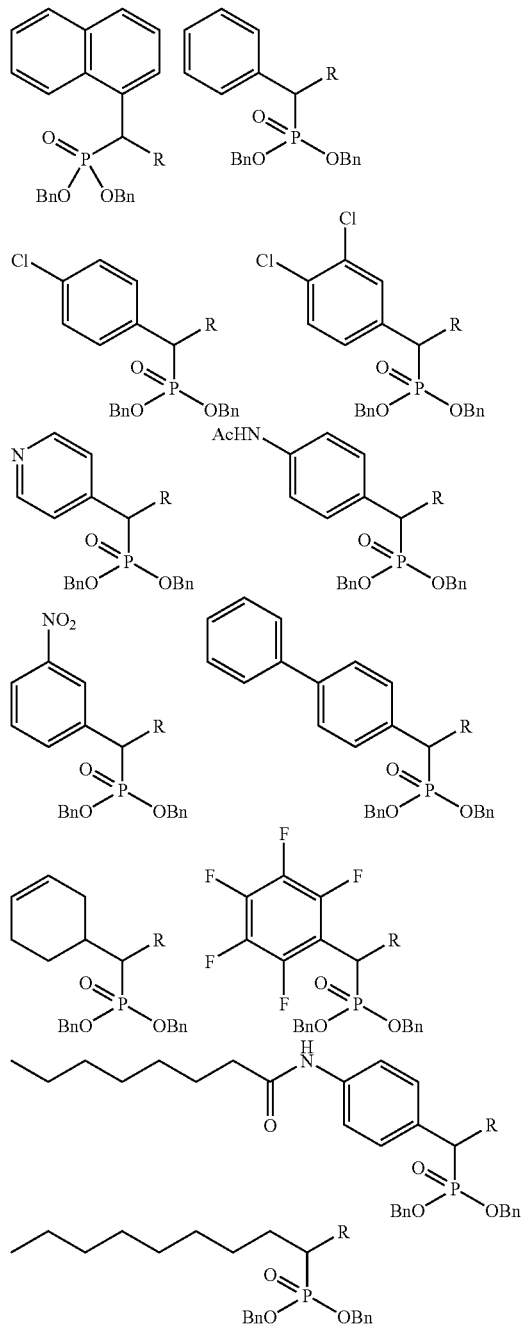

33-a. Glycosylation

Resin [0.47 mmol] was weighed into a reactor and molecular sieves [200 mg], thioglycoside donor sugar 174 [2.35 mmol] and dichloromethane [~1.5 mL] was added. To the mixture was then added DMTST [2.35 mmol]. The reaction vessel was sealed, shaken and reacted for 5 hours. At this time the reaction was then quenched by the addition of triethylamine, and the molecular sieves removed from the resin. The resin was then washed with DMF, MeOH/CHCl$_3$ (1:1) and dichloromethane. The resin was then dried under vacuum.

33-b. Solid Phase Silylether Deprotection

A solution of PSHF (proton sponge hydrogen fluoride) (0.5 Molar in DMF/Acetic Acid, 95:5) was prepared. The resins [1.41 mmol] was added to the solution and the reaction was stirred at 65° C. for 24 hours. The resin was then washed with DMF, MeOH/CH$_3$COOH/THF, 1:1:8, THF and DCM, and then dried under high vacuum.

33-c. Solid Phase Alkylation

Resins 176 [0.047 mmol] were individually reacted with a 0.25 molar solution of tert-butoxide in DMF (5 min) and then an alkylating agent (see above), [0.25 molar of alkylating agent in DMF, 20 min] was reacted with the resin. The resins were washed with DMF and again treated with the two solutions, this procedure was repeated a further four times. The final wash of the resins was performed as above; with DMF, THF/MeOH/CH$_3$CO$_2$H (8:1:1), THF, DCM and MeOH. The resins were then dried overnight.

33-d. Cleavage of Disaccharide From Resin

The resins 177 [0.047 mmol] were separately treated with a 7% hydrazine hydrate/DMF solution [2 mL] overnight. The resin was filtered and the resin washed with DMF. The filtrates were combined and the solvent removed in vacuo. The residue was taken up in DCM and washed with water and saturated brine solution, dried (MgSO$_4$) and the solvent removed in vacuo. The residue was then treated with a solution of Ac$_2$O/pyridine [1 mL, 1:3] for three hours. The Solvents were removed in vacuo and the product purified by column chromatography.

33-e. Removal of the Pivaloyl Protecting Group

To a solution of NaOMe/MeOH/THF [2 mL, ~2 molar] was added the pivaloyl protected disaccharide 178 [0.03 mmol]. The reaction mixture was heated at reflux until TLC indicated the reaction was complete. At completion, reaction mixture pH was reduced to ~5 with amberlite IR-120-H$^+$ resin. The reaction was filtered, and the solvent concentrated in vacuo.

33-f Deprotection of Hydroxyphosphonates and Benzyl Ether Cleavage

Compound 178 (after 33-e) [0.0193 mmol] was dissolved in dry dichloromethane [2 mL] under a nitrogen atmosphere, the solution cooled to 0° C. and trimethylsilyl bromide [0.097 mmol] was added. After stirring at 0° C. for 30 mins a solution of ammonia in methanol [12 μL of 28%aq ammonia in 20 mL methanol] was added. The solvents were removed to give the crude free hydoxyphosphonate as an ammonium salt. Final products were purified by mass fractioning HPLC.

TABLE 6

Final products Synthesised in Example 33.

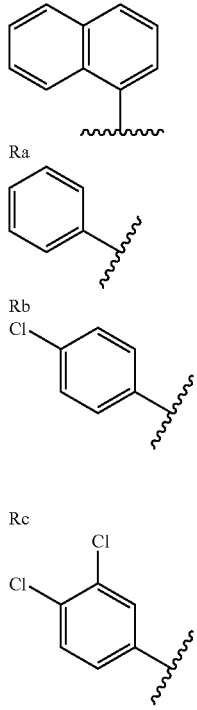

| Comp. No. | R | R1 | R2 | Note |
|---|---|---|---|---|
| 179a | Ra | H | OMe | |
| 179b | Rb | H | OMe | |
| 179c | Rc | H | OMe | |
| 179d | Rd | H | OMe | |
| 179e | Re | H | OMe | |
| 179f | Rf | H | OMe | |
| 179g | Rg | H | OMe | |
| 179h | Rh | H | OMe | |
| 179i | Ri | H | OMe | |
| 179j | Rj | H | OMe | |
| 179k | Rk | H | OMe | |
| 179l | Rl | H | OMe | |
| 179m | Ra | H, OH | OH, H | Anomeric lactol |
| 179n | Rb | H, OH | OH, H | Anomeric lactol |
| 179o | Rc | H, OH | OH, H | Anomeric lactol |
| 179p | Rd | H, OH | OH, H | Anomeric lactol |
| 179q | Re | H, OH | OH, H | Anomeric lactol |
| 179r | Rf | H, OH | OH, H | Anomeric lactol |
| 179s | Rg | H, OH | OH, H | Anomeric lactol |
| 179t | Rh | H, OH | OH, H | Anomeric lactol |
| 179u | Ri | H, OH | OH, H | Anomeric lactol |
| 179v | Rj | H, OH | OH, H | Anomeric lactol |
| 179w | Rk | H, OH | OH, H | Anomeric lactol |
| 179x | Rl | H, OH | OH, H | Anomeric lactol |

Side Arms for Table 6

TABLE 6-continued

Final products Synthesised in Example 33.

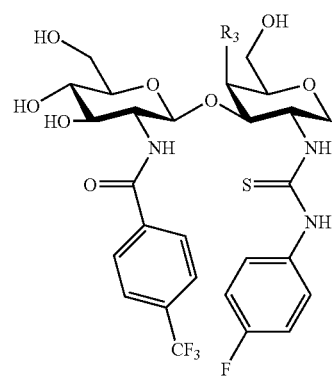

| Comp. No. | R | R1 | R2 | Note |
|---|---|---|---|---|

Rk ~~~~~~~~~~ (decyl chain)

Rl

EXAMPLE 34

Preparation of Guanidine

Scheme 4: (a) general method 12 (b) NH$_4$OH (aqu.)/MeOH (1:1)

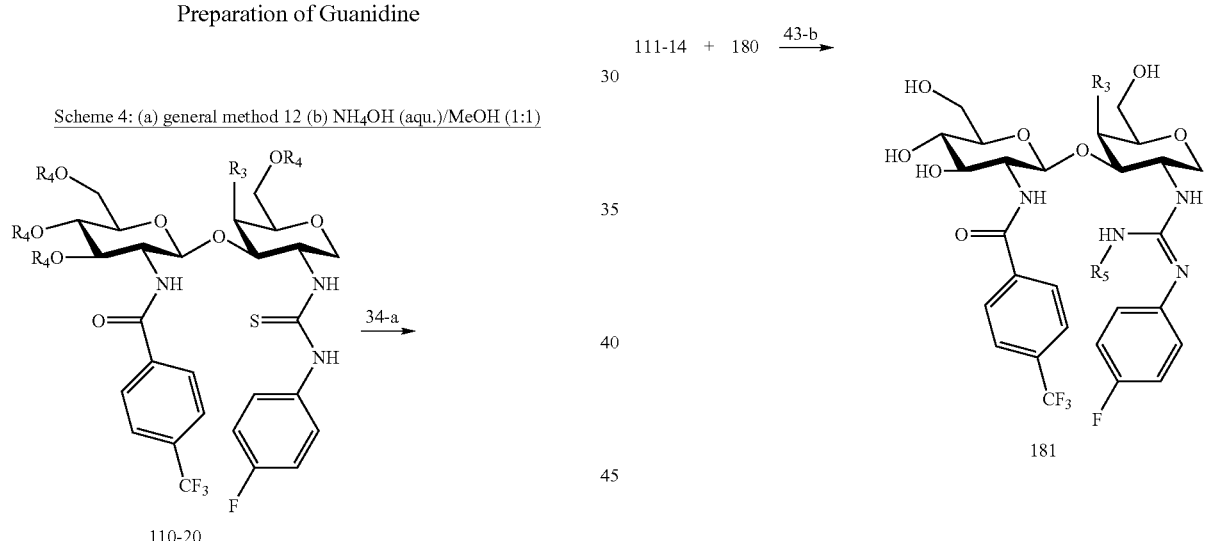

110-20

111-14

+

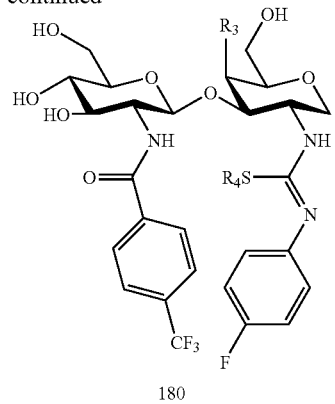

180

111-14 + 180 →(43-b)

181

34-a. Reaction Conditions to Form a Thiourea

Compounds 111-14 and 180 were prepared as a mixture (unpurified) by reaction of compound 110-20 according to the procedure described in General Method 12. The mixture was used directly in the next step.

34-b. Formation of a Guanidine

The sugar mixture (111-14 and 180) (0.025 mmol) was dissolved in methanol (0.5 mL) and concentrated aqueous ammonium hydroxide (0.5 ml) was added. The reaction was stirred at room temperature for 4 hours. The solvents were then removed in vacuo and the residue purified by LCMS.

In a cognate manner, benzylamine, ethylamine, and other primary or secondary amines can be substituted for ammonia to yield the corresponding substituted guanidiniums. Products are shown in table 7.

TABLE 7

Guanidinium products

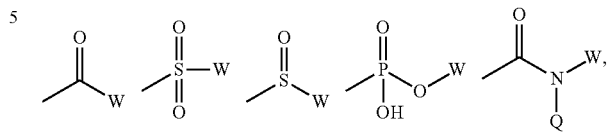

| Product | Starting material | Synth. method | R5* | R2 | R3 | R4 | M+H | Rt (mins) | Yield (%) |
|---|---|---|---|---|---|---|---|---|---|
| 180 | 110-20 | 12 | H | C | A | I | 937.5 | 6.31 | 49 |
| 181 | 111-31 | 17 | H | C | A | I | 800.37 | 5.23 | 75 |
| 182 | 110-20 | 34-b | Bn | C | A | I | ND | ND | ND |
| 183 | 110-20 | 34-b | Et | C | A | I | ND | ND | ND |
| 184 | 110-20 | 34-b | Me | C | A | I | ND | ND | ND |

R5* substituents are Hydrogen (H), Benzyl (Bn), Ethyl (Et), or Methyl (Me): Substituents R2-R4 are as found in Table 2, Example 24.

The invention claimed is:

1. A disaccharide compound of formula (1)

A-d-L-e-B     Formula (1)

wherein A is represented by the formula

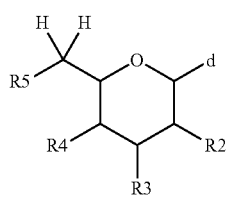

(A)

and B is represented by the formula

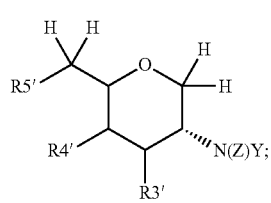

(B)

Y is selected from the group consisting of hydrogen or the following:

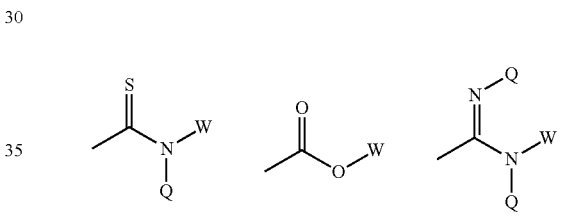

wherein:
Z is selected from hydrogen or X1,
Q is selected from hydrogen or W,
W is a moiety of 1 to 20 non-hydrogen atoms and is selected from the group consisting of alkyl, alkenyl, alkynyl, heteroalkyl, aryl, heteroaryl, arylalkyl and heteroarylalkyl,
X1 is a moiety of 1 to 20 non-hydrogen atoms and is selected from the group consisting of alkyl, alkenyl, alkynyl, heteroalkyl, acyl, arylacyl, heteroarylacyl, aryl, heteroaryl, arylalkyl and heteroarylalkyl,
the groups R2, R3, R4, R5, R3', R4' and R5' are independently selected from the group consisting of hydrogen, $N_3$, OH, OX4, and N(Z)Y, wherein N(Z)Y is as defined above or Y is where Q and W are as defined above, such that at least one of R3', R4' and R5' is OX4 or N(Z)Y, at least one of R2, R3, R4 and R5 is OX4 or N(Z)Y, at least one of R3', R4' and R5' is OH, and at least one of R2, R3, R4 and R5 is OH;
X4 is a moiety of 1 to 20 non-hydrogen atoms and is independently selected from the group consisting of alkyl, alkenyl, alkynyl, heteroalkyl, aminoalkyl, aminoaryl, aryloxy, alkoxy, heteroaryloxy, aminoaryl, aminoheteroaryl, alkylcarbamoyl, arylcarbamoyl heteroarylcarbamoyl, aryl, heteroaryl, arylalkyl and heteroarylalkyl; and
d and e represent the connection points for A and B wherein e replaces one of the groups R3', R4', or R5' in group B and the group d-L-e represents —O—;
and with the provisos that:
a) any of the groups R2 to R5 on ring A may not combine together to form a cycle, and any of the groups R3' to R5' on ring B may not combine to form a cycle,
b) X4 may not be another carbohydrate ring, a cyclitol ring or contain another carbohydrate ring, and
c) all of the X4 substituents may not be the same.

2. The compound of claim 1, wherein X1 is substituted with at least one moiety selected from the group consisting of OH, NO, $NO_2$, $NH_2$, $N_3$, halogen, $CF_3$, $CHF_2$, $CH_2F$, nitrile, alkoxy, aryloxy, amidine, guanidiniums, carboxylic acid, carboxylic acid ester, carboxylic acid amide, aryl, cycloalkyl, heteroalkyl, heteroaryl, aminoalkyl, aminodialkyl, aminotrialkyl, aminoacyl, substituted or unsubstituted imine, sulfate, sulfonamide, phosphate, phosphoramide, hydrazide, hydroxamate, and hydroxamic acid.

3. The compound of claim 1, wherein Z and Y of an N(Z)Y group are combined to form a ring structure of 4 to 10 non-hydrogen atoms.

4. The compound of claim 3, wherein the ring structure is substituted with X1 groups.

5. The compound of claim 1, wherein the structure of formula (1) is

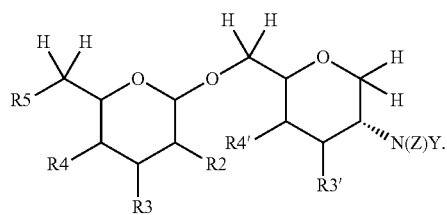

6. The compound of claim 1, wherein the structure of formula (1) is

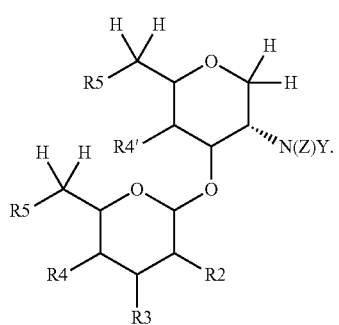

(B)

7. The compound of claim 1, wherein the structure of formula (1) is

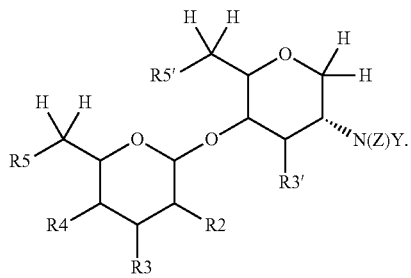

* * * * *